US009180115B2

(12) United States Patent
Thompson et al.

(10) Patent No.: US 9,180,115 B2
(45) Date of Patent: *Nov. 10, 2015

(54) CYCLOHEXYLAMINES

(71) Applicant: Asana Biosciences, LLC, Bridgewater, NJ (US)

(72) Inventors: Scott Kevin Thompson, Phoenixville, PA (US); Roger Astbury Smith, Chester Springs, PA (US); Sandeep Gupta, Plainsboro, NJ (US); Tony Priestley, West Chester, PA (US); Nicholas James Laping, Malvern, PA (US); Ashis K. Saha, Stow, MA (US); Sonali Rudra, Kolkata (IN)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/220,381

(22) Filed: Mar. 20, 2014

(65) Prior Publication Data

US 2014/0213552 A1  Jul. 31, 2014

Related U.S. Application Data

(63) Continuation of application No. 13/659,694, filed on Oct. 24, 2012, now Pat. No. 8,685,418.

(60) Provisional application No. 61/550,489, filed on Oct. 24, 2011, provisional application No. 61/683,519, filed on Aug. 15, 2012.

(51) Int. Cl.
| | |
|---|---|
| A61K 31/69 | (2006.01) |
| A01N 43/40 | (2006.01) |
| A01N 55/08 | (2006.01) |
| A61K 31/40 | (2006.01) |
| C07D 309/14 | (2006.01) |
| C07D 333/38 | (2006.01) |
| C07D 333/40 | (2006.01) |
| C07D 333/70 | (2006.01) |
| C07C 219/12 | (2006.01) |
| C07C 219/14 | (2006.01) |
| C07D 207/34 | (2006.01) |
| A61K 45/06 | (2006.01) |
| A61K 31/215 | (2006.01) |
| A61K 31/235 | (2006.01) |
| A61K 31/24 | (2006.01) |
| A61K 31/351 | (2006.01) |
| A61K 31/381 | (2006.01) |
| C07C 63/49 | (2006.01) |
| C07C 65/26 | (2006.01) |
| C07D 333/72 | (2006.01) |

(52) U.S. Cl.
CPC .............. *A61K 31/40* (2013.01); *A61K 31/215* (2013.01); *A61K 31/235* (2013.01); *A61K 31/24* (2013.01); *A61K 31/351* (2013.01); *A61K 31/381* (2013.01); *A61K 45/06* (2013.01); *C07C 63/49* (2013.01); *C07C 65/26* (2013.01); *C07C 219/12* (2013.01); *C07C 219/14* (2013.01); *C07D 207/34* (2013.01); *C07D 309/14* (2013.01); *C07D 333/38* (2013.01); *C07D 333/40* (2013.01); *C07D 333/70* (2013.01); *C07D 333/72* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 4,069,309 A | 1/1978 | Ciaudelli | |
| 4,656,256 A | 4/1987 | Colberg | |
| 4,694,075 A | 9/1987 | Colberg | |
| 4,695,405 A | 9/1987 | Harnisch | |
| 4,871,387 A | 10/1989 | Sasse | |
| 5,464,719 A | 11/1995 | Wilson | |
| 6,333,325 B1 | 12/2001 | Cirillo | |
| 8,685,418 B2 * | 4/2014 | Thompson et al. | ........... 424/400 |
| 2004/0214867 A1 | 10/2004 | Choi | |

(Continued)

FOREIGN PATENT DOCUMENTS

| | | |
|---|---|---|
| JP | 47-002623 | 1/1972 |
| WO | WO 00/76510 | 12/2000 |

(Continued)

OTHER PUBLICATIONS

Lindborg et al. (1984, Acta Pharm. Suec., 21, 271-294).*
Binshtok, "Inhibition of nociceptors by TRPV1-mediated entry of impermeant sodium channel blockers", Nature 449(4):607-611 (Oct. 2007).

(Continued)

*Primary Examiner* — Dennis Heyer
*Assistant Examiner* — Daniel M Podgorski
(74) *Attorney, Agent, or Firm* — Lerner, David, Littenberg, Krumholz & Mentlik, LLP

(57) ABSTRACT

The present application provides novel compounds and methods for preparing and using these compounds. These compounds are useful in treating pain, itch, overactive bladder and/or interstitial cystitis in patients by administering one or more of the compounds to a patient. The methods include administering a compound of formula (I) and a TRPV1 receptor activator. In one embodiment, the TRPV1 receptor activator is lidocaine.

18 Claims, 2 Drawing Sheets

(56) References Cited

U.S. PATENT DOCUMENTS

| | | |
|---|---|---|
| 2010/0099772 A1 | 4/2010 | Bean |
| 2011/0086818 A1 | 4/2011 | Bean |
| 2011/0319378 A1 | 12/2011 | Bartberger |
| 2012/0214809 A1 | 8/2012 | Thompson |

FOREIGN PATENT DOCUMENTS

| | | |
|---|---|---|
| WO | WO 01/44218 | 6/2001 |
| WO | WO 2006/036936 | 4/2006 |
| WO | WO 2007/038325 | 4/2007 |
| WO | WO 2008/063603 | 5/2008 |
| WO | WO 2009/114139 | 9/2009 |
| WO | WO 2010/036878 | 4/2010 |
| WO | WO 2011/006073 | 1/2011 |
| WO | WO 2011/028740 | 3/2011 |
| WO | WO 2012/112969 | 8/2012 |

OTHER PUBLICATIONS

Blumberg, "Lighting a backfire to quench the blaze: A combined drug approach targeting the vanilloid receptor TRPV1", Molecular Interventions 7(6):310-312 (Dec. 2007).

Chu et al., 1994, Cell Biochemistry and Function, 12, 89-98.

Clouse, "Voltage-gated Na$^+$ channel blocker reduce functional bladder capacity in the conscious spontaneously hypertensive rat", Urology, 79(6):1410.e1-1410.e6 (Jun. 2012; e-publication: Apr. 11, 2012).

International Search Report and Written Opinion dated Jan. 2, 2013 and issued in counterpart International Patent Application No. PCT/US2012/061703.

International Search Report dated May 25, 2012 and issued in International Patent Application No. PCT/US2012/025759.

Kamatani, Japanese Patent No. 47-002623 (Jan. 25, 1972)—English abstract.

Lindborg ete al., 1984, Acta Pharm. Suec. 21, 271-294.

Lindborg, "Troxonium-Like Inhibitors of the High Affinity Uptake of Choline in Mouse Brain Synaptosomes in Vitro", Acta Pharmaceutica Suecica, 21(5):271-294 (Jan. 1, 1984).

Mndzhoyan, "Derivatives of p-Alkoxybenzoic Acids. XXI. Some Cyclohexylalkylaminoalkyl Esters of p-Butoxybenzoic Acids", Izvestiya Akademii Nauk Armyanskoi SSR, 16(2):163-174 (1963)—English abstract.

Roberson, "Targeting of sodium channel blockers into nociceptors to produce long-duration analgesia: a systematic study and review", British Journal of Pharmacology, 164(1):48-58 (Sep. 2011; e-publication: Aug. 5, 2011).

Su, "Pharmacologic evaluation of pressor and visceromotor reflex responses to bladder distension", Neurourology and Urodynamics, 27(3):249-253 (2008; e-publication: Jun. 27, 2007).

Zuliani, "Sodium channel blockers for neuropathic pain", Expert Opinion Therapeutic Patents, 20(6):755-779 (Jun. 2010).

* cited by examiner

Dose-response relationship for the analgesic effects of the compound of example 5 in combination with a fixed dose of lidocaine (2%) in the rat pinch-pain model Effect of injection volume on duration of analgesia observed with the compound of example 6

```
                         SEQUENCE LISTING

<160> NUMBER OF SEQ ID NOS: 4

<210> SEQ ID NO 1
<211> LENGTH: 839
<212> TYPE: PRT
<213> ORGANISM: Homo sapiens

<400> SEQUENCE: 1

Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
        50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
                115                 120                 125

Asp Leu Glu Ser Leu Leu Leu Phe Leu Gln Lys Ser Lys Lys His Leu
            130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
            210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
                260                 265                 270

Trp Gln Thr Ala Asp Ile Ser Ala Arg Asp Ser Val Gly Asn Thr Val
            275                 280                 285

Leu His Ala Leu Val Glu Val Ala Asp Asn Thr Ala Asp Asn Thr Lys
            290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
```

```
                    340                 345                 350
Ile Leu Gln Arg Glu Ile Gln Glu Pro Glu Cys Arg His Leu Ser Arg
                355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
    450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Phe Arg Gly Ile Gln Tyr Phe
                485                 490                 495

Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
            580                 585                 590

Thr Ala Val Val Thr Leu Ile Glu Asp Gly Lys Asn Asp Ser Leu Pro
        595                 600                 605

Ser Glu Ser Thr Ser His Arg Trp Arg Gly Pro Ala Cys Arg Pro Pro
    610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
            660                 665                 670

Ile Leu Leu Leu Asn Met Leu Ile Ala Leu Met Gly Glu Thr Val Asn
        675                 680                 685

Lys Ile Ala Gln Glu Ser Lys Asn Ile Trp Lys Leu Gln Arg Ala Ile
    690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
                725                 730                 735

Asp Asp Tyr Arg Trp Cys Phe Arg Val Asp Glu Val Asn Trp Thr Thr
            740                 745                 750

Trp Asn Thr Asn Val Gly Ile Ile Asn Glu Asp Pro Gly Asn Cys Glu
        755                 760                 765
```

```
Gly Val Lys Arg Thr Leu Ser Phe Ser Leu Arg Ser Ser Arg Val Ser
        770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
            820                 825                 830

Pro Ala Ala Ser Gly Glu Lys
        835

<210> SEQ ID NO 2
<211> LENGTH: 41
<212> TYPE: DNA
<213> ORGANISM: Artificial Sequence
<220> FEATURE:
<223> OTHER INFORMATION: primer

<400> SEQUENCE: 2
ataaacggta ccgccgccac catgaagaaa tggagcagca c                    41

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
atcggtttaa actcacttct ctccggaagc ggc                             33

<210> SEQ ID NO 4
<211> LENGTH: 2520
<212> TYPE: DNA
<213> ORGANISM: Homo sapiens

<400> SEQUENCE: 4
atgaagaaat ggagcagcac agacttgggg gcagctgcgg acccactcca aaaggacacc    60
tgcccagacc ccctggatgg agaccctaac tccaggccac ctccagccaa gccccagctc   120
tccacggcca agagccgcac ccggctcttt gggaagggtg actcggagga ggcttttccg   180
gtggattgcc ctcacgagga aggtgagctg gactcctgcc cgaccatcac agtcagccct   240
gttatcacca tccagaggcc aggagacggc ccaccggtg ccaggctgct gtcccaggac   300
tctgtcgccg ccagcaccga gaagaccctc aggctctatg atcgcaggag tatctttgaa   360
gccgttgctc agaataactg ccaggatctg gagagcctgc tgctcttcct gcagaagagc   420
aagaagcacc tcacagacaa cgagttcaaa gaccctgaga cagggaagac ctgtctgctg   480
aaagccatgc tcaacctgca cgacggacag aacaccacca tccccctgct cctggagatc   540
gcgcggcaaa cggacagcct gaaggagctt gtcaacgcca gctacacgga cagctactac   600
aagggccaga cagcactgca catcgccatc gagagacgca catggccct ggtgaccctc   660 ctggtggaga acgagcagag cgtccaggct gcggcccatg ggacttctt taagaaaacc   720 aaagggcggc ctggattcta cttcggtgaa ctgcccctgt ccctggccgc gtgcaccaac   780
cagctgggca tcgtgaagtt cctgctgcag aactcctggc agacggccga catcagcgcc   840
agggactcgg tgggcaacac ggtgctgcac gccctggtgg aggtggccga caacacggcc   900
gacaacacga gtttgtgac gagcatgtac aatgagattc tgatcctggg ggccaaactg   960
```

```
cacccgacgc tgaagctgga ggagctcacc aacaagaagg gaatgacgcc gctggctctg    1020
gcagctggga ccgggaagat cggggtcttg gcctatattc tccagcggga gatccaggag    1080
cccgagtgca ggcacctgtc caggaagttc accgagtggg cctacgggcc cgtgcactcc    1140
tcgctgtacg acctgtcctg catcgacacc tgcgagaaga actcggtgct ggaggtgatc    1200
gcctacagca gcagcgagac ccctaatcgc cacgacatgc tcttggtgga gccgctgaac    1260
cgactcctgc aggacaagtg ggacagattc gtcaagcgca tcttctactt caacttcctg    1320
gtctactgcc tgtacatgat catcttcacc atggctgcct actacaggcc cgtggatggc    1380
ttgcctccct ttaagatgga aaaaactgga gactatttcc gagttactgg agagatcctg    1440
tctgtgttag gaggagtcta cttcttttc cgagggattc agtatttcct gcagaggcgg    1500
ccgtcgatga agaccctgtt tgtggacagc tacagtgaga tgcttttctt tctgcagtca    1560
ctgttcatgc tggccaccgt ggtgctgtac ttcagccacc tcaaggagta tgtggcttcc    1620
atggtattct ccctggcctt gggctggacc aacatgctct actacacccg cggtttccag    1680
cagatgggca tctatgccgt catgatagag aagatgatcc tgagagacct gtgccgtttc    1740
atgtttgtct acatcgtctt cttgttcggg ttttccacag cggtggtgac gctgattgaa    1800
gacgggaaga atgactccct gccgtctgag tccacgtcgc acaggtggcg ggggcctgcc    1860
tgcaggcccc ccgatagctc ctacaacagc ctgtactcca cctgcctgga gctgttcaag    1920
ttcaccatcg gcatgggcga cctggagttc actgagaact atgacttcaa ggctgtcttc    1980
atcatcctgc tgctggccta tgtaattctc acctacatcc tcctgctcaa catgctcatc    2040
gccctcatgg gtgagactgt caacaagatc gcacaggaga gcaagaacat ctggaagctg    2100
cagagagcca tcaccatcct ggacacggag aagagcttcc ttaagtgcat gaggaaggcc    2160
ttccgctcag gcaagctgct gcaggtgggg tacacacctg atggcaagga cgactaccgg    2220
tggtgcttca gggtggacga ggtgaactgg accacctgga acaccaacgt gggcatcatc    2280
aacgaagacc cgggcaactg tgagggcgtc aagcgcaccc tgagcttctc cctgcggtca    2340
agcagagttt caggcagaca ctggaagaac tttgccctgg tcccccttt aagagaggca    2400 agtgctcgag ataggcagtc tgctcagccc gaggaagttt atctgcgaca gttttcaggg    2460
tctctgaagc cagaggacgc tgaggtcttc aagagtcctg ccgcttccgg agagaagtga    2520
```

CYCLOHEXYLAMINES

CROSS REFERENCE TO RELATED APPLICATIONS

This application is a continuation application of U.S. patent application Ser. No. 13/659,694, filed Oct. 24, 2012, allowed, which claims priority to U.S. Provisional Patent Application No. 61/550,489, filed Oct. 24, 2011 and U.S. Provisional Patent Application No. 61/683,519, filed Aug. 15, 2012, the contents of all of which are incorporated by reference in their entireties for all purposes.

BACKGROUND

Sodium channel blockers play key roles in a large number of functions related to the body. In addition to the naturally produced sodium channel blockers produced in the body, a variety of non-naturally occurring drugs are utilized to block sodium channels from the intracellular side of the channel. For example, local anesthetics are non-selective sodium channel blockers that fail to discriminate between sodium channel activity required for normal ongoing sensation and similar activity involved in nociceptor signaling. There are, however, useful in pain relief in numerous applications, but suffer from the drawback of undesired blockade of motor function.

The sodium channel is also implicated in conditions of the bladder, e.g., interstitial cystitis (IC—bladder pain along with increased urinary frequency; also known as painful bladder syndrome) and overactive bladder (OAB—bladder storage issues such as urgency, frequency and nocturia). OAB presents as an increased voiding frequency and may be the result of infection or injury to the bladder tissue itself, e.g., interstitial cystitis, or may arise as a comorbid association to conditions such as stress, anxiety disorder, endometriosis, vulvodynia, chronic fatigue syndrome, or fibromyalgia, among other conditions. In both IC and OAB, increased afferent signals are conducted by myelinated Aδ-fibers and the unmyelinated C-fibers. Typically the C-fibers mediate painful mechanical, thermal and chemical sensations and this signaling requires action potentials that are initiated and maintained via activated sodium channels. Therefore, targeting the sodium channel mediated conduction of action potentials in bladder C-fiber afferent nerves may be a therapeutic approach for the treatment of OAB and IC (Steers, 2002, Rev. Urol., 4 Suppl 4:S7-S18). In an animal model of IC and OAB, blocking the conduction of afferent signals with the sodium channel blocker lidocaine, normalizes the micturition pattern as determined by cystometry (Juszczak, 2009, J. Physiol. Pharmacol. December, 60(4):85-91). Similarly, mexilitine prevents the painful sensation of noxious urinary bladder distention (Su, 2008, Neurourol. Urodyn., 27(3):249-53). Unfortunately neither lidocaine nor mexilitine offer therapeutically tractable options for patients with these bladder conditions due to the fact that their beneficial effects are short-lived.

The cationic sodium channel blocker, QX-314, selectively blocks sodium channel activity in nociceptor neurons when administered in the presence of capsaicin, an agonist for the transient receptor potential cation channel, subfamily V, member 1 (TRPV1). TRPV1 is preferentially expressed peripherally in small-diameter primary afferent nociceptors and is up-regulated in chronic pain states. However, TRPV1 is not present in the large diameter afferent neurons that convey tactile sensations nor is TRPV1 present in motor neuron efferent fibers.

QX-314 is the N-methylated analog of lidocaine and bears a permanent positive charge. It is unable to cross the neuronal cell membrane when applied externally and has no effect on neuronal sodium-channel activity unless afforded access, to the cell cytoplasm, through open TRPV1 channels in which case it causes prolonged block of sodium-channel activity. Voltage-clamp single cell electrophysiology experiments illustrated that QX-314 permeates through capsaicin-activated TRPV1 channels and blocks sodium channel activity. In vivo, perisciatic administration of a QX-314/capsaicin combination produced pronounced and long-lasting nociceptor-selective nerve blockade.

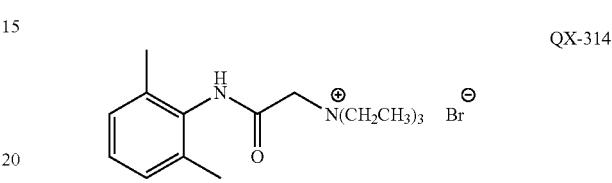

QX-314

The in vitro apparent affinity ($IC_{50}$) of QX-314 for blocking sodium current in DRG neurons (when co-applied with 1 μM capsaicin and measured using the whole-cell voltage clamp approach) is modest at 30 μM.

There remains a need in the art for new and novel cationic sodium channel blockers with more potent activity than QX-314 in vitro and longer duration of action in vivo when utilized alone or co-administered with appropriate TRPV1 stimuli.

SUMMARY OF THE INVENTION

In one aspect, the present invention provides a compound of formula (I), wherein $R^1$, $R^2$, A, X, and Y are defined herein.

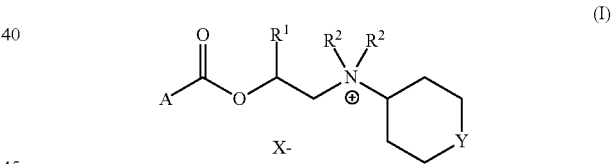

(I)

In yet another aspect, the invention provides a pharmaceutical composition containing a compound of formula (I) and a pharmaceutically acceptable carrier. In one embodiment, the pharmaceutical composition also contains a TRPV1 receptor activator. In another embodiment, the TRPV1 receptor activator is lidocaine.

In another aspect, methods for treating pain or itch are provided and include administering a compound of formula (I) to a patient in need thereof. In one embodiment, the methods also include administration of a TRPV1 receptor activator.

In a further aspect, methods for treating overactive bladder are provided and include administering a compound of formula (I), wherein $R^1$, $R^2$, A, X, and Y are defined herein, to a patient in need thereof.

In still another aspect, methods for treating interstitial cystitis, i.e., painful bladder syndrome, are provided and include administering a compound of formula (I) to a patient in need thereof.

In yet a further aspect, any of the methods described herein also include administration of a TRPV1 receptor activator.

Other aspects and advantages of the invention will be readily apparent from the following detailed description of the invention.

BRIEF DESCRIPTION OF THE DRAWINGS

FIG. 1 illustrates the anti-nociceptive effect of the compound of example 5, i.e., (S)—N-[2-((4-(tert-butyl)benzoyl)oxy)propyl]-N,N-dimethylcyclohexanaminium bromide using the rat pinch model. Varying doses of (S)—N-[2-((4-(tert-butyl)benzoyl)oxy)propyl]-N,N-dimethylcyclohexanaminium bromide solutions were utilized in the presence of a fixed amount (2%) of lidocaine. The black triangles (▲) represent results for a 0.2% solution of (S)—N-[2-((4-(tert-butyl)benzoyl)oxy)propyl]-N,N-dimethylcyclohexanaminium bromide. The black circles (●) represent results for a 0.3% solution of (S)—N-[2-((4-(tert-butyl)benzoyl)oxy)propyl]-N,N-dimethylcyclohexanaminium bromide. The black squares (■) represent results for a 0.4% solution of (S)—N-[2-((4-(tert-butyl)benzoyl)oxy)propyl]-N,N-dimethylcyclohexanaminium bromide. The inverted triangles (▼) represent results for a 0.45% (S)—N-[2-((4-(tert-butyl)benzoyl)oxy)propyl]-N,N-dimethylcyclohexanaminium bromide solution. Finally, the arrow (→) on the y-axis represents the highest force applied. Animals treated with 0.45% (S)—N-[2-((4-(tert-butyl)benzoyl)oxy)propyl]-N,N-dimethylcyclohexanaminium bromide remained at cut-off for the duration of the experiment.

FIG. 2 illustrates the effect of injection volume on duration of analgesia for the compound of example 6, i.e., N-[2-((2,6-Dimethylbenzoyl)oxy)propyl]-N,N-dimethylcyclohexanaminium iodide using the rat pinch model. The black circles (●) represent results for a 200 μL of a solution containing 0.5% of N-[2-((2,6-Dimethylbenzoyl)oxy)propyl]-N,N-dimethylcyclohexanaminium iodide. The inverted triangles (▼) represent results for 100 μL of a solution containing 0.5% N-[2-((2,6-Dimethylbenzoyl)oxy)propyl]-N,N-dimethylcyclohexanaminium iodide.

DETAILED DESCRIPTION OF THE INVENTION

Figure 1:
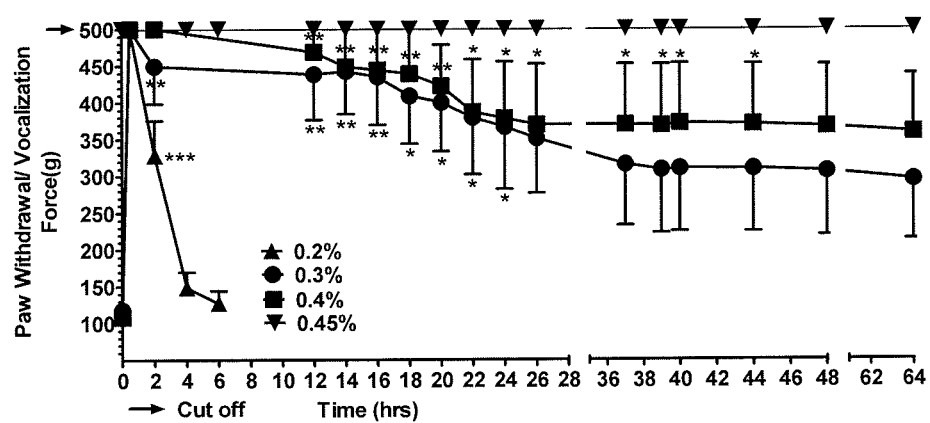
FIGS. 1-2 provide comparative data illustrating the analgesic effects of two compounds described herein which are encompassed by the compound of formula (I). All figures are plots of paw withdrawal vocalization force (g) vs. time (hours). Three stars (*) designate a probability of less than 0.001. Two stars () designate a probability of less than 0.01. One star (*) designates a probability of less than 0.05. The bars (⊢⊣) contained within the graph, if present, represent the difference between the duration of anti-nociception with lidocaine.

The present invention provides novel compounds which, when optionally utilized in combination with a TRPV1 agonist, are capable in reducing or eliminating pain or itch caused by tissue insult, injury or pathology, or treating overactive bladder, and/or interstitial cystitis.

These novel compounds are permanently charged by virtue of the quaternary nitrogen-atom contained within the nitrogen-containing ring rendering them highly soluble. These compounds are quaternary ammonium salts, where the counter-anion is a chloride, bromide, iodide, trifluoroacetate, sulfate, phosphate, acetate, fumarate, maleate, citrate, pyruvate, succinate, oxalate, sulfonate, bisulfate, malonate, xinafoate, ascorbate, oleate, nicotinate, saccharinate, adipate, formate, glycolate, L-lactate, D-lactate, aspartate, malate, tartrate, L-tartrate, D-tartrate, stearate, 2-furoate, 3-furoate, napadisylate, edisylate, isethionate, D-mandelate, L-mandelate, propionate, phthalate, hydrochlorate, hydrobromate, nitrate, methanesulfonate, napthalenesulfonate, benzenesulfonate, toluenesulfonate, camphorsulfonate or trifluoromethanesulfonate.

The novel charged compounds disclosed herein are incapable of passing through the cell membrane. However, it is believed that they will penetrate into the cell, in therapeutically effective amounts, when access is afforded via open TRPV1 channels. This is one advantage of the charged compounds of the invention as compared to their corresponding neutral molecules that are believed to freely penetrate all cell membranes.

In one aspect, the present invention provides a compound of formula (I).

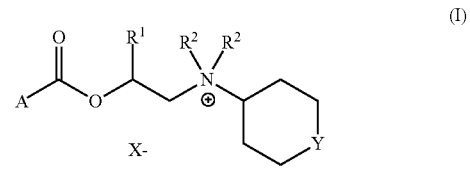

In this formula, $R^1$ is H or $C_1$ to $C_6$ alkyl. In one embodiment, $R^1$ is H. In another embodiment, $R^1$ is $CH_3$.

$R^2$ in formula (I) is $C_1$ to $C_6$ alkyl. In one embodiment, $R^2$ is $CH_3$. In a further embodiment, $R^2$ is $CH_2CH_3$. In yet another embodiment, the two $R^2$ groups are joined together to form a 5- or 6-membered ring.

The Y substituent is O or $CHR^3$. In one embodiment, Y is O. In another embodiment, Y is $CHR^3$.

The $R^3$ moiety is H or $C_1$ to $C_6$ alkyl. In one embodiment, $R^3$ is H. In a further embodiment, $R^3$ is $CH_3$.

A of formula (I) is optionally substituted phenyl, optionally substituted heteroaryl or optionally substituted cycloalkyl. However, when A is unsubstituted phenyl, $R^1$ and $R^2$ are not methyl and $R^3$ is not H.

i. In one embodiment, A is:

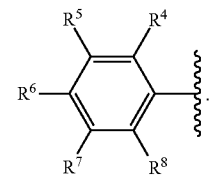

In this structure, $R^4$, $R^5$, $R^6$, $R^7$, and $R^8$ are, independently, selected from among H, optionally substituted $C_1$ to $C_6$ alkyl, optionally substituted $C_1$ to $C_6$ alkoxy, halogen, $C_1$ to $C_3$ perfluoroalkyl, and $NO_2$.

ii. In another embodiment, A is:

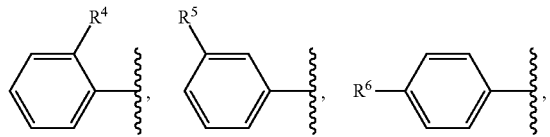

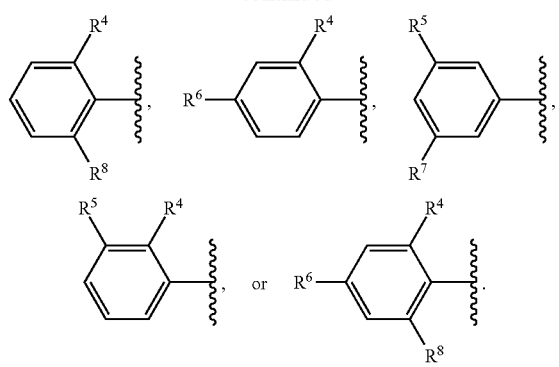

iii. In a further embodiment, A is of the structures noted in options i or ii and $R^4$, $R^5$, $R^6$, $R^7$, and $R^8$ are, independently, selected from among $OCH_3$, $CH_3$, $CH_2CH_3$, $CH(CH_3)_2$, $C(CH_3)_3$, Cl, F, $CF_3$, and $NO_2$.

iv. In still another embodiment, A is an optionally substituted pyrrole.

v. In yet a further embodiment, A is:

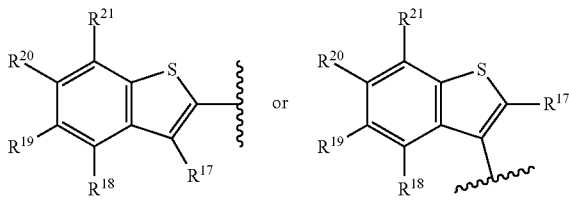

In these structures, $R^9$, $R^{19}$, and $R^{11}$ are, independently, H, optionally substituted $C_1$ to $C_6$ alkyl, or halogen; and $R^{12}$ is H or $C_1$ to $C_6$ alkyl.

vi. In another embodiment, A is the following and $R^{12}$ is defined as noted in option v:

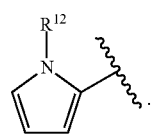

vii. In still a further embodiment, $R^{12}$ is $CH_3$ in options v or vi noted above.

viii. In yet a further embodiment, A is an optionally substituted thiophene.

ix. In another embodiment, A is:

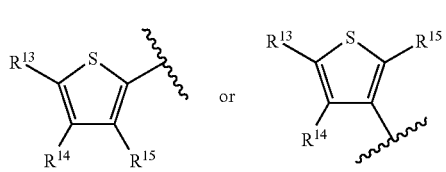

In these structures, $R^{13}$, $R^{14}$, and $R^{15}$ are, independently, H, optionally substituted $C_1$ to $C_6$ alkyl, or halogen.

x. In still another embodiment, A is:

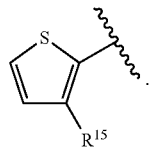

xi. In yet a further embodiment, $R^{15}$ in options ix or x noted above is $CH_3$.

xii. In another embodiment, A is an optionally substituted benzothiophene.

xiii. In still another embodiment, A is:

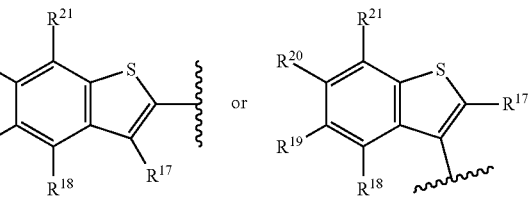

In these structures, $R^{17}$, $R^{18}$, $R^{19}$, $R^{20}$, and $R^{21}$ are, independently, H, optionally xiv. In a further embodiment, A is of the following structure and $R^{17}$ is defined as in option xiii:

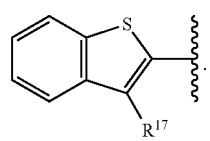

xv. In yet another embodiment, $R^{17}$ as in options xiii and xiv is halogen.

In the compounds of formula (I), X is chloride, bromide, iodide, trifluoroacetate, sulfate, phosphate, acetate, fumarate, maleate, citrate, pyruvate, succinate, oxalate, sulfonate, bisulfate, malonate, xinafoate, ascorbate, oleate, nicotinate, saccharinate, adipate, formate, glycolate, L-lactate, D-lactate, aspartate, malate, tartrate, L-tartrate, D-tartrate, stearate, 2-furoate, 3-furoate, napadisylate, edisylate, isethionate, D-mandelate, L-mandelate, propionate, phthalate, hydrochlorate, hydrobromate, nitrate, methanesulfonate, napthalenesulfonate, benzenesulfonate, toluenesulfonate, camphorsulfonate or trifluoromethanesulfonate.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched. In one embodiment, an alkyl contains 1 to 6 (inclusive) carbon atoms. In another embodiment, an alkyl contains 1 to 5 (inclusive) carbon atoms. In a further embodiment, an alkyl contains 1 to 4 (inclusive) carbon atoms. In yet another embodiment, an alkyl contains 1 to 3 (inclusive) carbon atoms. In still a further embodiment, an alkyl contains 1 or 2 carbon atoms. Examples of alkyl groups that are hydrocarbon chains include, but are not limited to, methyl, ethyl, propyl, butyl, pentyl, and hexyl, where all isomers of these examples are contemplated.

Alkyl groups may also consist of or contain a cyclic alkyl radical, i.e., "carbocyclic ring". Examples of carbocyclic rings include, but are not limited to, cyclopropyl, cyclobutyl, cyclopentyl, cyclohexyl, and the like. In one embodiment, the carbocyclic ring is 3- to 6-membered. In a further embodiment, the carbocyclic ring is 3- to 5-membered. In still a further embodiment, the carbocyclic ring is 4- to 6-membered. In another embodiment, the carbocyclic ring is 3- or 4-membered, i.e., cyclopropyl or cyclobutyl. Unless specifically noted, the alkyl groups are unsubstituted, i.e., they contain carbon and hydrogen atoms only. However, when the alkyl group or carbocyclic ring is substituted, it is prefaced with the term "optionally substituted" or "substituted". The optional substituents of the alkyl groups or carbocyclic rings include, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkyl-$C_1$ to $C_6$ alkoxy, heterocyclyloxy, $C_1$ to $C_6$ alkylthio, aryl, heterocycle, heteroaryl, $C(O)(C_1$ to $C_6$ alkyl), C(O)(heterocycle), $C(O)O(C_1$ to $C_6$ alkyl), $C(O)NH_2$, $C(O)NH(C_1$ to $C_6$ alkyl), $C(O)N(C_1$ to $C_6$ alkyl)($C_1$ to $C_6$ alkyl), $SO_2(C_1$ to $C_6$ alkyl), $SO_2(C_2$ to $C_6$ alkynyl), $SO_2NH(C_1$ to $C_6$ alkyl), $SO_2$(heterocycle), $NHC(O)(C_1$ to $C_6$ alkyl), $NHSO_2(C_1$ to $C_6$ alkyl), $N(C_1$ to $C_6$ alkyl)$SO_2(C_1$ to $C_6$ alkyl), $NH_2$, NH(aryl), $N(C_1$ to $C_6$ alkyl)($C_1$ to $C_6$ alkyl), or $NHC(O)NH_2$.

"Alkoxy" refers to ∼O(alkyl), where the alkyl is optionally substituted and is defined above. In one embodiment, an alkoxy contains 1 to 6 (inclusive) carbon atoms or integers or ranges there between. In another embodiment, an alkoxy contains 1 to 5 (inclusive) carbon atoms or ranges there between. In a further embodiment, an alkoxy contains 1 to 4 (inclusive) carbon atoms. In yet another embodiment, an alkoxy contains 1 to 3 (inclusive) carbon atoms. In still a further embodiment, an alkoxy contains 1 or 2 carbon atoms. Examples of alkoxy include, but are not limited to, methoxy, ethoxy, propoxy, and butoxy. The alkyl radical of an alkoxy group can be unsubstituted or substituted as defined above for "alkyl".

"Aryl" refers to an aromatic hydrocarbon group containing carbon atoms. In one embodiment, the aryl contains 6 to 10 carbon atoms, i.e., 6-, 7-, 8-, 9- or 10-membered. In another embodiment, aryl is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, $C(O)(C_1$ to $C_6$ alkyl), C(O)(heterocycle), $C(O)O(C_1$ to $C_6$ alkyl), $C(O)NH_2$, $C(O)NH(C_1$ to $C_6$ alkyl), $C(O)N(C_1$ to $C_6$ alkyl)($C_1$ to $C_6$ alkyl), $SO_2(C_1$ to $C_6$ alkyl), $SO_2(C_2$ to $C_6$ alkynyl), $SO_2NH(C_1$ to $C_6$ alkyl), $SO_2$(heterocycle), $NHSO_2(C_1$ to $C_6$ alkyl), $N(C_1$ to $C_6$ alkyl)$SO_2(C_1$ to $C_6$ alkyl), $NH_2$, NH(aryl) or $NHC(O)NH_2$.

"Halogen" refers to F, Cl, Br and I.

The term "heteroatom" refers to a sulfur, nitrogen, or oxygen atom.

"Heteroaryl" refers to a monocyclic aromatic 5- or 6-membered ring containing at least one ring heteroatom. In one embodiment, the heteroaryl contains 1 to 5 carbon atoms (inclusive) or integers or ranges there between. In a further embodiment, the heteroaryl contains 2 to 5 carbon atoms (inclusive). In another embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In yet a further embodiment, the bicyclic heteroaryl is a pyridine fused to a 5- or 6-membered monocyclic heteroaryl. In still another embodiment, the heteroaryl ring has 1 or 2 nitrogen atoms in the ring. In a further embodiment, the heteroaryl ring has 1 nitrogen atom and 1 oxygen atom. In yet another embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, $C(O)(C_1$ to $C_6$ alkyl), C(O)(heterocycle), $C(O)O(C_1$ to $C_6$ alkyl), $C(O)NH_2$, $C(O)NH(C_1$ to $C_6$ alkyl), $C(O)N(C_1$ to $C_6$ alkyl)($C_1$ to $C_6$ alkyl), $SO_2(C_1$ to $C_6$ alkyl), $SO_2(C_2$ to $C_6$ alkynyl), $SO_2NH(C_1$ to $C_6$ alkyl), $SO_2$(heterocycle), $NHC(O)(C_1$ to $C_6$ alkyl), $NHSO_2(C_1$ to $C_6$ alkyl), $N(C_1$ to $C_6$ alkyl)$SO_2(C_1$ to $C_6$ alkyl), $NH_2$, NH(aryl), $N(C_1$ to $C_6$ alkyl)($C_1$ to $C_6$ alkyl) or $NHC(O)NH_2$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges there between. In a further embodiment, the heterocycle contains 4 to 7 carbon atoms (inclusive). In another embodiment, the heterocycle contains 4 to 6 carbon atoms (inclusive). In still a further embodiment, the heterocycle contains 5 or 6 carbon atoms (inclusive). Examples of heterocycles include, but are not limited, to aziridine, oxirane, thiirane, morpholine, thiomorpholine, pyrroline, pyrrolidine, azepane, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In yet another embodiment, the heterocycle contains 1 or 2 nitrogen atoms, 3 to 6 carbon atoms, and 1 oxygen atom. In a further embodiment, the heterocycle is 5- to 8-membered. In another embodiment, the heterocycle is 5-membered. In still a further embodiment, the heterocycle is 6-membered. In yet another embodiment, the heterocycle is 8-membered. A heterocycle may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkylamino" refers to an NH or N group, the nitrogen atom of the group being attached to 1 or 2 alkyl substituents, respectively, wherein the alkyl is optionally substituted and defined above. The alkylamino is bound through the nitrogen atom of the group. In one embodiment, alkylamino refers to ∿NH(alkyl). In another embodiment, alkylamino refers to ∿N(alkyl)(alkyl), i.e., a "dialkylamino". In a further embodiment, alkylamino refers to ∿N($C_1$ to $C_6$ alkyl)($C_1$ to $C_6$ alkyl). In yet another embodiment, alkylamino refers to ∿N(alkyl)(heterocycle). In still a further embodiment, alkylamino refers to ∿N(alkyl)(aryl). In another embodiment, alkylamino refers to ∿N(alkyl)(heteroaryl). In et a further embodiment, alkylamino refers to ∿N(alkyl)(alkenyl). When the nitrogen atom is bound to two alkyl groups, each alkyl group may be independently selected. In another embodiment, two alkyl groups on the nitrogen atom may be taken together with the nitrogen to which they are attached to form a 3- to 4-membered nitrogen-containing heterocycle where up to two of the carbon atoms of the heterocycle can be replaced with N(H), N($C_1$ to $C_6$ alkyl), N(aryl), N(heteroaryl), O, S(O), or S(O)$_2$. Examples of alkylamino include, but are not limited to N($CH_3$)$_2$, N($CH_2CH_3$)($CH_3$), N($CH_2CH_3$)$_2$, N($CH_2CH_2CH_3$)$_2$, N($CH_2CH_2CH_2CH_3$)$_2$, N(CH($CH_3$)$_2$)($CH_3$), and the like.

"Arylamino" refers to an NH or N group, the nitrogen atom of the group being attached to 1 or 2 aryl substituents, respectively, wherein the aryl is optionally substituted and defined above. The arylamino is bound through the nitrogen atom of the group. In one embodiment, arylamino refers to NH(aryl). In another embodiment, arylamino refers to ∿N(aryl)(aryl), i.e., a "diarylamino". When the nitrogen atom is bound to two aryl groups, each aryl may be independently selected.

"Alkylcarbonylamino" refers to ∿NHC(O)(alkyl) or ∿N(alkyl)C(O)(alkyl) where the alkyl groups are independently defined and independently optionally substituted as described above. Examples of alkylcarbonylamino include, but are not limited to, $CH_3$CONH, $CH_3CH_2$CONH, $CH_3CH_2CH_2$CONH, $CH_3$CH($CH_3$)CONH, and the like.

"Ester" refers to ∿C(O)O(alkyl), which is bound through the carbon atom. The alkyl group is defined and optionally substituted as described above. Examples of ester include, without limitation, C(O)O$CH_3$, C(O)O($CH_2CH_3$), C(O)O($CH_2CH_2CH_3$), C(O)O($CH_2CH_2CH_2CH_3$), and the like.

"Urea" refers to a group having a ∿NHC(O)NH∿ where one of the nitrogen atoms is bound to an alkyl or heteroaryl group. The alkyl or heteroaryl groups are defined and optionally substituted as described above. Examples of urea include, without limitation, NHC(O)NH$CH_3$, NHC(O)NH$CH_2CH_3$, NHC(O)NH$CH_2CH_2CH_3$, NHC(O)NH$CH_2CH_2CH_2CH_3$, and the like.

"Alkylaminocarbonyl" refers to ∿C(O)NH(alkyl) or ∿C(O)N(alkyl)(alkyl) where the alkyl groups are independently defined and independently optionally substituted as described above. Examples of alkylaminocarbonyl include, but are not limited to, $CH_3$NHCO, $CH_3CH_2$NHCO, $CH_3CH_2CH_2$NHCO, $CH_3$CH($CH_3$)NHCO, and the like.

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The terms "comprise", "comprises", and "comprising" are to be interpreted inclusively rather than exclusively. The terms "consist", "consisting", and its variants, are to be interpreted exclusively, rather than inclusively.

As used herein, the term "about" means a variability of 10% from the reference given, unless otherwise specified.

Methods useful for making the compounds of formula (I) are set forth in the Examples below and generalized in Schemes 1-14. One of skill in the art will recognize that Schemes 1-14 can be adapted to produce the other compounds of formula (I) according to the present invention.

The following methods outline the synthesis of the compounds of formula (I). The following examples are presented to illustrate certain embodiments of the present invention, but should not be construed as limiting the scope of this invention.

Scheme A

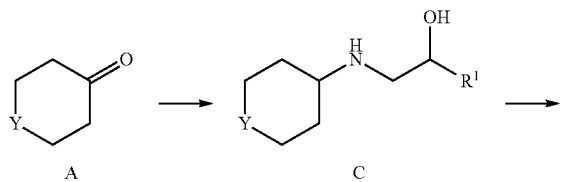

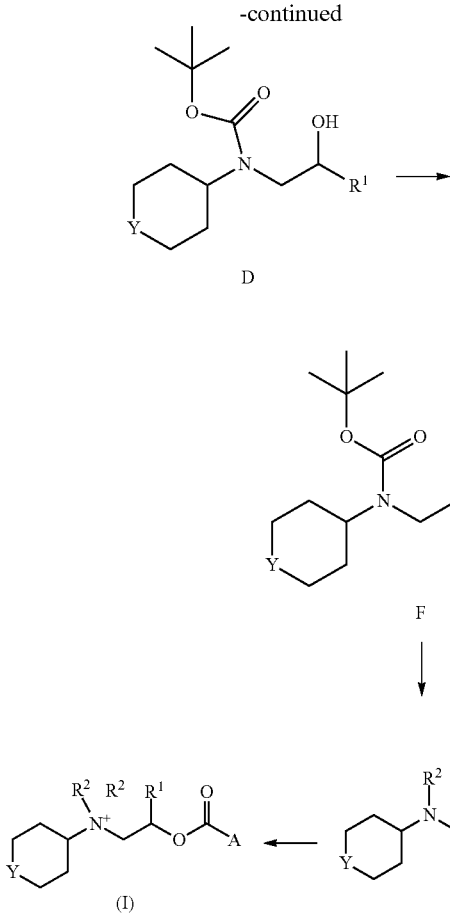

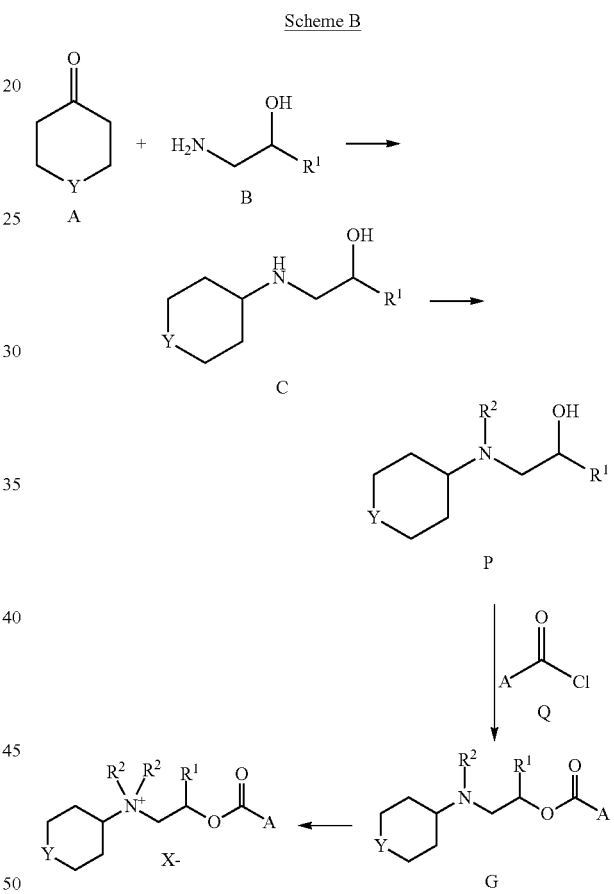

Scheme A describes one method for preparing the compounds of formula (I). In this method, cyclic ketone A is reacted with an $R^1$-substituted amino alcohol and sodium borohydride to provide compound C. In one embodiment, the $R^1$-substituted amino alcohol is $H_2NCH_2CH(OH)R^1$ (B). In another embodiment, the $R^1$-substituted amino alcohol is 1-amino-2-propanol. The nitrogen atom of compound C is then protected with a protecting group to provide compound D. In one embodiment, compound C is reacted with a Boc-anhydride. Compound D is then converted to ester compound F. In one embodiment, compound D is reacted with an acyl chloride. In a further embodiment, compound D is reacted with A-C(O)Cl (E). In one embodiment, the acylation may be done in the presence a base such as sodium hydride). In another embodiment, compound D is reacted with 2,4,6-trimethyl-benzoyl chloride. The nitrogen atom is then deprotected by treating with an acidic solution. The nitrogen is then $R^2$-substituted to provide compound G. In one embodiment, the nitrogen atom is deprotected with hydrochloric acid in dioxane and the $R^2$ substitution is performed by reacting the amine with a carbonyl compound and sodium triacetoxyborohydride. In another embodiment, the $R^2$ substitution is performed by reacting the amine with an alkyl halide, alkyl halide, mesylate, naphthalenesulfonate, benzenesulfonate, tosylate, camphorsulfonate or trifluoromethanesulfonate. In a further embodiment, the $R^2$-substitution is performed using ethyl iodide, ethyl bromide, or ethyl trifluoromethanesulfonate. Finally, the compound of formula (I) is formed by again $R^2$-substituting the nitrogen atom of compound G. In one embodiment, the $R^2$-substitution is performed using an alkyl halide, mesylate, naphthalenesulfonate, benzenesulfonate, tosylate, camphorsulfonate or trifluoromethanesulfonate. In another embodiment, the $R^2$-substitution is performed using methyl iodide, methyl bromide, methyl trifluoromethanesulfonate ethyl iodide, ethyl bromide or ethyl trifluoromethanesulfonate. In yet another embodiment, a trifluoromethanesulfonate salt is converted to a chloride salt by treatment with a chloride exchange resin such as Amberlite®IRA-400 chloride resin. In a further embodiment, the amine generated by deprotection of compound F is treated with a 1,4-dihaloalkane or 1,5-dihaloalkane, such as 1,4-dibromobutane or 1,5-dibromopentane, to generate the compound of formula (I) wherein the two $R^2$ groups are joined together to form a 5- or 6-membered ring.

Scheme B provides another route to the compound of formula (I). In this route, compound C is prepared using starting materials A and B as shown and described in Scheme A. Compound C may then be $R^2$-substituted at the nitrogen atom to provide compound P. This $R^2$-substitution may be performed using formaldehyde or other aldehyde compound, $Na(OAc)_3BH$ and acetic acid. Compound P may then be acylated. In one embodiment, the acylation may be performed using acylating agent A-C(O)Cl to provide compound G. In another embodiment, the acylation is performed in the presence of a base such as sodium hydride. In yet another embodiment, the acylation is performed using 2-isopropyl-benzoyl chloride. Finally, compound G is converted to the compound of formula (I) using the reagents and procedure described and shown in Scheme A.

Scheme C

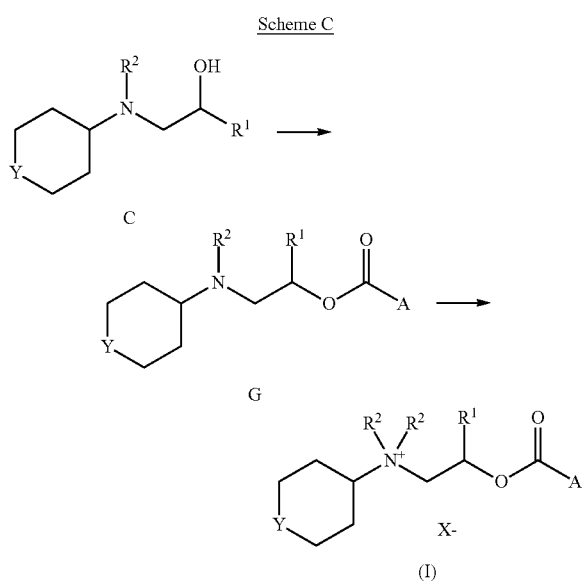

Compound G, an intermediate compound discussed in Schemes A and B, may be prepared from compound C as shown in Scheme C. In one embodiment, compound C is reacted with a mixed anhydride formed by treatment of a carboxylic acid with a chloroformate. In another embodiment, the mixed anhydride is prepared using 4-isopropylbenzoic acid and isobutyl-chloroformate. The successive $R^2$-substitution to compound G may then be performed as described above in Schemes A and B.

Pharmaceutical compositions of the invention comprise a compound of formula (I) optionally with other pharmaceutically inert or inactive ingredients. In one embodiment, the pharmaceutically inert or inactive ingredient is one or more pharmaceutically acceptable carrier or excipient. The present invention also contemplates combining the compound of formula (I) with one or more therapeutic agents, i.e., active ingredients, as described below. In a further embodiment, a compound of formula (I) is combined with one or more inert/inactive ingredients and one or more therapeutic agents.

The pharmaceutical compositions of the invention contain an amount of a compound of formula (I) that is effective for treating pain, itch, interstitial cystitis or overactive bladder in a subject. Specifically, the dosage of the compound of formula (I) to achieve a therapeutic effect will depend on factors such as the formulation, pharmacological potency of the drug, age, weight and sex of the patient, condition being treated, severity of the patient's symptoms, specific compound of formula (I), route of delivery, and response pattern of the patient. It is also contemplated that the treatment and dosage of the compound of formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. Further, one of skill in the art would be able to calculate any changes in effective amounts of any one of the compounds of the compositions due to changes in the composition components or dilutions. In one embodiment, the compositions may be diluted 2-fold. In another embodiment, the compositions may be diluted 4-fold. In a further embodiment, the compositions may be diluted 8-fold.

In one embodiment, the therapeutically effective amount is about 0.0001% to about 25% w/v. In another embodiment, the therapeutically effective amount is less than about 20% w/v, about 15% w/v, about 10% w/v, about 5% w/v, or about 1% w/v. In another embodiment, the therapeutically effective amount is about 0.0001% to about 10% w/v. In a further embodiment, the therapeutically effective amount is about 0.005 to about 5% w/v. In yet another embodiment, the therapeutically effective amount is about 0.01 to about 5% w/v. In still a further embodiment, the therapeutically effective amount is about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, or about 5% w/v. In one embodiment, the therapeutically effective amount of the compound of formula (I) is about 0.2% w/v. In another embodiment, the therapeutically effective amount is about 0.5% w/v.

The therapeutically effect amount of the compound of formula (I) may, therefore, be about 1 mg to about 1000 mg per dose based on a 70 kg mammalian subject. In another embodiment, the therapeutically effective amount is about 2 mg to about 250 mg per dose. In a further embodiment, the therapeutically effective amount is about 5 mg to about 100 mg. In yet a further embodiment, the therapeutically effective amount is about 25 mg to 50 mg, about 20 mg, about 15 mg, about 10 mg, about 5 mg, about 1 mg, about 0.1 mg, about 0.01 mg, about 0.001 mg.

The therapeutically effective amounts may be provided on regular schedule, i.e., on a daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy will be determined according to the judgment of a health-care practitioner. The therapeutically effective amounts described herein refer to total amounts administered for a given time period; that is, if more than one compound of formula (I) is administered, the therapeutically effective amounts correspond to the total amount administered.

The compound of formula (I) may be administered by any route, taking into consideration the specific condition for which it has been selected. The compounds of formula (I) may be delivered orally, by injection, inhalation (including orally, intranasally and intratracheally), ocularly, transdermally (via simple passive diffusion formulations or via facilitated delivery using, for example, iontophoresis, microporation with microneedles, radio-frequency ablation or the like), intravascularly, cutaneously, subcutaneously, intramuscularly, sublingually, intracranially, epidurally, rectally, intravesically, and vaginally, among others.

In one embodiment, the compound of formula (I) may be administered by injection, including microinjection, transdermally or topically. In one embodiment, the amount of the compound of formula (I) is about 0.05% w/w to about 10% w/w of the preparation depending on the route of administration. In one embodiment, the compound of formula (I) is present in a concentration of about 0.1% w/w to about 3% w/w. These compositions may also contain stabilizing agents, antibacterial agents, buffers and may be manufactured in different dosage unit ampoules or bottles. When for ocular use, the amount of the compound of formula (I) can be about 0.05% w/w to about 2.5% w/w. Compositions for injection or infusion may be prepared as an aqueous suspension or solution.

When used for dermal anesthesia, the amount of the compound of formula (I) can be about 0.1% w/w to about 10% w/w. When used for non-ocular, topical (e.g., oral, nasal, rectal, urethral, vaginal) administration the amount of the compound of formula (I) can be about 0.5% w/w to about 5% w/w. When used as in an injection, the amount of the compound of formula (I) can be about 0.25% w/w to about 3% w/w for injections. When used for infusions (e.g., for epidural, spinal or regional anesthesia), the amount of the compound of formula (I) can be about 0.1% w/w to about 3% w/w.

In one embodiment, the compound of formula (I) may be administered topically to the eye, e.g., as solutions, suspensions or ointments. Examples of ophthalmically compatible carriers which may be used include, without limitation, an aqueous solution, such as saline solution, oil solution or ointments containing ophthalmically compatible preservatives, surfactants, buffers, and viscosity regulators. These compositions may also contain stabilizing agents, antibacterial agents, and may be manufactured in different dosage units, suitable for ocular administration. Drug inserts, either soluble or insoluble, may also be used.

In another embodiment, the compound of formula (I) may be administered by injection. Solutions for injection or infusion may be prepared as aqueous solutions. Desirably, the compound of formula (I) is present in a concentration of about 0.1% w/w to about 3% w/w. These solutions may also contain stabilizing agents, antibacterial agents, buffers and may be manufactured in different dosage unit ampoules or bottles.

In a further embodiment, the compound of formula (I) may be administered rectally. Dosage units for rectal administration may be prepared in the form of ointments or suppositories, which contain the compound of formula (I) in a mixture with a neutral fat base, or they may be prepared in the form of gelatin-rectal capsules that contain the compound of formula (I) in a mixture with, e.g., a vegetable oil or paraffin oil. Ointments, suppositories or creams containing at least one compound of formula (I) are useful for the treatment of hemorrhoids.

In still another embodiment, the compound of formula (I) may be administered transdermally. A variety of transdermal delivery systems are known. For use in these systems, a compound of formula (I) may be admixed with a variety of excipients which may include, e.g., pH adjusters, preservatives, and/or penetration enhancers in order to form a solution, ointment, cream, lotion, or gel. Such a composition may form a constituent of a transdermal delivery system ("patch" etc.).

A transdermal delivery system may be selected which permits or assists a compound of the invention in passing though the dermal layer and to the targeted area, such as muscular tissues or a perineural space. Such systems may include formulation with skin penetration enhancers. Examples of skin penetration enhancers include physical enhancers (ultrasound, iontophoresis, electroporation, magnetophoresis, microneedle), vesicles, particulate systems (liposome, niosome, transfersome, microemulsion, solid lipid nanoparticle), and chemical enhancers (sulphoxides, azones, glycols, alkanols, terpenes, etc.). Further examples of chemical enhancers include, e.g., propylene glycol, polyethylene glycol, isopropanol, ethanol, oleic acid, N-methylpyrrolidone, which increase the permeability of the skin to the compounds, and permit the compounds to penetrate through the skin to deeper tissues. See, Sagie & Kohane, "Prolonged Sensory-Selective Nerve Blockade", PNAS, 2010(8): 3740-3745, 2010, which is herein incorporated by reference, for additional examples of chemical enhancers.

As a further embodiment, the compound of formula (I) may be instilled via direct instillation into the bladder and/or urothelium. In one example, a pharmaceutical composition containing a compound of formula (I) and one or more carriers or excipients is formulated for instillation. For example, the compound of formula (I) may be instilled as a solution. In a further example, the compound instilled may be placed into said bladder or urothelium as an extended-release formulation. A variety of extended-release formulations may be utilized for this purpose and include, without limitation, solution, suspension, gel or other solid dosage form containing reservoirs, a drug coated material, a drug impregnated material, a liposomal-drug formulation, among others.

The pharmaceutical compositions containing a compound of formula (I) may be formulated neat or with one or more pharmaceutical carriers and/or excipients for administration. The amount of the pharmaceutical carrier(s) is determined by the solubility and chemical nature of the compound of formula (I), chosen route of administration and standard pharmacological practice. The pharmaceutical carrier(s) may be solid or liquid and may incorporate both solid and liquid carriers/matrices. A variety of suitable liquid carriers is known and may be readily selected by one of skill in the art. Such carriers may include, e.g., di methylsulfoxide (DMSO), saline, buffered saline, cyclodextrin, hydroxypropylcyclodextrin (HPDCD), n-dodecyl-□-D-maltoside (DDM) and mixtures thereof. Similarly, a variety of solid (rigid or flexible) carriers and excipients are known to those of skill in the art. Such carriers may also be designed so as to undergo a state transition when injected into the bladder (e.g., liquid to gel, liquid to solid, gel to solid); such materials are known to those skilled in the art. Such carriers may also comprise a membrane, for example comprising a thermoelastic polymer, which defines a reservoir containing a solid or liquid composition. Such carriers may also comprise a thermoelastic polymer matrix, in which a composition which contains a compound of formula (I) is embedded.

The compounds of formula (I) can also be administered together with other-membrane stabilizers (local anesthetics), for example to form eutectic mixtures.

Although the compound of formula (I) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized, they are desirably sterile liquids. Liquid carriers are typically utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, lubricant, solubilizer, suspending agent, filler, glidant, compression aid, binder, disintegrant, or encapsulating material. In one embodiment, a solid carrier acts as a lubricant, solubilizer, suspending agent, binder, disintegrant, or encapsulating material. In another embodiment, the carrier comprises a thermoelastic polymer defining a reservoir containing at a minimum, at least one compound of formula (I) as a solid or liquid composition. In a further embodiment, such carriers comprise a thermoelastic polymer matrix, in which a composition described herein is embedded.

The composition may also be sub-divided to contain appropriate quantities of the compound of formula (I). For example, the unit dosage can be packaged compositions, e.g., packeted powders, vials, ampoules, prefilled syringes or sachets containing liquids.

In one embodiment, compositions described herein optionally contain one or more carriers and/or excipients, and one or more compounds of formula (I), optionally with a TRPV1 receptor activator. Examples of suitable excipients include without limitation, surfactants, adjuvants, antioxidants, binders, buffers, coatings, coloring agents, compression aids, diluents, disintegrants, emulsifiers (e.g., polyoxyethylene fatty acid esters), emollients, encapsulating materials, fillers, flavoring agents, glidants, granulating agents, lubricants, metal chelators, osmo-regulators, pH adjustors (e.g., sodium hydroxide), preservatives, solubilizers, sorbents, stabilizing agents, sweeteners (such as saccharin), surfactants, suspending agents, syrups, thickening agents (e.g., carboxypolymethylene or hydroxypropylmethylcellulose), penetration enhancers (e.g., hydroxypolyethoxydodecane, DMSO, DMAC, DDM, etc) or viscosity regulators (such as polymers to increase viscosity). See, for example, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a modified-release delivery device. "Modified-release" as used herein refers to delivery of a compound of formula (I) which is controlled, for example over a period of at least about 8 hours (e.g., extended delivery) to at least about 12 hours (e.g., sustained delivery). Such devices may also permit immediate release (e.g., therapeutic levels achieved in under about 1 hour, or in less than about 2 hours). Those of skill in the art know suitable modified-release delivery devices. For use in such modified-release delivery devices, the compound of formula (I) is formulated as described herein.

Suitable modified release delivery devices include drug-eluting implants. Such implants can comprise a thermoelastic polymer matrix, such as a silicon or ethylene vinyl acetate matrix, wherein one or more compounds of formula (I), optionally with one or more excipients, is embedded. See, e.g., U.S. Pat. No. 7,736,665 and US Patent Publication No. US-2011/0280922, the disclosures of which are herein incorporated by reference. Other drug-eluting implants can comprise an "osmotic pump" or other mechanism by which a solution comprising one or more compounds of formula (I) (optionally with one or more excipients) contained within the device is forced out, for example through the implant walls or through one or more apertures, by osmotic pressure which builds within the device once it is implanted into a subject. See, e.g., U.S. Pat. Nos. 5,035,891 and 6,464,688, the disclosures of which are herein incorporated by reference. Still other drug-eluting implants can comprise a hydrogel such as a polymethacrylate-based polymer (see, e.g., U.S. Pat. Nos. 5,292,515 and 5,266,325, the disclosures of which are herein incorporated by reference), or a thermoelastic polymer, such as a polyurethane (see, e.g., U.S. Pat. Nos. 7,858,110 and 7,842,303, the disclosures of which are herein incorporated by reference), which define a reservoir containing a solid or liquid composition comprising one or more compounds of formula (I) optionally with one or more excipients. Still other drug-eluting implants can comprise a bio-degradable or bio-erodable polymer and at least one or more compounds of formula (I), optionally with one or more excipients. See, e.g., U.S. Pat. Nos. 4,906,474 and 5,633,002, the disclosures of which are herein incorporated by reference.

Modified release of the compounds of formula (I) may also be achieved by injecting a composition comprising one or more of these compounds into the bladder tissue (e.g., into the urothelium or muscularis propria) with a device that can be employed via an endoscope inserted into the bladder or percutaneously. For example, one or more compounds of formula (I) can be injected into the bladder tissue via a needle, or a needleless device as described in US Patent Publication No. US-2011/0046600, the disclosure of which is incorporated by reference. A suitable needleless injection device includes the JetTouch™ platform (American Medical Systems; Minnetonka, Minn.). The injected compounds can form a depot, and in certain embodiments, the one or more compounds of formula (I) can be encapsulated in a bio-degradable or bio-erodable polymer, for example as described in U.S. Pat. Nos. 5,480,656 and 6,036,976, the disclosures of which are incorporated by reference.

Modified release of the compounds of formula (I) may also be achieved by instilling a composition comprising one or more compounds of formula (I) and a material which solidifies or gels, for example once instilled into the bladder or upon contact with the bladder urothelium, to coat at least a portion of the bladder wall. The one or more compounds of formula (I) can then elute from the solidified or gelled material. See, e.g., U.S. Pat. Nos. 6,894,071; 5,575,815 and 6,039,967, the disclosures of which are incorporated by reference.

In still a further embodiment, the compositions may be administered transdermally, via the use of a drug-eluting patch. In one embodiment, the patch is an "iontophoretic" transdermal patch in which one or more medication(s) is delivered using a simple or more sophisticated (e.g., microprocessor-controlled) electrical current using, for example, an on-board battery. In still a further embodiment, the patch is a "microneedle" transdermal patch which contains microneedles coated with or containing (in dissolvable or non-dissolvable form) a pharmaceutical composition of the invention. See, e.g., U.S. Pat. Nos. 7,798,987 and 7,537,795, the disclosures of which are herein incorporated by reference. The microneedles can themselves be dissolvable or non-dissolvable; see, for example, the "microneedle" technology described in Sullivan et al., "Dissolving Polymer Microneedle Patches for Influenza Vaccination", Nature Medicine, 16:915-920 (Jul. 18, 2010 online publication) and Lee et al., "Dissolving Microneedle Patch for Transdermal Delivery of Human Growth Hormone", Small, Jan. 4, 2011 online publication, which are herein incorporated by reference. Other suitable transdermal delivery systems include the radio-frequency ablations systems described in Sintov et al., "Radiofrequency-Driven Skin Microchanneling as a New Way for Electrically Assisted Transdermal Delivery of Hydrophilic Drugs", Controlled Release 89: 311-320 (2003), and U.S. Pat. No. 7,558,625, the disclosures of which are herein incorporated by reference.

Further examples of transdermal patches useful for administration of the compounds of formula (I) include those described in U.S. Pat. Nos. 5,411,738 and 5,827,528 and Prausnitz and Langer, "Transdermal drug delivery", Nature Biotechnology, 26(11):1261-1268, November 2006, which are herein incorporated by reference. Desirably, a patch is applied via a suitable adhesive on the skin, where it remains in place for at least one hour. In one embodiment, the patch remains in place for about 1 hour and is replaced weekly, for a total of about 2 or about 3 hours wear time. In another embodiment, the patch remains in place for about 2 hours. In a further embodiment, the patch remains in place for about 3 hours. In still another embodiment, the patch remains in place for about 4 hours. In yet another embodiment, the patch remains in place for longer or shorter periods of time.

Also contemplated is the administration of the compounds of formula (I) with other medication(s) or therapeutic agent(s). In one embodiment, the compounds of formula (I) are combined with other medications or therapeutic agents in a single composition. However, the present invention is not so limited. In other embodiments, the compounds of formula (I) may be administered in one or more separate formulations from other compounds of formula (I), or other medications or therapeutic agents as described below.

In one embodiment, the compounds of the invention may be utilized for treating pain or itch when combined a TRPV1 receptor activator. The term "TRPV1 receptor activator" as used herein refers to any agent or stimulus that activates TRPV1 receptors on nociceptors or pruriceptors and allows for entry of at least one inhibitor of voltage-gated ion (e.g., sodium or calcium) channels. In one embodiment, the TRPV1 receptor activator includes, but is not limited to, capsaicin, dihydrocapsaicin and nordihydrocapsaicin, lidocaine, articaine, procaine, tetracaine, mepivicaine, bupivicaine, eugenol, camphor, clotrimazole, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), Cl 8 N-acylethanolamines, lipoxygenase derivatives (such as 12-hydroperoxyeicosatetraenoic acid), inhibitor cysteine knot (ICK) peptides (vanillotoxins), MSKI 95 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl) thiourea), hydroxy-α-sanshool, 2-aminoethoxydiphenyl borate, 10-shogaol, oleylgingerol, oleylshogaol, SU200 (N-(4-tert-butylbenzyl)-N'-(4-hydroxy-3-methoxybenzyl)thiourea) nonivamide, and fatty acyl amides of tetrahydroisoquinolines. In another embodiment, the TRPV1 receptor activator is lidocaine, aprindine, benzocaine, butacaine, cocaine, dibucaine, encamide, mexiletine, oxetacaine (oxethazaine), prilocaine, proparacaine, procainamide, n-acetylprocainamide, chloroprocaine (nesacaine, nescaine), dyclonine, etidocaine, levobupivacaine, ropivacaine, cyclomethycaine, dimethocaine (larocaine), propoxycaine, trimecaine, and sympocaine. In a further embodiment, the TRPV1 receptor activator is lidocaine. In another embodiment, the TRPV1 activator may be a detergent or a surfactant, examples of which may be found in commonly-used hygiene products such as soaps and shampoos (e.g., sodium lauryl sulfate). See, Lilja et al. "Surfactant-Induced TRPV1 activity—A Novel Mechanism for Eye Irritation?" Technological Sciences, 99(1):174-180, 2007, which is incorporated herein by reference. In another embodiment, the TRPV1 receptor activator is heat or inflammation.

In one embodiment, the therapeutically effective amount of the TRPV1 receptor activator is about 0.0001% to about 10% w/v. One of skill in the art would readily understand that the recited therapeutically effective amount is based on the free base of the TRPV1 receptor activator. By using this information and skill in the art, one would be able to determine the amount of the corresponding TRPV1 receptor activator salt for use in the compositions and methods described herein. In another embodiment, the therapeutically effective amount is less than about 10% w/v, about 9% w/v, about 8% w/v, about 7% w/v, about 6% w/v, about 5% w/v, about 4% w/v, about 3% w/v, about 2% w/v, or about 1% w/v. In another embodiment, the therapeutically effective amount is about 0.1% to about 5% w/v. In a further embodiment, the therapeutically effective amount is about 0.5 to about 3% w/v. In yet another embodiment, the therapeutically effective amount is about 0.5 to about 2% w/v. In another embodiment, the therapeutically effective amount of a TRPV1 receptor activator is about 2% w/v. In another embodiment, the therapeutically effective amount is about 1% w/v. In a further embodiment, the therapeutically effective amount is about 0.5% w/v.

The therapeutically effect amount of the TRPV1 receptor activator may, therefore, be about 0.001 mg to about 100 mg per dose based on a 70 kg mammalian subject. In another embodiment, the therapeutically effective amount is about 0.1 mg to about 25 mg per dose. In a further embodiment, the therapeutically effective amount is about 1 mg to about 5 mg. In yet a further embodiment, the therapeutically effective amount is about 0.1 mg, about 0.5 mg, about 1 mg, about 2 mg, about 3 mg, about 4 mg, about 5 mg, about 6 mg, about 7 mg, or about 8 mg.

The present invention, therefore, provides a composition containing a compound of formula (I) and lidocaine. In one embodiment, the composition contains about 0.01% to about 1% w/v of a compound of formula (I) and about 0.1% to about 5% w/v of lidocaine. In another embodiment, the composition contains about 0.1% to about 0.7% w/v of a compound of formula (I) and about 1% to about 3% w/v of lidocaine. In a further embodiment, the composition contains about 0.2% to about 0.5% w/v of a compound of formula (I) and about 1% to about 3% w/v of lidocaine. In yet another embodiment, the composition contains about 0.2% to about 0.5% w/v of a compound of formula (I) and about 2% w/v of lidocaine. In still another embodiment, the composition contains about 0.2% w/v of a compound of formula (I) and about 2% w/v of lidocaine. In another embodiment, the composition contains about 0.5% w/v of a compound of formula (I) and about 2% w/v of lidocaine. As discussed above, these compositions may be further diluted. In one embodiment, these compositions may be diluted 2-fold. In another embodiment, these compositions may be diluted 4-fold.

Also contemplated for use in the pharmaceutical combinations and methods described below are inhibitors of voltage-gated ion channels. In one embodiment, the voltage-gated ion channels are sodium or calcium ion channels. In a further embodiment, the voltage-gated sodium channel inhibitor includes, without limitation, QX-314, N-methyl-procaine (QX-222), N-octyl-guanidine, 9-aminoacridine, and pancuronium. In another embodiment, the inhibitor of voltage-gated calcium channels includes, but is not limited to, D-890 (quaternary methoxyverapamil) and CERM 1 1888 (quaternary bepridil). In a further embodiment, voltage-gated ion channel inhibitors such as riluzole, mexilitine, phenyloin, carbamazepine, procaine, tocamide, prilocaine, diisopyramide, bencyclane, quinidine, bretylium, lifarizine, lamotrigine, flunarizine, articaine, bupivicaine, mepivicaine, fluspirilene, orphenadrine, phenbenzamine, bepridil, pimozide, penfluridol, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine may be combined with the compound of formula (I).

Membrane permeable inhibitors of voltage-gated ion channels may also be utilized in combination with the compound of formula (I) in the compositions, combinations, or methods described herein. In one embodiment, the membrane permeable inhibitor of voltage-gated ion channels includes, but is not limited to, cocaine, carbamazepine, disopyramide, lamotrigine, procainamide, phenyloin, oxcarbazepine, topiramate, zonisamide, tetracaine, ethyl aminobenzoate, prilocaine, disopyramide phosphate, flecamide acetate, mexiletine, propafenone, quinidine gluconate, quinidine polygalacturonate, chloroprocaine, dibucaine, dyclonine, mepivacaine, pramoxine, procaine, tetracaine, oxethazaine, propitocaine, levobupivacaine, bupivacaine, lidocaine, moricizine, tocamide, proparacaine, ropivacaine, quinidine sulfate, encamide, ropivacaine, etidocaine, moricizine, quinidine, encamide, flecamide, tocamide, fosphenyloin, chloroprocaine, dyclonine, L-(−)-l-butyl-2',6'-pipecoloxylidide, and pramoxine.

Additionally, one or more agents typically used to treat pain, i.e., analgesics, may be used in conjunction with a combination of the invention in the methods, compositions, and kits described herein. Such agents include, but are not limited to, non-steroidal anti-inflammatory drugs (NSAIDs), opioids, tricyclic antidepressants, amine transporter inhibitors, and anticonvulsants (such as gabapentinoids).

The compound of formula (I) may be administered together with a vasoconstrictor (e.g., epinephrine or vasopressin) when utilized in injectable solutions.

The compound of formula (I) may be combined with glucose or dextrose when utilized for infusion or as a regional analgesic or anti-pruritic.

Further, the compound of formula (I) may be combined with thickening agents to form a jelly, or may also contain penetration enhancers, for use in topical or dermal applications such as for urogenital topical procedures.

Sprays for topical anesthesia of the mouth and oropharynx may contain the compound of formula (I), saccharin and/or alcohol.

Finally, the compound of formula (I) may be formulated as an ointment for administration to accessible mucous membranes.

One or more additional agents typically used to treat itch may be used in conjunction with a combination of the invention in the methods, compositions, and kits described herein. Such agents include topical or oral steroids and antihistamines.

Additionally, one or more agents typically used to treat interstitial cystitis or overactive bladder may be used in conjunction with a combination of the invention in the methods, compositions, and kits described herein. In one embodiment, the additional agent utilized to treat overactive bladder may be an anticholinergic, e.g., Darifenacin (Enablex® drug), Fesoterodine (Toviaz® drug), Oxybutynin (Ditropan®, Ditropan XL®, Oxytrol®, Gelnique® drugs), Solifenacin (Vesicare® drug), Tolterodine (Detrol® and Detrol® LA drugs), and/or Trospium (Sanctura® drug), an antidepressant, e.g., the tricyclic antidepressant imipramine hydrochloride (Tofranil® drug), botulinum toxin, more commonly known for removing wrinkles, estrogen, an $\alpha$-blocker, capsaicin, and/or resiniferatoxin.

In another embodiment, the additional agent utilized to treat interstitial cystitis may be a non-steroidal anti-inflammatory drug, e.g., ibuprofen (Advil® or Motrin® drugs), naproxen (Aleve® or Anaprox® drugs), an antidepressant such as a tricyclic antidepressant, e.g., amitriptyline or imipramine (Tofranil® drug), an antihistamine, e.g., diphenhydramine (Benadryl® drug) and loratadine (Claritin® drug), pentosan (Elmiron® drug), among others. The additional agent may, alternatively, be selected from among DMSO (Rimso-50® drug), lidocaine, sodium bicarbonate, pentosan, heparin, hyaluronan, chondroitin sulfate and oxybutynin, or combinations thereof.

Also provided herein are regimens, kits or packages of pharmaceutical formulations containing the compounds of formula (I) or compositions described herein. The kits may be organized to indicate a single formulation or combination of formulations to be taken at each desired time.

Suitably, the kit contains packaging or a container with the compound of formula (I) formulated for the desired delivery route. Suitably, the kit contains instructions on dosing and an insert regarding the compound of formula (I). Optionally, the kit may further contain instructions for monitoring local or circulating levels of product and materials for performing such assays including, e.g., reagents, well plates, containers, markers or labels, and the like. Such kits are readily packaged in a manner suitable for treatment of a desired indication. For example, the kit may also contain instructions for use of a patch, spray pump or other delivery device. Other suitable components to include in such kits will be readily apparent to one of skill in the art, taking into consideration the desired indication and the delivery route and may contain lubricants, antiseptic solutions and local anesthetic agents to facilitate the placement of the delivery device.

The compounds of formula (I) or compositions described herein can be a single dose or for continuous or periodic discontinuous administration. For continuous administration, a package or kit can include the compound of formula (I) in each dosage unit (e.g., solution, lotion, tablet, pill, drug-eluting unit/patch or other unit described above or utilized in drug delivery), and optionally instructions for administering the doses less-than-daily, daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a foil or blister package, labeled ampoule, vial or bottle.

The packaging means of a kit may itself be geared for administration, such as an inhaler, syringe, pipette, eye dropper, catheter, cytoscope, trocar, cannula, pressure ejection device, or other such apparatus, from which the formulation may be applied to an affected area of the body, such as the lungs, injected into a subject, delivered to bladder tissue or even applied to and mixed with the other components of the kit.

One or more components of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials or other suitable packaging means in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhaler, syringe, pipette, forceps, measuring spoon, eye dropper, catheter, cytoscope, trocar, cannula, pressure-delivery device or any such medically approved delivery means.

In one embodiment, a kit is provided and contains a compound of formula (I). The compound of formula (I) may be in the presence or absence of one or more of the carriers or excipients described above. The kit may optionally contain instructions for administering the compound of formula (I) to a subject having pain, itching, interstitial cystitis or overactive bladder.

In a further embodiment, a kit is provided and contains a compound of formula (I) in a second dosage unit, and one or more of the carriers or excipients described above in a third dosage unit. The kit may optionally contain instructions for administering the compound of formula (I) to a subject having pain, itching, interstitial cystitis or overactive bladder.

When utilized as described herein, the TRPV1 receptor activator may be utilized in amounts greater or less than the compound of formula (I). In one embodiment, the ratio of the compound of formula (I) to the TRPV1 receptor activator may be determined by the attending physician. In one embodiment, an about 1:1 ratio of the compound of formula (I) to the TRPV1 receptor activator is utilized. In another embodiment, greater than or least about a 1:1 ratio of the compound of formula (I) to the TRPV1 receptor activator is utilized. In a further embodiment, less than a 1:1 ratio of the compound of formula (I) to the TRPV1 receptor activator is utilized. In still a further embodiment, the ratio of the compound of formula (I) to the TRPV1 receptor activator is about 1:0.5. In yet another embodiment, the ratio of the compound of formula (I) to the TRPV1 receptor activator is at least about 1:2. In still another embodiment, the ratio of the compound of formula (I) to the TRPV1 receptor activator is about 1:2. In yet a further embodiment, the ratio of the compound of formula (I) to the TRPV1 receptor activator is about 1:3. In another embodiment, the ratio of the compound of formula (I) to the TRPV1 receptor activator is about 1:4. In yet another embodiment, the ratio of the compound of formula (I) to the TRPV1 receptor activator is about 1:5. In a further embodiment, the ratio of the compound of formula (I) to the TRPV1 receptor activator is about 1:7. In yet another embodiment, the ratio of the compound of formula (I) to the TRPV1 receptor activator is about 1:10. In another embodiment, the ratio of the compound of formula (I) to the TRPV1 receptor activator is about 1:25 or lower. In still a further embodiment, the ratio of the compound of formula (I) to the TRPV1 receptor activator is about 1:0.5 to about 1:25.

The compound of formula (I) may also be administered in prior to, concurrently with, or subsequent to non-medication related therapies. In one embodiment, the compounds of formula (I) may be administered in conjunction with nerve stimulation, e.g., transcutaneous electrical nerve stimulation (TENS) or sacral nerve stimulation.

In a further embodiment, the compounds described herein may be used for the manufacture of a medicament for treating overactive bladder and/or interstitial cystitis.

As discussed above, the methods, compositions, and kits of the invention can be used to treat pain, itch, interstitial cystitis or overactive bladder resulting from a number of conditions. The term "pain" as used herein includes all types of pain. In one embodiment, the pain may be acute or chronic. In another embodiment, the pain may be nociceptive, dysfunctional, idiopathic, neuropathic, somatic, visceral, inflammatory, and/or procedural. For example, the pain may be from a migraine, back pain, neck pain, gynecological pain, pre-labor or labor pain, orthopedic pain, post-stroke pain, post-surgical or procedural pain, post herpetic neuralgia, sickle cell crises, interstitial cystitis, urological pain (such as urethritis), dental pain, headache, pain from a wound or from a medical procedure such as surgery (such as bunionectomy or hip, knee or other joint replacement), suturing, setting a fracture, biopsy, and the like. Pain may also occur in patients with cancer, which may be due to multiple causes, such as inflammation, nerve compression, and mechanical forces resulting from tissue distension as a consequence of invasion by a tumor and tumor metastasis into bone or other tissues.

In one embodiment, the pain is neuropathic pain, such as post-herpetic neuralgia. In another embodiment, the pain is inflammatory pain. In a further embodiment, the pain is nociceptive pain. In still another embodiment, the pain is procedural pain. In yet a further embodiment, the pain is caused by esophageal cancer, colitis, cystitis, irritable bowel syndrome, colitis or idiopathic neuropathy.

"Somatic pain" includes pain from bone, joint, muscle, skin, or connective tissue.

"Central pain" includes pain arising as a consequence of brain trauma, stroke, or spinal cord injury.

"Visceral pain" includes pain from visceral organs, such as the respiratory or gastrointestinal tract and pancreas, the urinary tract and reproductive organs. In one embodiment, visceral pain results from tumor involvement of the organ capsule. In another embodiment, visceral pain results from obstruction of hollow viscus. In a further embodiment, visceral pain results from inflammation as in cystitis or reflux esophagitis.

"Idiopathic pain" refers to pain which has no underlying cause or refers to pain caused by condition which remains undiagnosed.

"Dysfunctional pain" refers to pain which occurs in the absence of a noxious stimulus, tissue damage or a lesion to the nervous system. In one embodiment, dysfunctional pain results from rheumatologic conditions such as arthritis and fibromyalgia, tension type headache, irritable bowel disorders and erythermalgia.

"Nociceptive pain" includes pain caused by noxious stimuli that threaten to or actually injure body tissues. In one embodiment, nociceptive pain results from a cut, bruise, bone fracture, crush injury, burn, trauma, surgery, labor, sprain, bump, injection, dental procedure, skin biopsy, or obstruction. In another embodiment, nociceptive pain is located in the skin, musculoskeletal system, or internal organs.

"Neuropathic pain" is pain due to abnormal processing of sensory input by the peripheral or central nervous system consequent on a lesion to these systems. In one embodiment, neuropathic pain is chronic and non-malignant. In one embodiment, neuropathic pain is due to trauma, surgery, herniation of an intervertebral disk, spinal cord injury, diabetes, infection with herpes zoster (shingles), HIV/AIDS, late-stage cancer, amputation (such as mastectomy), carpal tunnel syndrome, chronic alcohol use, exposure to radiation, and as an unintended side-effect of neurotoxic treatment agents, such as certain anti-HIV and chemotherapeutic drugs. In another embodiment, neuropathic pain is may be described as "burning," "electric," "tingling," or "shooting".

The phrase "inflammatory pain" includes pain resulting from inflammation caused by any number of factors. In one embodiment, inflammatory pain occurs due to tissue damage or inflammation. In another embodiment, inflammatory pain is due to injury (including joints, muscle, and tendons injuries), surgical procedures, infection, and/or arthritis.

"Procedural pain" includes refers to pain arising from a medical procedure. The medical procedure may include any type of medical, dental or surgical procedure. In one embodiment, the procedural pain is postoperative. In another embodiment, the pain is associated with an injection, draining an abscess, surgery, dermatological, dental procedure, ophthalmic procedure, arthroscopy and use of other medical instrumentation, and/or cosmetic surgery.

A "migraine" is a headache due to activation of sensory fibers innervating the meninges of the brain.

The term "itch" refers to all types of itching and stinging sensations that may be localized or generalized, and may be acute, intermittent or persistent. The itch may be idiopathic, allergic, metabolic, infectious, drug-induced, or due to specific disease states due to liver or kidney disease, or cancer. "Pruritus" is severe itching, but as used herein can include "itch" as defined above. In one embodiment, the itching may result from stress, anxiety, UV radiation, metabolic and endocrine disorders (e.g., liver or kidney disease, hyperthyroidism), cancer, drug reactions, reactions to food, parasitic infections, fungal infections, allergic reactions, diseases of the blood (e.g., polycythemia vera), insect bites, pregnancy, metabolic disorders, liver or renal failure, eczema, and dermatological conditions such as dermatitis, eczema, or psoriasis.

The term "treat", "treating", or any variation thereof is meant to include therapy utilized to remedy a health problem or condition in a patient or subject. In one embodiment, the health problem or condition may be eliminated permanently or for a short period of time. In another embodiment, the severity of the health problem or condition, or of one or more symptoms characteristic of the health problem or condition, may be lessened permanently, or for a short period of time. The effectiveness of a treatment of pain, itch, IC or OAB can be determined using any standard pain or itch index, such as those described herein, or can be determined based on the patient's subjective pain, itch assessment, or sensory symptoms associated with IC or OAB, including the feeling of urgency associated therewith. A patient is considered "treated" if there is a reported reduction in pain, itch, reduction in the sensory nervous symptoms associated with OAB or IC, or a reduced reaction to stimuli that should cause pain or itch. In one embodiment, the compounds of formula (I) are useful for treating interstitial cystitis or overactive bladder, as these compounds may selectively modulate the nervous system affecting sensory aspects of OAB and IC without affecting or negatively impacting motor neuron function associated with bladder and sphincter control.

In order to measure the efficacy of any of the methods, compositions, or kits described herein, a measurement index may be used. Indices that are useful for the measurement of pain associated with musculoskeletal, immunoinflammatory and neuropathic disorders include a visual analog scale (VAS), a Likert scale, categorical pain scales, descriptors, the Lequesne index, the WOMAC index, and the AUSCAN index, each of which is well known in the art. Such indices may be used to measure pain, itch, function, stiffness, or other variables. Indices that are useful for the measurement of overactive bladder are known in the art and include patient-reported outcome devices or notebooks and urodynamic measurements of urinary incontinence such as the measurement of micturition volume using condom catheters and other physical collection devices.

Indices that are useful of the measurement of the pain associated with interstitial cystitis include the interstitial cystitis symptom index (ICSI), the interstitial cystitis problem index (ICPI), the pain-urgency-frequency score (PUF), the Wisconsin Symptom Instrument (UWI) and a visual analog scale (VAS) such as the Likert scale and other categorical pain scales.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain or itch by choosing the spot on the line that best corresponds to the sensation of pain or itch, where one end of the line corresponds to "no pain" (score of 0 cm) or "no itch" and the other end of the line corresponds to "unbearable pain" or "unbearable itch" (score of 10 cm). This procedure provides a simple and rapid approach to obtaining quantitative information about how the patient is experiencing pain or itch. VAS scales and their use are described, e.g., in U.S. Pat. Nos. 6,709,406 and 6,432,937, the relevant disclosures of which are herein incorporated by reference.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced. Likert scales and their use are described, e.g., in U.S. Pat. Nos. 6,623,040 and 6,766,319, the relevant disclosures of which are herein incorporated by reference.

The Lequesne index and the Western Ontario and McMaster Universities (WOMAC) osteoarthritis (OA) index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert scale. Both the WOMAC index and the Lequesne index questionnaires have been extensively validated in OA, including in surgical settings (e.g., knee and hip arthroplasty). Their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index may utilize, e.g., a Likert or a VAS scale.

The O'Leary-Sant score and IC Problem Index are self-administered indices for measuring lower urinary tract symptoms.

The Pain-Urgency-Frequency symptom scale is balanced assessment of urinary dysfunction, pelvic pain and symptoms associated with sexual intercourse and frequently used in conjunction with intravesical potassium chloride administration.

The UWI utilizes seven IC-related questions about frequency, urgency, noctuira and pain.

Other suitable indices that are useful for the measurement of pain include the Pain Descriptor Scale (PDS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

Itch can also be measured by subjective measures known to those skilled in the art (VAS, Likert, descriptors and the like). Another approach is to measure scratch which is an objective correlate of itch using a vibration transducer or movement-sensitive meters.

In one embodiment, the treatment methods described herein include administering a compound of formula (I) to a patient. Additional, optional agents, such as those described above for use in the combination, may be administered to the patient prior to, concurrently with, or subsequent to the compound of formula (I).

In another embodiment, the methods described herein thereby include administering a compound of formula (I) and a TRPV1 receptor activator to a patient. In one embodiment, the compound of formula (I) is administered to the patient prior to the TRPV1 receptor activator. In another embodiment, the TRPV1 receptor activator is administered to the patient prior to the compound of formula (I). In a further embodiment, the compound of formula (I) and TRPV1 receptor activator are administered to the patient concurrently.

Also contemplated by the present invention is administration of a compound of formula (I) after the TRPV1 receptor has been activated. Specifically, this method is performed after the TRPV1 receptor is activated. Such activation may result from administration of an exogenous activating compound or stimulus, or may arise as a result of endogenous activation induced by a pathophysiological state, such as inflammation, that activates TRPV1 receptors.

A variety of in vivo assays and animal models are useful for assessing the ability of compounds to inhibit pain via internal sodium channel inhibition. These models may or may not involve opening (activation) of TRPV1 channels via inducing pain through physical, mechanical, or chemical (e.g., capsaicin) means. Examples of suitable models include, e.g., those described in A M Binshtok et al, Anesthesiology, July 2009, 111(1):127-137; C R Reis et al., Anesthesiology, July 2009, 111(1):122-126; P Gerner et al., Anesthesiology, November 2008, 109(5):872-878; and A M Binshtok et al., Nature, October 2007, 449:607-610, the use of isolated bladder detrusor muscle preparations (Witte, Naunyn-Schmeideberg's Arch. Pharmacol. 2011, 384:555-563), measurement of voiding frequency and volume in freely moving animals (Clouse, 2012, Urology 79:1410e1-1410e6), measurement of bladder urodynamics using cystometry in anesthetized animals (Shimizu, 2000, British Journal of Pharmacology 131:610-616), which are incorporated by reference herein. However, for a variety of reasons which will be readily apparent to those of ordinary skill in the art, it is desirable to provide in vitro assays which allow for the identification of compounds with the desired properties. Described herein are several such in vitro assays.

In one embodiment, a modified FLIPR® (Fluorometric Imaging Plate Reader) based assay system was developed which is capable of discriminating between non-specific versus hTRPV1-mediated entry of test compounds. Advantageously, the assay system utilizes heat activated opening of hTRPV1 channels followed by an assessment of internal sodium channel block. The assay allows a permanently charged compound to selectively enter through opened hTRPV1 channels and that compound's potency in inhibiting sodium channels from the cytoplasm side of the same cell can be assessed and quantified.

The modified FLIPR® assay utilizes cells which functionally express hTRPV1. As used herein, the term "functionally express" includes those cells which express the human TRPV1 protein and which respond to stimuli which naturally open this channel, including, e.g., the thermal (e.g., heat) or chemical (e.g., capsaicin, lidocaine) means described herein. Suitable assays may include the calcium or membrane potential assays described herein (see, e.g., Example 49). However, other functional assays are known in the art (e.g. voltage-clamp electrophysiology such as used by Binshtok et al., Nature 449(4) 607-610, 2007).

A suitable cell may be selected for expression of TRPV1 in cis or in trans and constructed using known techniques. In one embodiment, a neuroblastoma cell line such as N1E115 [CRL-2263] or ND7/23 [ECACC catalog code: 92090903] is selected for expression of the hTRPV1. However, another neuroblastoma cell line may be selected, e.g., such as IMR-32 [CRL-127]; Neuro-2a [CRL-131]; NB41A3 [CRL-147]; B104-1-1 [CRL-1887]; SK-N-AS [CRL-2137]; SK-N-F1 [CRL-2142]; SK-N-DZ [CRL-2149]; SH-SY5Y [CRL-2266]; BE(2)-M17 [CRL-2267]; BE(2)-C [CRL-2268]; MC-IXC [CRL-2270]; SK-N-BE(2) (CRL-2271); CHP-212 (CRL-2273]; B35 [CRL-2754], which are available from the American Type Culture Collection, Manassas, Va. (US). Still other cell lines may be selected.

For a generation description of how the cells are produced, see generally, e.g., Sambrook et al, Molecular Cloning: A Laboratory Manual, Cold Spring Harbor Press, Cold Spring Harbor, N.Y. (US) 2001. In one embodiment, a stable cell line may be prepared using the techniques in Sambrook et al, using wild-type (wt) or recombinant hTRPV1 coding sequences. For example, preparation of one such cell line is described in detail herein (see Example 32). Preparation of another cell line is described in International Patent Publication No. WO 2007/0066068; the Lipofectamine® method may be employed for transfection of TRPV1 and hTRPV1 into Human Embryonic Kidney cells (HEK293) according to the manufacturers protocol (Gibco). To create a permanently expressing cell line, wt-TRPV1 transfected HEK cells can be subcloned in geneticin (0.6 mg/mL) containing medium (DMEM containing 10% FCS, 100 U/mL penicillin, 100 µg/mL streptomycin, and 250 ng/mL amphotericin B) and propagated for two weeks to allow selection. To obtain a TRPV1 permanently expressing single cell line, transfected cells can be plated in 96 well plates (1 cell per well) and colonies grown from single cells were subsequently tested for capsaicin responsiveness by measuring increases in intracellular calcium. The final clones selected, are taken through three further rounds of single cell cloning to ensure the cell lines are derived from a single cell. Variations on this methodology will be readily apparent to one of skill in the art. In another embodiment, cells may be selected from a stable cell line to express the hTRPV1, in trans, e.g., from a viral vector or another suitable genetic element.

In one embodiment, the hTRPV1 protein is selected which has the sequence of SEQ ID NO:1: [NCBI Accession Number NM_080706.3].

While the use of cells which are infected or transfected such that they express hTRPV1 in trans is possible, the use of a cell line which stably expresses the hTRPV1 channel is desirable. Such cell lines can be generated by one of skill in the art utilizing the information available herein and known in the art.

In one embodiment, in order to prepare the cell line, hTRPV1 is amplified by PCR from IMR322 cDNA (a neuroblastoma cell line). The PCR product obtained containing the protein coding sequence of hTRPV1 is cloned into a production vector under the control of a strong promoter. As illustrated below, the human cytomegalovirus promoter was used. However, another promoter with strong constitutive expression in mammalian host cells may also be used. Optionally, the sequence may be verified by PCR. The cells

```
  1 MKKWSSTDLG AAADPLQKDT CPDPLDGDPN SRPPPAKPQL STAKSRTRLF GKGDSEEAFP

61 VDCPHEEGEL DSCPTITVSP VITIQRPGDG PTGARLLSQD SVAASTEKTL RLYDRRSIFE

121 AVAQNNCQDL ESLLLFLQKS KKHLTDNEFK DPETGKTCLL KAMLNLHDGQ NTTIPLLLEI

181 ARQTDSLKEL VNASYTDSYY KGQTALHIAI ERRNMALVTL LVENGADVQA AAHGDFFKKT

241 KGRPGFYFGE LPLSLAACTN QLGIVKFLLQ NSWQTADISA RDSVGNTVLH ALVEVADNTA

301 DNTKFVTSMY NEILMLGAKL HPTLKLEELT NKKGMTPLAL AAGTGKIGVL AYILQREIQE

361 PECRHLSRKF TEWAYGPVHS SLYDLSCIDT CEKNSVLEVI AYSSSETPNR HDMLLVEPLN

421 RLLQDKWDRF VKRIFYFNFL VYCLYMIIFT MAAYYRPVDG LPPFKMEKTG DYFRVTGEIL

481 SVLGGVYFFF RGIQYFLQRR PSMKTLFVDS YSEMLFFLQS LFMLATVVLY FSHLKEYVAS

541 MVFSLALGWT NMLYYTRGFQ QMGIYAVMIE KMILRDLCRF MFVYIVFLFG FSTAVVTLIE

601 DGKNDSLPSE STSHRWRGPA CRPPDSSYNS LYSTCLELFK FTIGMGDLEF TENYDFKAVF

661 IILLLAYVIL TYILLLNMLI ALMGETVNKI AQESKNIWKL QRAITILDTE KSFLKCMRKA

721 FRSGKLLQVG YTPDGKDDYR WCFRVDEVNW TTWNTNVGII NEDPGNCEGV KRTLSFSLRS

781 SRVSGRHWKN FALVPLLREA SARDRQSAQP EEVYLRQFSG SLKPEDAEVF KSPAASGEK
```

However, one of skill in the art is aware that minor modifications may be made to this sequence while retaining the desired functionality of the protein. Alternatively, one could select another TRPV1 protein (e.g., from a guinea pig, mouse, or other species) and modify that sequence for use in the present invention. Such modifications may be made for a variety of reasons, including, e.g., to improve yield or purification.

In order to prepare an hTRPV1-expressing cell, a construct containing the coding sequence for the above-identified hTRPV1 sequence is selected. In one embodiment, the coding sequence is any sequence which encodes the above-identified protein. In another embodiment, the coding sequence is selected from one of the four transcript variants reported in NCBI for human TRPV1 (hTRPV1), (NM_018727.5, NM_080704.3, NM_080705.3, and NM_080706.3). The functional protein coding sequence (ORF—Open Reading Frame) for all the four transcripts is same. In the examples below, the construct contains the functional protein coding sequence only. However, in another embodiment, another variant, including the longest variant (variant 3, NCBI Accession No: NM_080706.3) may also be used. In still another embodiment, another ORF, or another sequence containing the ORF, is selected. In one embodiment, the sequence is cloned from an existing construct such as described in the examples below. In another embodiment, a recombinant sequence is used.

which are to be transduced (e.g., the N1E115 cells) are prepared using Lipofectamine 2000 (Invitrogen, Cat #11668-019), as described herein. The transduced cells are passaged using conventional methods and standard transfection techniques where utilized. By the end of second week, transfected stable colonies appear, which are then expanded and tested functionally. Final clonal candidate for the study was selected based on the functional assay data. These assays assess the ability of the cell to express hTRPV1 in a functional manner, i.e., such that upon being contacted with at least one of stimuli to which wt hTRPV1 respond, the hTRPV1 channel opens. For example, a cell expressing a functional hTRPV1 may respond to capsaicin, or to heat, or to other chemical, mechanical or physical stimuli characteristic of hTRPV1 in its natural setting. Examples of suitable assays are described in Example 49 below and include the membrane potential and calcium assays. Other suitable assays include standard single-cell voltage-clamp electrophysiology approaches such as used by Binshtok et al., Nature 449(4) 607-610, 2007. The TRPV1 assay is performed using a FLIPR®-384 fluorescence measurement platform (Molecular Devices, Inc.) operating in a membrane potential assay mode, or another suitable system, using hTRPV1-expressing cells as described herein. FLIPR® Membrane Potential Assay Kits (both blue and red) are available from Molecular Devices Corp (Sunnyvale, Calif., USA), which provides many of the dyes and materials used in the following assay. However, similar materials may be obtained from other sources as needed or desired.

The assay described herein used a method of activation for the TRPV1 channel which differs from that typically described in the literature and the art (i.e., capsaicin). The use of capsaicin to open the hTRPV1 channel in the cells proved to be unsuitable since it eroded the signal-to-noise window of the subsequent sodium channel response component of the assay in the hTRPV1-N1E115 cell line. Alternatively, it is anticipated that another cell line prepared as described herein could be substituted for this cell line. Therefore, another method to open the channel had to be developed. The heat activation method used herein has been found to yield robust and reproducible performance.

The assay is readily performed in multi-well assay plates into which cells in growth media are added and incubated under conditions which permit the formation of a confluent monolayer over a period of hours prior to the start of the assay. Conventional culture media and conditions may be utilized. Duplicate cell assay plates are prepared for each experiment.

The spent media from the cell seeded plates is removed on the day of the assay and replaced with Membrane potential Dye-Blue (Molecular Devices). The dye was prepared in assay buffer following manufacturer's instructions. The dye-loaded plate is incubated at room temperature (about 25° C.) for about 30 minutes in order to pre-load the cells with dye. Optionally, the cells may be loaded with the dye simultaneously with adding the test compounds.

An illustrative assay buffer is prepared using purified, deionized water according to Table 1. While the precise components may be varied, the ionic nature of the assay buffer is desirable for use in the assay. The pH is adjusted to 7.4 using potassium hydroxide and the volume is made up with Milli-Q® water (Millipore) up to 500 ml. Unless otherwise mentioned, all the dilutions were done in Assay Buffer.

TABLE 1

| Salt | Concentration (mM) |
| --- | --- |
| NaCl | 150 |
| KCl | 3.25 |
| $CaCl_2$ $2H_2O$ | 2 |
| $MgCl_2$ $6H_2O$ | 3 |
| HEPES | 10 |
| Glucose | 11 (198 mg/100 mL) |

The test compounds are diluted in the Assay Buffer and added to each well of a specific 384-well 'compound plate', which serves as a source plate for compound addition using the FLIPR® platform. The concentration of compounds in the compound-plate was adjusted to achieve the desired final concentration when added to the cells in the 'cell-plate'. After completion of the dye incubation period, the dye loaded cell-plates and the compound source plates are inserted into the FLIPR® Tetra device with a 384 FLIPR® tip box (Molecular Devices, Inc.) according to manufacturer's instructions. The compounds are robotically added to the dye loaded cell-plates using software integral to the FLIPR® Tetra instrument.

Immediately following compound addition, hTRPV1 is activated, in one of the duplicate cell plates, by heating. Specifically, entire multi-well plate containing the compound-cells mixture is incubated at 47° C. for 10 minutes, after which they are returned to room temperature (about 25° C.) for a further 30 minutes. Heat activation of hTRPV1 was omitted from the replicate cell plate which was simply maintained at room temperature for the entire 40 minutes.

A membrane potential response is elicited in the dye- and compound-loaded cells by the addition of veratridine which is a known sodium channel 'agonist'. As illustrated in an example herein, an agonist plate containing veratridine (Sigma) is prepared in advance and is inserted into suitable devices such as, e.g., the FLIPR® TETRA device for a "$2^{nd}$ addition" as instructed by the manufacturer. The concentration of veratridine in the 'agonist plate' was adjusted to achieve a final concentration of 100 μM when added to the cells in the cell-plate. Final concentrations of veratridine greater or lesser than 100 μM may also be used but the signal measured by the FLIPR® TETRA device or another suitable device may vary accordingly.

The exposure of the cells in the cell-plate to veratridine induces sodium channels in the cells to open and the resulting ion flux produces a membrane potential depolarization that is detected as a fluorescence signal by the FLIPR® Tetra Device. The activity of test compounds is determined by their ability to attenuate the veratridine-induced fluorescence signal, the most promising compounds are those that show an enhanced activity in the heat-activated cell plate over the non-heat-activated cell plate. This differential activity reflects enhanced compound uptake via the heat activated and open hTRPV1 channels and rests on the fact that sodium channel block requires test compounds to act from the cytoplasmic side of the cell membrane.

Once assessed using these screening assays, compounds may be selected for study in animal models. Routine evaluation of the analgesic effect of compounds was performed using a rodent pinch-pain test apparatus (Bioseb (France)). Skin pinch provides a mechanical stimulus that can be graded and which is particularly suitable for assessing acute mechanical pain (as described by A M Binshtok et al., Anesthesiology, July 2009, 111(1):127-137). Another rodent pain model typically use is the Hargreaves plantar test apparatus (IITC (USA)) which is particularly suitable for assessing thermal nociception.

The following examples are illustrative only and are not intended to limit the present invention.

EXAMPLES

Unless otherwise stated, all the raw materials are purchased from commercially available common suppliers. $^1$H-NMR spectra were recorded using TMS as the internal reference for $CDCl_3$ dissolved compounds. For DMSO-$d_6$, MeOD and $D_2O$ dissolved compounds the instrument was calibrated at δ 2.5, 3.3 and 4.82 ppm respectively. The chemical shift values are quoted in δ (parts per million).

For LCMS analysis LCMS/MS API 2000 (Applied Biosystem) instrument was used. The columns included:
  Column W: Zorbax® Extend C18 column, 4.6×50 mm, 5μ
  Column X: Gemini® NX C18 column, 4.6×50 mm, 5μ
  Column Y: Xbridge®C18 column, 4.6×50 mm, 5μ
  Column Z: Reprosil® column, 4.6×50 mm, 5μ

The eluent (solvent) typically included (acidic or basic buffer as aqueous phase):
  A channel: (i) 0.05% formic acid in water;
    (ii) 10 mM ammonium acetate in water; or
    (iii) 0.05% TFA in water.
  B channel: acetonitrile (organic phase).

The detector was UV measured at dual wavelengths: 220 and 260 nm.

The LCMS gradients were one of the following:
1. LCMS reaction monitoring and final compound analysis method (for general polarity compounds):
  Gradient condition: 5 min run time
  Time Programs: P1: 10 mM ammonium acetate in water/acetonitrile
    Q1: 0.05% TFA in water/acetonitrile,
    R1: 0.05% formic acid in water/acetonitrile.

The gradient varied acetonitrile from 10% to 90% to 10%.
Flow rate: 1.2 mL/min.

2. LCMS reaction monitoring and final compound analysis method in 12 min run (for close eluting compounds):
Gradient condition: 12 min run time
Time Programs: P2: 10 mM ammonium acetate in water/acetonitrile
Q2: 0.05% TFA in water/acetonitrile
R2: 0.05% formic acid in water/acetonitrile
The gradient varied acetonitrile from 5% to 90% to 5%
Flow rate: 1.0 mL/min.

3. LCMS after method development in HPLC—gradient conditions are as per HPLC.

Mass spectral data was obtained using the following:
Ionization technique: ESI (Electron Spray Ionization) using API (Atmospheric pressure Ionization) source
Declustering Potential: 10-70 V depending on the ionization of compound
Mass range: 100-800 amu
Scan type: Q1
Polarity: +/−ve
Ion Source Turbo spray
Ion spray voltage: +5500 for +ve mode and −4500 for −ve mode
Mass Source temperature: 200° C.

HPLC analysis was carried out using the Shimadzu® LC-2010, the Agilent® 1200 series, and Waters® Alliance® HT instruments. The columns included (i) Zorbax® SB C18 column (50×4.6 mm) 1.8μ, (ii) Atlantis® dC18 column (150× 4.6 mm) 5μ, (iii) Gemini® NX C18 column, (50×4.6 mm) 3μ, (iv) XBridge® C18 column (50×4.6 mm) 3μ, (v) XBridge® C18 column (50×4.6 mm) 5μ, and (iv) XTerra® C18 column (250×4.6 mm) 5μ, (v) Gemini® C18 column, (50×4.6 mm) 5μ, (vi) Zorbax® SB-C18 (4.6×50 mm) 5μ. The mobile phases included the following and the mobile phase gradients were changed from A. 90% to 10% to 90%. Flow rate was 1 mL/min.

A. 0.05% TFA in water, 0.05% HCOOH in water, 0.05% Acetic acid in water, 10 mM ammonium acetate in water (acidic or basic buffer); and B. acetonitrile or methanol (organic phase).

UPLC analysis was carried out using Agilent 1100 series and 1200 series instruments. The Columns used are (i) Zorbax® SB C18 (50×4.6 mm, 1.8μ) and (ii) Zorbax® XDB C18 (50×4.6 mm, 1.8μ) operating at ambient temperature. The mobile phase included the following and mobile phase gradients were changed from A. 95% to 5% to 95%. Flow rate varied from 0.8 to 1 ml/min.

A. 0.05% TFA in water, 0.05% HCOOH in water
B. acetonitrile

Example 1

General Procedure A

Preparation of N,N-dimethyl-N-[2-((2,4,6-trimethylbenzoyl)oxy)propyl]cyclohexanaminium iodide

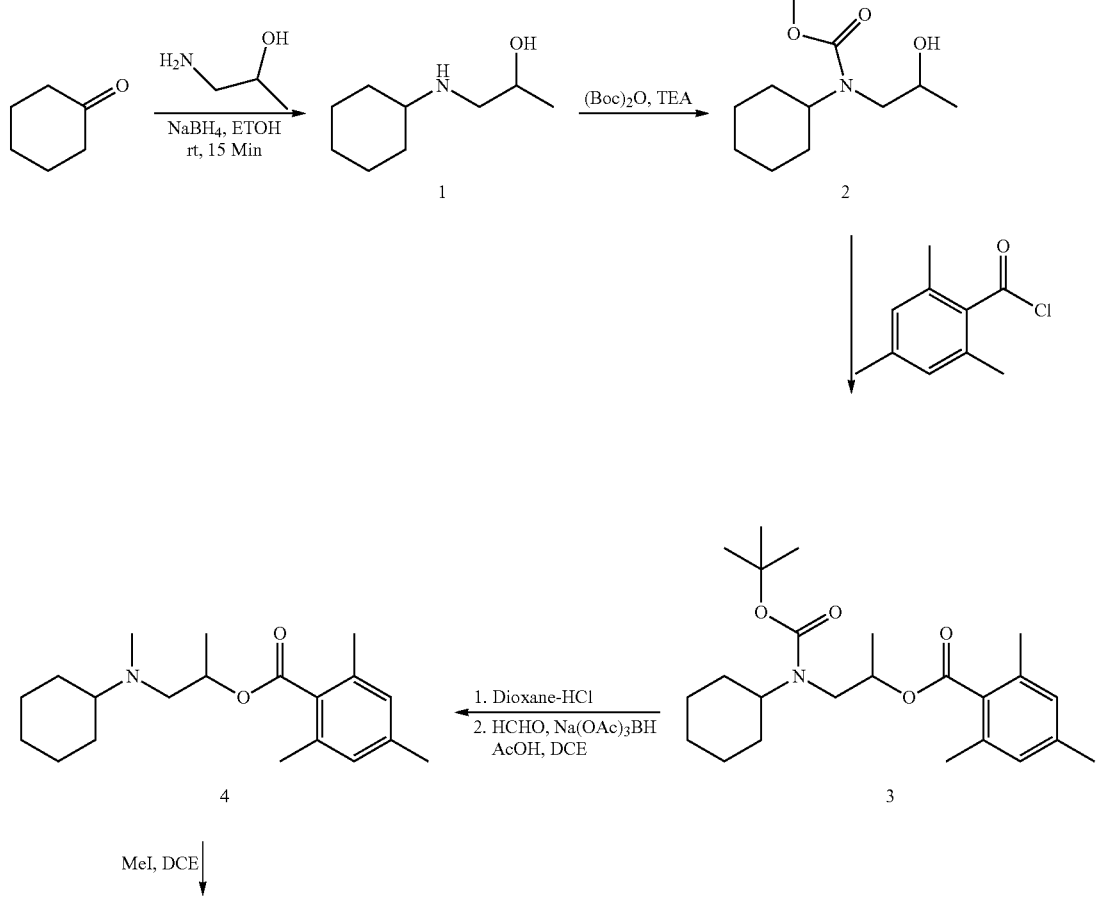

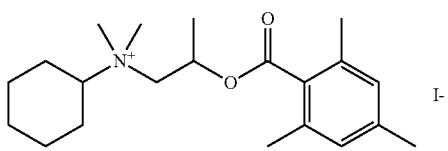

I: 1-(Cyclohexylamino)propan-2-ol

To a solution of 1-amino-2-propanol (15 g, 0.199 mol) in ethanol (300 ml) was added cyclohexanone (31.4 mL, 0.299 mol). The reaction mixture was stirred at 0-10° C. for 10 minutes. Sodium borohydride (10.8 g, 0.285 mol) was added at 0° C., then stirred at rt for 15 minutes. The resultant reaction mixture was quenched with water, filtered through the Celite® reagent, and solvent was evaporated. The residue was dissolved in 2N HCl, washed with ethyl acetate; the pH of the aqueous layer was adjusted to 8 using saturated sodium bicarbonate solution. The compound was extracted with ethyl acetate. The organic layer was dried over sodium sulphate, concentrated to dryness, and the crude material was subjected to column chromatography to obtain 1-(cyclohexylamino) propan-2-ol. Yield: 22 g (70.1%); $^1$H NMR (400 MHz, DMSO-$d_6$) δ 8.25 (bs, 1H), 5.25 (bs, 1H), 3.95-3.91 (m, 1H), 2.89-2.88 (dd, J=6, 9 Hz, 2H), 2.71-2.66 (m, 1H), 2.00-1.99 (m, 2H), 1.75-1.72 (m, 2H), 1.60-1.57 (m, 1H), 1.36-0.93 (m, 8H).

II: tert-Butyl cyclohexyl(2-hydroxypropyl)carbamate (2)

To a solution of 1-(cyclohexylamino)propan-2-ol (15 g, 95.5 mmol) in THF (300 ml) was added TEA (19.9 mL, 143.2 mmol) at 0° C. Boc-anhydride (22.8 g, 104.46 mmol) was then added. The resultant reaction mixture was stirred at rt for 6 hours. The reaction mixture was quenched with water, diluted with ethyl acetate and washed with water and brine. The organic layer was dried over sodium sulphate, and concentrated to dryness. Crude compound was purified by column chromatography (10-15% ethyl acetate/hexane) to obtain tert-butyl cyclohexyl(2-hydroxypropyl)carbamate. Yield: 16 g (65%); $^1$H NMR (400 MHz, CDCl$_3$) δ 4.41-4.25 (bs, 1H), 3.81-3.96 (m, 1H), 3.71-3.59 (m, 1H), 3.11-3.34 (m, 1H), 2.99-3.02 (m, 1H), 1.79-1.76 (m, 3H), 1.68-1.64 (m, 1H), 1.60 (m, 1H), 1.46-1.45 (s, 9H), 1.37-1.26 (m, 4H), 1.14-1.12 (d, J=6 Hz, 3H), 1.07-1.03 (m, 1H).

III: 1-((tert-Butoxycarbonyl)(cyclohexyl)amino)propan-2-yl 2,4,6-trimethylbenzoate (3)

To a solution of tert-butyl cyclohexyl(2-hydroxypropyl) carbamate (1 g, 3.89 mmol) in dry toluene (10 ml), 2,4,6-trimethyl-benzoyl chloride (0.510 mL, 4.280 mmol) was added. The resultant reaction mixture was stirred at rt for 16 hours. The reaction mixture was diluted in ethyl acetate and;j washed with water and brine. The organic layer was dried over sodium sulphate, and concentrated to dryness to obtain 1-((tert-butoxycarbonyl)(cyclohexyl)amino)propan-2-yl 2,4, 6-trimethylbenzoate. Yield: 1 g (64.10%); LCMS: m/z=404.4 [M+H], RT=2.76 min, (Column: Y, Program: P1)

IV: 1-(Cyclohexyl(methyl)amino)propan-2-yl 2,4,6-trimethylbenzoate (4)

1-((tert-butoxycarbonyl)(cyclohexyl)amino)propan-2-yl 2,4,6-trimethyl-benzoate (1.0 g, 2.48 mmol) was dissolved in dioxane-HCl (15 mL). The reaction mixture was stirred at rt for 2 hours. Solvent was evaporated. Crude solid was dissolved in DCE (10 ml) and formaldehyde (0.34 mL, 3.96 mmol), and sodium triacetoxyborohydride (1.67 g, 7.92 mmol) and acetic acid (0.5 mL) were added at 0° C. The resultant reaction mixture was stirred at rt for 16 hours. The reaction mixture was diluted in DCM and washed with 1N NaOH, water and brine. The organic layer was dried over sodium sulphate and concentrated to dryness. The crude compound was purified by column chromatography to obtain 1-(cyclohexyl(methyl)amino)propan-2-yl 2,4,6-trimethyl-benzoate. Yield: 0.6 (76%); $^1$H NMR (400 MHz, CDCl$_3$) δ 6.82 (s, 2H), 5.27-5.25 (m, 1H), 2.64-2.62 (m, 1H), 2.51-2.46 (m, 1H), 2.29 (s, 9H), 2.25 (s, 3H), 1.75-1.74 (m, 4H), 1.33-1.31 (d, J=6 Hz, 3H), 1.18-1.13 (m, 4H), 1.09-1.03 (m, 1H); LCMS: m/z=317.8 [M+H], RT=2.98 min (Column: X, Program: P1).

V: N,N-Dimethyl-N-[2-((2,4,6-trimethylbenzoyl) oxy)propyl]cyclohexanaminium iodide To a solution of 1-(cyclohexyl(methyl)amino)propan-2-yl 2,4,6-trimethylbenzoate (0.30 g, 0.946 mmol) in DCE (5 mL), methyl iodide (0.12 mL, 1.892 mmol) was added. The resultant reaction mixture was stirred at rt for 16 hours. The reaction mixture was diluted with DCM and concentrated to dryness. The crude product was subjected to column chromatography to obtain N,N-dimethyl-N-[2-((2,4,6-trimethylbenzoyl)oxy)propyl]cyclohexanaminium iodide. Yield: 0.109 g (25%). $^1$H NMR (400 MHz, CDCl$_3$) δ 6.86 (s, 2H), 5.70-5.67 (m, 1H), 4.52-4.48 (d, J=14 Hz, 1H), 3.83-3.77 (m, 1H), 3.70-3.64 (m, 1H), 3.34 (s, 3H), 3.28 (s, 3H), 2.29-2.01 (m, 10H), 2.01-1.98 (m, 1H), 1.84 (m, 1H), 1.64-1.62 (d, J=6 Hz, 4H), 1.47-1.38 (m, 4H), 1.13-1.08 (m, 2H). LCMS: m/z=332.2 [M$^+$], RT=3.01 min (Column: Y, Program: P1). HPLC: 99.53% (200 nm), RT 4.11 min (Mobile phase: A: ACN, B: 0.05% TFA in water, Column: Zorbax® SBC18 (50*4.6 mm) 1.8μ.

Example 2

General Procedure B

Preparation of N-[2-((2-isopropylbenzoyl)oxy)propyl]-N,N-dimethylcyclohexanaminium iodide

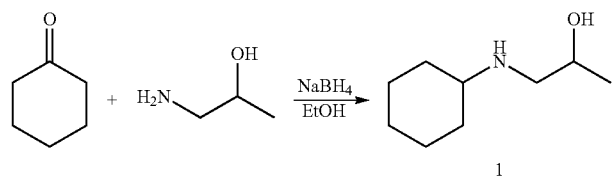

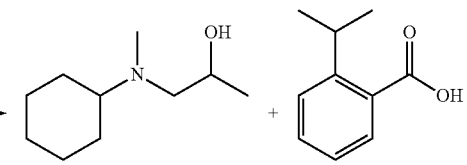

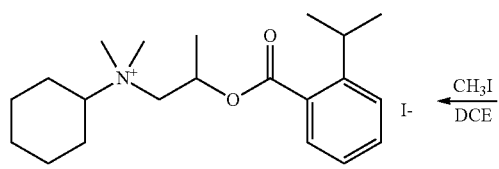

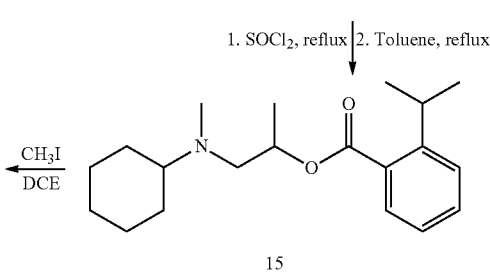

I. 1-(Cyclohexylamino)propan-2-ol (1)

To a stirred solution of 1-amino-2-propanol (1.0 mL, 13.31 mmol) in ethanol (15 mL) was added cyclohexanone (1.9 g, 19.9 mmol) at 0° C. The reaction mixture was stirred at 0° C. for 15 minutes and then NaBH$_4$ (0.725 g, 19.17 mmol) was added. The reaction mixture was stirred at rt for 15 minutes and then quenched with water. The reaction mixture was filtered through a Celite® pad and the filtrate was concentrated. The residue was dissolved in DCM, dried over Na$_2$SO$_4$, filtered and concentrated to provide 1-(cyclohexylamino)propan-2-ol. Yield: 2.6 g (crude). $^1$H NMR (DMSO-d$_6$) δ 4.39-4.36 (m, 1H), 3.61-3.57 (m, 1H), 2.47-2.30 (m, 3H), 1.78-1.75 (m, 2H), 1.66-1.63 (m, 2H), 1.55-1.52 (m, 1H), 1.23-1.12 (m, 3H), 1.03-0.89 (m, 5H). 1-(cyclohexylamino)propan-2-ol may also be prepared by following procedure of Example 1.

II. 1-(Cyclohexyl(methyl)amino)propan-2-ol (14)

To a stirred solution of 1-(cyclohexylamino)-propan-2-ol (crude 2.6 g) in DCE (30 mL) were added successively HCHO (35% in water, 2.1 mL, 24.8 mmol), Na(OAc)$_3$BH (10.5 g, 49.6 mmol) and acetic acid (1 mL) at ice-cold conditions. The resulting mixture was allowed to stir at rt for 16 hours. The reaction was diluted with ethyl acetate and basified with 1N NaOH. The organic layer was separated, washed with water and brine, dried over Na$_2$SO$_4$, filtered and concentrated. The crude material was purified by chromatography on silica-gel (230-400 mesh) eluting with 5% MeOH/DCM to provide 1-(cyclohexyl(methyl)amino)propan-2-ol. Yield: 1.0 g $^1$H NMR (DMSO-d$_6$) δ 4.11 (brs, 1H), 3.65-3.57 (m, 1H), 2.35-2.20 (m, 3H), 2.19 (s, 3H), 1.72-1.68 (m, 4H), 1.57-1.54 (m, 1H), 1.24-1.05 (m, 5H), 1.01 (d, J=6 Hz, 3H).

III. 1-(Cyclohexyl(methyl)amino)propan-2-yl 2-isopropylbenzoate (15)

Thionyl chloride (0.8 mL, 10.52 mmol) was added to 2-isopropylbenzoic acid (0.864 g, 5.26 mmol) at 0° C. and the resulting mixture was refluxed for 3 hours. The reaction mixture was concentrated under reduced pressure to provide the acid chloride. To a stirred solution of the acid chloride in dry toluene (15 mL) was added a solution of 1-(cyclohexyl(methyl)amino)propan-2-ol (0.75 g, 4.38 mmol) in dry toluene (10 mL) at 0° C. and the reaction mixture was refluxed for 16 hours. The reaction mixture was diluted with ethyl acetate and the organic layer was washed with saturated NaHCO$_3$, water and brine, dried over Na$_2$SO$_4$, filtered and concentrated. The crude material was purified by Combiflash® chromatography eluting with 9-11% ethyl acetate/hexane to provide 1-(cyclohexyl(methyl)amino)propan-2-yl 2-isopropylbenzoate. Yield: 0.88 g (63.38%). $^1$H NMR (DMSO-d$_6$) δ 7.56 (d, J=8 Hz, 1H), 7.51-7.44 (m, 2H), 7.26 (t, J=7 Hz, 1H), 5.15-5.12 (m, 1H), 3.61-3.54 (m, 1H), 2.67-2.59 (m, 1H), 2.33-2.31 (m, 1H), 2.23 (s, 3H), 1.71-1.67 (m, 4H), 1.57-1.54 (m, 1H), 1.25 (d, J=6 Hz, 3H), 1.21-1.05 (m, 11H). LCMS: m/z=318.4 [M+H], RT=2.51 min (Column: Y, Program: P1)

IV: N-[2-((2-Isopropylbenzoyl)oxy)propyl]-N,N-dimethylcyclohexanaminium iodide To a stirred solution of 1-(cyclohexyl(methyl)amino)propan-2-yl 2-isopropylbenzoate (0.45 g, 1.41 mmol) in DCE (3 mL) was added methyl iodide (0.35 mL, 5.67 mmol) and the reaction mixture was stirred at it for 16 hours in a sealed tube. The reaction mixture was concentrated and the crude material was purified by Combiflash® chromatography, eluting with 3-4% CH$_3$OH/DCM to provide a solid which was crystallized from methanol-ether to provide white N-[2-((2-isopropylbenzoyl)oxy)propyl]-N,N-dimethylcyclohexanaminium iodide. Yield: 0.415 g (64%). $^1$H NMR (DMSO-d$_6$) δ 7.71 (d, J=8 Hz, 1H), 7.58-7.50 (m, 2H), 7.31 (t, J=7 Hz, 1H), 5.57-5.54 (m, 1H), 3.93-3.87 (m, 1H), 3.67-3.57 (m, 2H), 3.38-3.34 (m, 1H), 3.05 (s, 3H), 3.02 (s, 3H), 2.17-2.08 (m, 2H), 1.87-1.84 (m, 1H), 1.75-1.72 (m, 1H), 1.54-1.42 (m, 3H), 1.40 (d, J=6 Hz, 3H), 1.24-1.19 (m, 7H), 1.13-0.99 (m, 2H). LCMS: m/z=332.0 [M$^+$], RT=3.01 min, (Column: Y, Program: P1). UPLC: 98.43% (200 nm), RT=3.60 min (Mobile Phase A. 0.05% TFA in water, B. Acetonitrile; Column: Zorbax® SB-C18 (4.6×50 mm) 1.8μ)

Example 3

General Procedure C

Preparation of N-[2-(benzoyloxy)propyl]-N,N-diethylcyclohexanaminium chloride

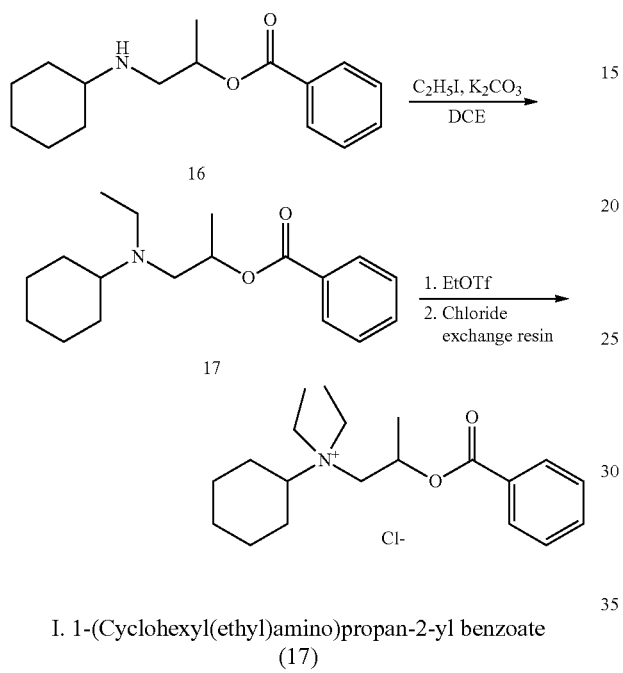

I. 1-(Cyclohexyl(ethyl)amino)propan-2-yl benzoate (17)

To a stirred solution of benzoic acid 2-cyclohexylamino-1-methyl-ethyl ester (1.0 g, 3.8 mmol) in DCE (20 mL) were added successively $K_2CO_3$ (2.11 g, 15.2 mmol) and ethyl iodide (1.8 mL, 22 mmol). The resulting mixture was heated at 50° C. for 16 hours in a sealed tube. Ethyl iodide (1.8 mL) was again added and the reaction mixture heated at 60° C. for another 24 hours. The reaction mixture was filtered and washed 5% methanol-DCM. The filtrate was concentrated and the crude material was purified by Combiflash® chromatography eluting with 6-7% methanol/DCM to provide 1-(cyclohexyl(ethyl)amino)propan-2-yl benzoate. Yield: 1.04 g (94.70%). $^1$H NMR (DMSO-$d_5$) δ 7.95 (d, J=7 Hz, 2H), 7.64 (t, J=7 Hz, 1H), 7.52 (t, J=8 Hz, 2H), 5.08-5.04 (m, 1H), 2.68-2.62 (m, 1H), 2.55-2.40 (m, 4H), 1.70-1.53 (m, 5H), 1.26 (d, J=6 Hz, 3H), 1.19-1.07 (m, 5H), 0.93 (t, J=7 Hz, 3H). LCMS: m/z=290.4 [M+H], RT=3.93 min, (Column: Y, Program: P1)

II. N-[2-(Benzoyloxy)propyl]-N,N-diethylcyclohexanaminium chloride

To a stirred solution of 1-(cyclohexyl(ethyl)amino)propan-2-yl benzoate (0.427 g, 1.47 mmol) in dry DCM (20 mL) was added ethyl triflate (0.25 mL, 1.92 mmol) dropwise at ice-cold conditions. The resulting mixture was stirred at rt for 16 hours in a sealed tube. The reaction mixture was concentrated and the crude material was purified by Combiflash chromatography eluting with 3-4% methanol/DCM to provide a sticky liquid. Amberlite® IRA-400 (Cl) chloride form resin (3.0 g) was added to a solution of the liquid compound in methanol (15 mL) and stirred for 6 hours. The solution was then filtered, concentrated and lyophilized to provide a solid. Because the fluorine NMR spectrum showed incomplete counter ion exchange, the solid was again treated with Amberlite® IRA-400 (Cl) chloride form resin in water and filtered. The filtrate was concentrated and the crude material was lyophilized to provide N-[2-(benzoyloxy)propyl]-N,N-diethylcyclohexanaminium chloride as an off white solid. Yield: 0.05 g (9.62%). $^1$H NMR (DMSO-$d_6$) δ 7.98 (d, J=8 Hz, 2H), 7.68 (t, J=7 Hz, 1H), 7.54 (t, J=8 Hz, 2H), 5.52-5.49 (m, 1H), 3.95-3.89 (m, 1H), 3.55 (d, J=15 Hz, 1H), 3.44-3.35 (m, 5H), 2.19-2.17 (m, 1H), 2.09-2.06 (m, 1H), 1.80-1.78 (m, 2H), 1.54-1.51 (m, 3H), 1.36 (d, J=6 Hz, 3H), 1.25-1.07 (m, 9H). LCMS: m/z=318.0 [M$^+$], RT=2.88 min, (Column: Y, Program: P1). UPLC: 98.70% (200 nm), RT=3.59 min, (Mobile Phase A. 0.05% TFA in water, B. Acetonitrile; Column: Zorbax® SB-C18 (4.6×50 mm) 1.8μ)

Example 4

General Procedure D

Preparation of N-[2-((4-isopropylbenzoyl)oxy)propyl]-N,N-dimethylcyclohexanaminium iodide

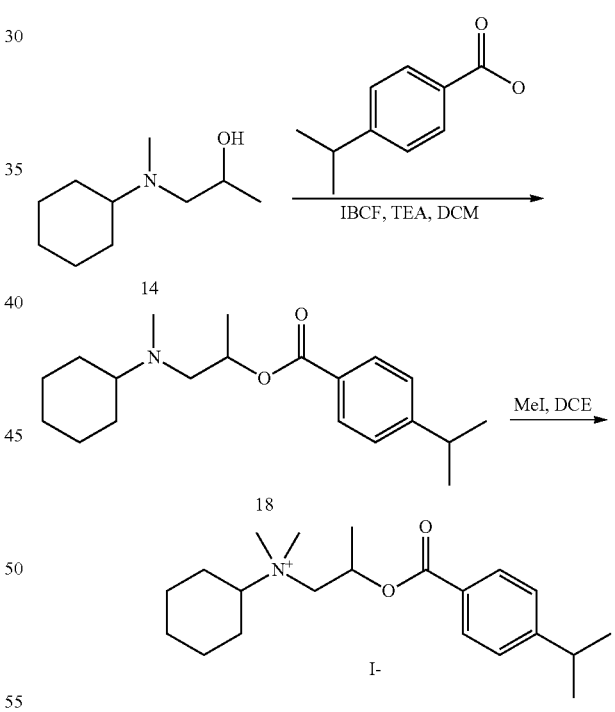

I. 1-(Cyclohexyl(methyl)amino)propan-2-yl 4-isopropylbenzoate (18)

To a solution of 4-isopropyl-benzoic acid (1 g, 6.09 mmol) in DCM (10 mL), isobutyl chloroformate (0.7 mL, 7.31 mmol) was added at −20 to −30° C. The reaction mixture was stirred at the same temperature for 30 minutes to provide a solution of the mixed anhydride. In another round-bottomed flask, 1-(cyclohexyl(methyl)amino)propan-2-ol (1.04 g, 6.09 mmol) was dissolved in DCM (15 mL) and TEA (2.1 mL, 15.24 mmol) was added. To this reaction mixture, the resultant mixed anhydride solution was added at 0° C. The resultant reaction mixture was stirred at same temperature for 45 minutes. The reaction mixture was extracted with DCM and washed with water and brine. The organic layer was dried over sodium sulphate and concentrated to dryness. The crude solid was purified using column chromatography to obtain 1-(cyclohexyl(methyl)amino)propan-2-yl 4-isopropylbenzoate. Yield: 0.6 g (32.4%). $^1$H NMR (400 MHz, CDCl$_3$) δ 7.95-7.93 (d, J=8 Hz, 2H), 7.27-7.25 (d, J=8 Hz, 2H), 5.20-5.18 (m, 1H), 2.96-2.92 (m, 1H), 2.72-2.67 (m, 1H), 2.53-2.48 (m, 1H), 2.33-2.28 (m, 4H), 1.76-1.74 (bs, 4H), 1.32-1.30 (d, J=6 Hz, 3H), 1.25 (bs, 6H), 1.24-1.18 (m, 5H).

II. N-[2-((4-Isopropylbenzoyl)oxy)propyl]-N,N-dimethylcyclohexanaminium iodide To a solution of 1-(cyclohexyl(methyl)amino)propan-2-yl 4-isopropylbenzoate (0.5 g, 1.57 mmol) in DCE (5 mL), methyl iodide (0.2 mL, 3.15 mmol) was added. The resultant reaction mixture was stirred at rt for 16 hours. The solvent was evaporated, and the crude product was purified by column chromatography. The product isolated was re-crystallized from methanol/ether. Yield: 134.9 mg (18.65%). $^1$H NMR (400 MHz, DMSO-d$_6$) δ 7.94-7.92 (d, J=8 Hz, 2H), 7.43-7.41 (d, J=8 Hz, 2H), 5.54-5.50 (m, 1H), 3.95-3.89 (m, 1H), 3.61-3.58 (d, J=14 Hz, 1H), 3.40-3.34 (m, 1H), 3.03-2.95 (m, 7H), 2.22-2.20 (d, J=11 Hz, 1H), 2.10-2.07 (d, J=11 Hz, 1H), 1.86-1.83 (m, 2H), 1.57-1.43 (m, 3H), 1.36-1.35 (d, J=6 Hz, 3H), 1.16-1.11 (m, 9H). LCMS: m/z=331.8 [M$^+$], RT=3.08 min (Column: Y, Program: P1). UPLC: 99.65% (200 nm), RT 3.09 min (Mobile phase: A. ACN, B. 0.05% HCOOH in water, Column: Gemini® NX C18 (50*4.6 mm) 3μ.

Example 5

General Procedure E

Preparation of (S)—N-[2-((4-(tert-butyl)benzoyl)oxy)propyl]-N,N-dimethylcyclohexanaminium bromide

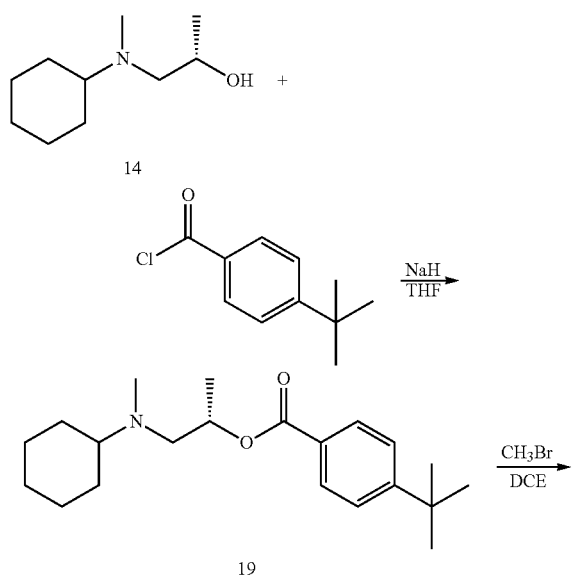

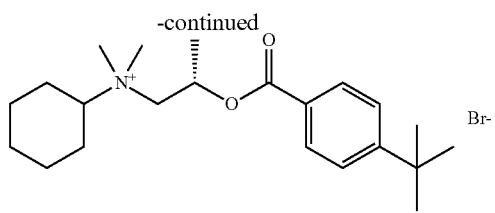

I. 1-(Cyclohexyl(methyl)amino)propan-2-yl 4-(tert-butyl)benzoate (19)

To a stirred solution of (S)-1-(cyclohexyl(methyl)amino)propan-2-ol (38.0 g, 222.22 mmol) in dry THF (700 ml) was added NaH (60% in oil, 9.77 g, 244.22 mmol) at 0° C. and stirred at rt for 20 mins. Then 4-tert-butylbenzoyl chloride (52.1 ml, 266.67 mmol) was added 0° C. and the reaction mixture was stirred at rt for 4 h. The reaction mixture was quenched with saturated NH$_4$Cl solution and diluted with ethyl acetate. The organic layer was washed with water and brine, dried over Na$_2$SO$_4$, filtered and concentrated. The crude material was purified by chromatography on neutral alumina eluting with 4-10% ethyl acetate-hexane to provide sticky compound I-(cyclohexyl(methyl)amino)propan-2-yl 4-(tert-butyl)benzoate. Yield: 26.0 g (35.7%). $^1$H NMR (DMSO-d$_6$) δ 7.86 (d, J=8 Hz, 2H), 7.52 (d, J=8 Hz, 2H), 5.12-5.07 (m, 1H), 2.66-2.61 (m, 1H), 2.46 (d, J=5 Hz, 1H), 2.31-2.28 (m, 1H), 2.24 (s, 3H), 1.68-1.65 (m, 4H), 1.55-1.53 (m, 1H), 1.29 (s, 9H), 1.25 (d, J=6 Hz, 3H), 1.18-1.02 (m, 5H); LCMS: m/z=332.2 [M+H], RT=2.85 min, (Column: Y, Program: P1)

II. (S)—N-[2-((4-(tert-butyl)benzoyl)oxy)propyl]-N,N-dimethylcyclohexanaminium bromide To a stirred solution of 1-(cyclohexyl(methyl)amino)propan-2-yl 4-(tert-butyl)benzoate (22.5 g, 6.798 mmol) in DCE (150 ml) was added methyl bromide (25% solution in toluene, 103 ml, 271.90 mmol) and reaction mixture was stirred at rt for 16 h. TLC showed very small amount of unreacted starting material. Hence another 0.5 eq. of methyl bromide was added and stirred at rt for 8 h. The reaction mixture was concentrated and the crude material was purified by chromatography on neutral alumina eluting with 2-8% methanol-DCM to provide an off white solid. The solid material was crystallized from DCM-ether to provide [2-(4-tert-butyl-benzoyloxy)-propyl]-cyclohexyl-dimethyl-ammonium bromide. Yield: 15.5 g (53.5%). $^1$H NMR (DMSO-d$_6$) δ 7.94 (d, J=8 Hz, 2H), 7.57 (d, J=8 Hz, 2H), 5.54-5.51 (m, 1H), 3.93 (dd, J=15, 9 Hz, 1H), 3.63 (d, J=14 Hz, 1H), 3.42-3.36 (m, 1H), 3.05 (s, 6H), 2.23-2.20 (m, 1H), 2.11-2.08 (m, 1H), 1.87-1.83 (m, 2H), 1.57-1.43 (m, 3H), 1.36 (d, J=6 Hz, 3H), 1.30 (s, 9H), 1.23-1.08 (m, 3H); LCMS: m/z=346.4 [M$^+$], RT=3.00 min, (Column: Y, Program: P1). UPLC: 99.90% (200 nm), RT=4.04 min (Mobile Phase A. 0.05% TFA in water, B. Acetonitrile; Column: Zorbax® SB-C18 (4.6×50 mm) 1.81μ).

The compounds of Examples 6 to 48 were prepared using the above schemes and synthetic methods described in Examples 1-5. Specific general procedures followed for each of Example 6 to 48 are noted in the following table, together with the respective mass spectral and chromatographical data.

TABLE 2

| Ex | Structure | Compound Name | M+ | LC retention time, min (Program, Column) | General synthetic procedure |
|---|---|---|---|---|---|
| 1 | 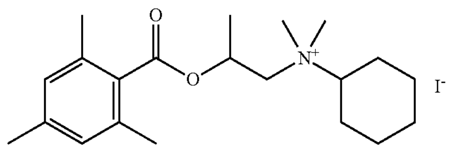 [SMILES: Cc1cc(C)c(C(=O)OC(C)C[N+](C)(C)C2CCCCC2)c(C)c1 ; [I-]] | N,N-dimethyl-N-[2-((2,4,6-trimethyl-benzoyl)oxy)propyl]cyclohexanaminium iodide | 332.2 | 3.01 (P1, Y) | A |
| 2 | 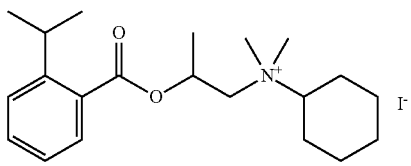 [SMILES: CC(C[N+](C)(C)C1CCCCC1)OC(=O)c1ccccc1C(C)C ; [I-]] | N-[2-((2-isopropyl-benzoyl)oxy)propyl]-N,N-dimethyl-cyclohexanaminium iodide | 332 | 3.01 (P1, Y) | B |
| 3 | 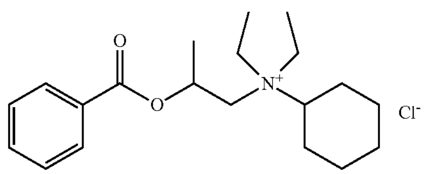 [SMILES: CC[N+](CC)(CC(C)OC(=O)c1ccccc1)C1CCCCC1 ; [Cl-]] | N-[2-(benzoyloxy)propyl]-N,N-diethyl-cyclohexanaminium chloride | 318 | 2.88 (P1, Y) | C |
| 4 | 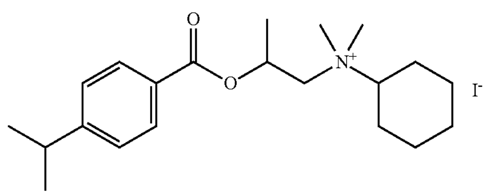 [SMILES: CC(C[N+](C)(C)C1CCCCC1)OC(=O)c1ccc(C(C)C)cc1 ; [I-]] | N-[2-((4-isopropylbenzoyl)oxy)propyl]-N,N-dimethyl-cyclohexanaminium iodide | 331.8 | 3.08 (P1, Y) | D |
| 5 | 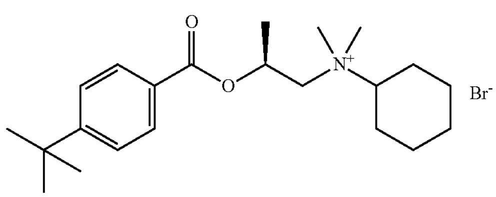 [SMILES: C[C@@H](C[N+](C)(C)C1CCCCC1)OC(=O)c1ccc(C(C)(C)C)cc1 ; [Br-]] | (S)-N-[2-((4-(tert-butyl)benzoyl)oxy)propyl]-N,N-dimethyl-cyclohexanaminium bromide | 346.4 | 3.00 (P1, Y) | E |
| 6 | 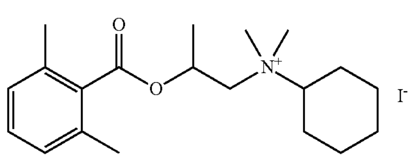 [SMILES: Cc1cccc(C)c1C(=O)OC(C)C[N+](C)(C)C1CCCCC1 ; [I-]] | N-[2-((2,6-Dimethylbenzoyl)oxy)propyl]-N,N-dimethyl-cyclohexanaminium iodide | 318.2 | 2.38 (R1, X) | A |
| 7 | 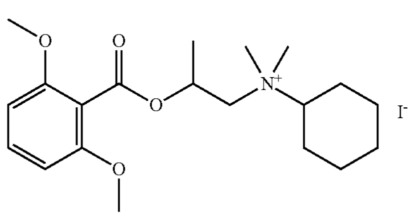 [SMILES: COc1cccc(OC)c1C(=O)OC(C)C[N+](C)(C)C1CCCCC1 ; [I-]] | N-[2-((2,6-Dimethoxybenzoyl)oxy)propyl]-N,N-dimethyl-cyclohexanaminium iodide | 350.2 | 2.69 (P1, Y) | A |
| 8 | 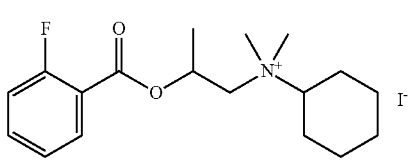 [SMILES: CC(C[N+](C)(C)C1CCCCC1)OC(=O)c1ccccc1F ; [I-]] | N-[2-((2-Fluorobenzoyl)oxy)propyl]-N,N-dimethyl-cyclohexanaminium iodide | 308.0 | 2.68 (P1, W) | A |

TABLE 2-continued

| Ex | Structure | Compound Name | M+ | LC retention time, min (Program, Column) | General synthetic procedure |
|---|---|---|---|---|---|
| 9 | 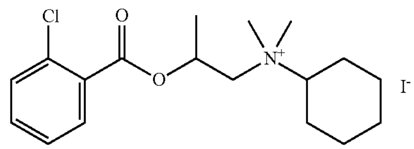 [SMILES: CC(C[N+](C)(C)C1CCCCC1)OC(=O)c1ccccc1Cl ; [I-]] | N-[2-((2-Chlorobenzoyl)oxy)propyl]-N,N-dimethyl-cyclohexanaminium iodide | 323.8 | 2.93 (P1, Y) | A |
| 10 | 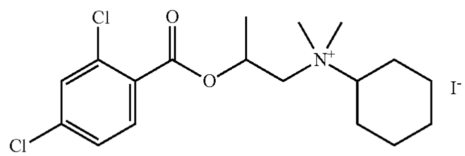 [SMILES: CC(C[N+](C)(C)C1CCCCC1)OC(=O)c1ccc(Cl)cc1Cl ; [I-]] | N-[2-((2,4-Dichlorobenzoyl)oxy)propyl]-N,N-dimethyl-cyclohexanaminium iodide | 357.8 | 3.07 (P1, Y) | A |
| 11 | 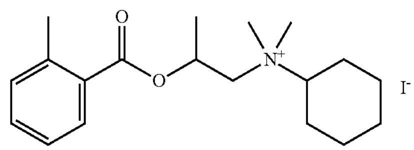 [SMILES: Cc1ccccc1C(=O)OC(C)C[N+](C)(C)C1CCCCC1 ; [I-]] | N,N-Dimethyl-N-[2-((2-methylbenzoyl)oxy)propyl]cyclohexanaminium iodide | 304.0 | 2.88 (P1, Y) | A |
| 12 | 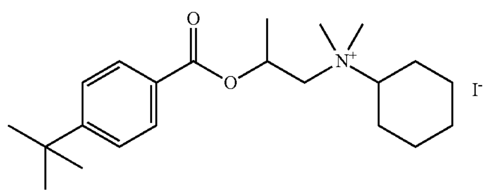 [SMILES: CC(C[N+](C)(C)C1CCCCC1)OC(=O)c1ccc(C(C)(C)C)cc1 ; [I-]] | N-[2-((4-(tert-Butyl)benzoyl)oxy)propyl]-N,N-dimethyl-cyclohexanaminium iodide | 346 | 3.09 (P1, X) | B |
| 13 | 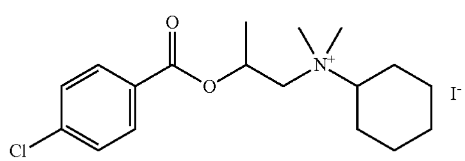 [SMILES: CC(C[N+](C)(C)C1CCCCC1)OC(=O)c1ccc(Cl)cc1 ; [I-]] | N-[2-((4-Chlorobenzoyl)oxy)propyl]-N,N-dimethyl-cyclohexanaminium iodide | 324.0 | 2.86 (P1, Y) | B |
| 14 | 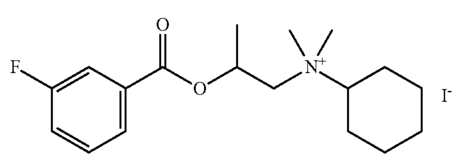 [SMILES: CC(C[N+](C)(C)C1CCCCC1)OC(=O)c1cccc(F)c1 ; [I-]] | N-[2-((3-Fluorobenzoyl)oxy)propyl]-N,N-dimethyl-cyclohexanaminium iodide | 308.2 | 2.77 (P1, Y) | B |
| 15 | 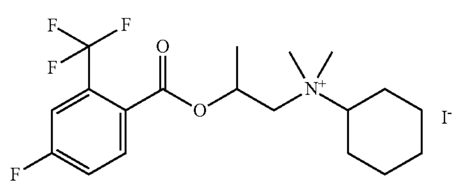 [SMILES: CC(C[N+](C)(C)C1CCCCC1)OC(=O)c1ccc(F)cc1C(F)(F)F ; [I-]] | N-[2-((4-Fluoro-2-(trifluoromethyl)benzoyl)oxy)propyl]-N,N-dimethyl-cyclohexanaminium iodide | 375.8 | 2.90 (P1, Y) | B |
| 16 | 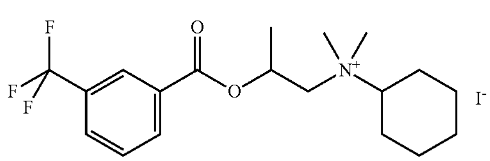 [SMILES: CC(C[N+](C)(C)C1CCCCC1)OC(=O)c1cccc(C(F)(F)F)c1 ; [I-]] | N,N-Dimethyl-N-[2-((3-(trifluoromethyl)benzoyl)oxy)propyl]cyclohexanaminium iodide | 358.3 | 2.99 (P1, Y) | B |
| 17 | 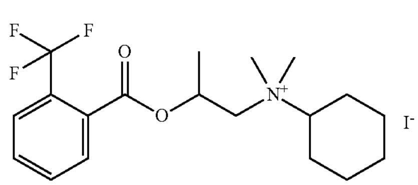 [SMILES: CC(C[N+](C)(C)C1CCCCC1)OC(=O)c1ccccc1C(F)(F)F ; [I-]] | N-[2-((2-(Trifluoromethyl)benzoyl)oxy)propyl]-N,N-dimethylcyclohexanaminium iodide | 358.0 | 2.90 (P1, Y) | B |

TABLE 2-continued

| Ex | Structure | Compound Name | M+ | LC retention time, min (Program, Column) | General synthetic procedure |
|---|---|---|---|---|---|
| 18 | 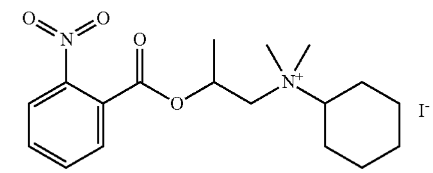 [SMILES: CC(C[N+](C)(C)C1CCCCC1)OC(=O)c1ccccc1[N+](=O)[O-] ; [I-]] | N,N-Dimethyl-N-[2-((2-nitrobenzoyl)oxy)propyl]cyclohexanaminium iodide | 335.3 | 2.79 (P1, Y) | B |
| 19 | 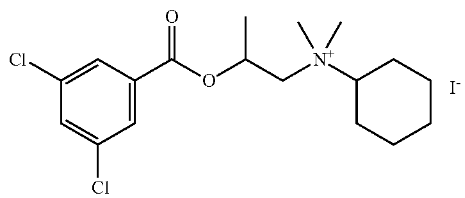 [SMILES: CC(C[N+](C)(C)C1CCCCC1)OC(=O)c1cc(Cl)cc(Cl)c1 ; [I-]] | N-[2-((3,5-Dichlorobenzoyl)oxy)propyl]-N,N-dimethyl-cyclohexanaminium iodide | 358.1 | 3.14 (P1, Y) | B |
| 20 | 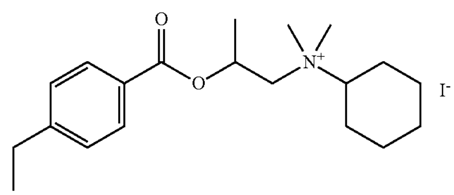 [SMILES: CCc1ccc(C(=O)OC(C)C[N+](C)(C)C2CCCCC2)cc1 ; [I-]] | N-[2-((4-Ethylbenzoyl)oxy)propyl]-N,N-dimethyl-cyclohexanaminium iodide | 318 | 2.94 (P1, Y) | B |
| 21 | 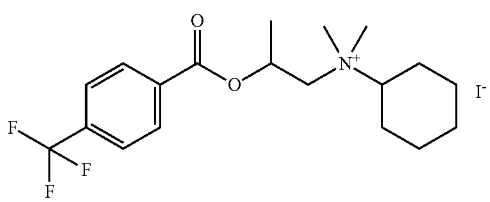 [SMILES: CC(C[N+](C)(C)C1CCCCC1)OC(=O)c1ccc(C(F)(F)F)cc1 ; [I-]] | N,N-Dimethyl-N-[2-((4-(trifluoromethyl)benzoyl)oxy)propyl]cyclohexanaminium iodide | 358.4 | 2.91 (P1, Y) | B |
| 22 | 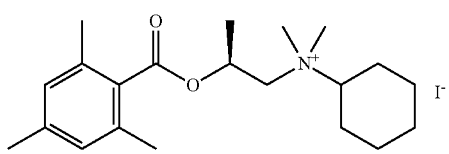 [SMILES: Cc1cc(C)c(C(=O)O[C@@H](C)C[N+](C)(C)C2CCCCC2)c(C)c1 ; [I-]] | (S)-N,N-Dimethyl-N-[2-((2,4,6-trimethylbenzoyl)oxy)propyl]cyclohexanaminium iodide | 332 | 2.96 (P1, Y) | A |
| 23 | 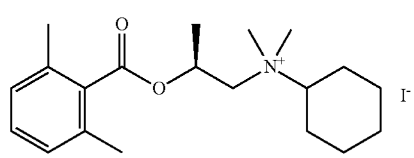 [SMILES: Cc1cccc(C)c1C(=O)O[C@@H](C)C[N+](C)(C)C1CCCCC1 ; [I-]] | (S)-N-[2-((2,6-Dimethylbenzoyl)oxy)propyl]-N,N-dimethyl-cyclohexanaminium iodide | 318 | 2.85 (P1, Y) | A |
| 24 | 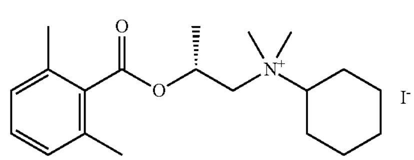 [SMILES: Cc1cccc(C)c1C(=O)O[C@H](C)C[N+](C)(C)C1CCCCC1 ; [I-]] | (R)-N-[2-((2,6-Dimethylbenzoyl)oxy)propyl]-N,N-dimethyl-cyclohexanaminium iodide | 318.2 | 2.83 (P1, Y) | A |
| 25 | 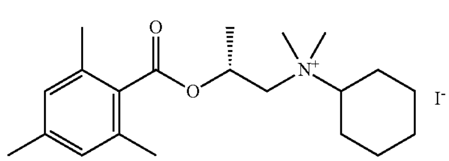 [SMILES: Cc1cc(C)c(C(=O)O[C@H](C)C[N+](C)(C)C2CCCCC2)c(C)c1 ; [I-]] | (R)-N,N-Dimethyl-N-[2-((2,4,6-trimethylbenzoyl)oxy)propyl]cyclohexanaminium iodide | 332.2 | 2.96 (P1, Y) | A |

TABLE 2-continued

| Ex | Structure | Compound Name | M+ | LC retention time, min (Program, Column) | General synthetic procedure |
|---|---|---|---|---|---|
| 26 | 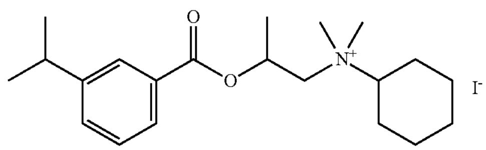 [SMILES: CC(C[N+](C)(C)C1CCCCC1)OC(=O)c1cccc(C(C)C)c1 ; [I-]] | N-[2-((3-Isopropylbenzoyl)oxy)propyl]-N,N-dimethylcyclohexanaminium iodide | 332.2 | 3.03 (P1, Y) | B |
| 27 | 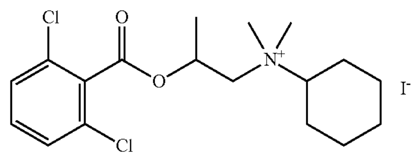 [SMILES: CC(C[N+](C)(C)C1CCCCC1)OC(=O)c1c(Cl)cccc1Cl ; [I-]] | N-[2-((2,6-Dichlorobenzoyl)oxy)propyl]-N,N-dimethylcyclohexanaminium iodide | 334.2 | 2.65 (P1, Y) | A |
| 28 | 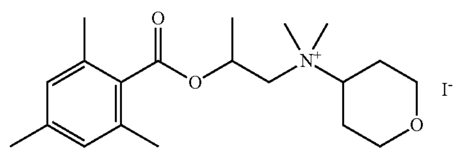 [SMILES: Cc1cc(C)c(C(=O)OC(C)C[N+](C)(C)C2CCOCC2)c(C)c1 ; [I-]] | N,N-Dimethyl-N-[2-((2,4,6-trimethylbenzoyl)oxy)propyl]tetrahydro-2H-pyran-4-aminium iodide | 357.8 | 2.82 (P1, Y) | A |
| 29 | 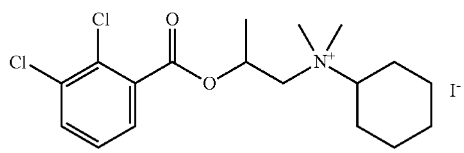 [SMILES: CC(C[N+](C)(C)C1CCCCC1)OC(=O)c1cccc(Cl)c1Cl ; [I-]] | N-[2-((2,3-Dichlorobenzoyl)oxy)propyl]-N,N-dimethylcyclohexanaminium iodide | 357.8 | 2.93 (P1, Y) | B |
| 30 | 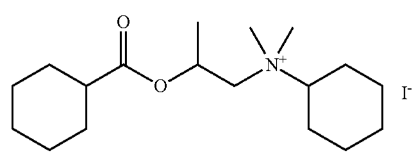 [SMILES: CC(C[N+](C)(C)C1CCCCC1)OC(=O)C1CCCCC1 ; [I-]] | N-[2-((Cyclohexanecarbonyl)oxy)propyl]-N,N-diethylcyclohexanaminium iodide | 296.0 | 2.97 (P1, Y) | B |
| 31 | 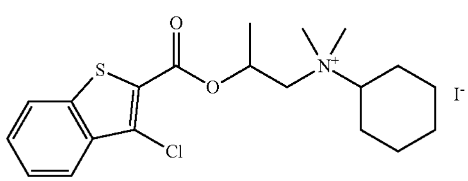 [SMILES: CC(C[N+](C)(C)C1CCCCC1)OC(=O)c1sc2ccccc2c1Cl ; [I-]] | N-[2-((3-Chlorobenzo[b]thiophene-2-carbonyl)oxy)propyl]-N,N-dimethylcyclohexanaminium iodide | 380.0 | 3.11 (P1, Y) | B |
| 32 | 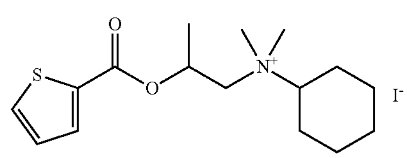 [SMILES: CC(C[N+](C)(C)C1CCCCC1)OC(=O)c1cccs1 ; [I-]] | N,N-Dimethyl-N-[2-((thiophene-2-carbonyl)oxy)propyl]cyclohexanaminium iodide | 296.2 | 2.60 (P1, Y) | B |
| 33 | 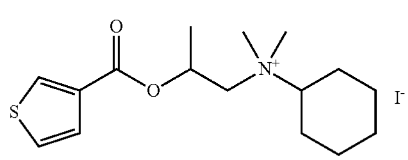 [SMILES: CC(C[N+](C)(C)C1CCCCC1)OC(=O)c1ccsc1 ; [I-]] | N,N-Dimethyl-N-[2-((thiophene-3-carbonyl)oxy)propyl]cyclohexanaminium iodide | 296.2 | 2.52 (P1, Y) | B |
| 34 | 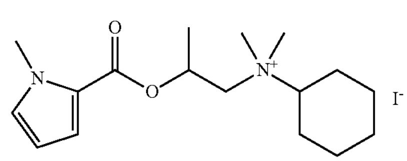 [SMILES: CC(C[N+](C)(C)C1CCCCC1)OC(=O)c1cccn1C ; [I-]] | N,N-Dimethyl-N-[2-((1-methyl-1H-pyrrole-2-carbonyl)oxy)propyl]cyclohexanaminium iodide | 293.2 | 2.77 (P1, Y) | B |

TABLE 2-continued

| Ex | Structure | Compound Name | M+ | LC retention time, min (Program, Column) | General synthetic procedure |
|---|---|---|---|---|---|
| 35 | 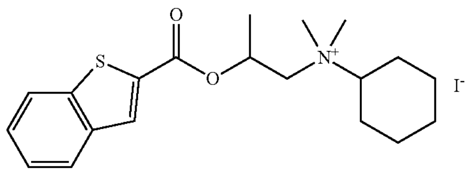 [SMILES: CC(C[N+](C)(C)C1CCCCC1)OC(=O)c1cc2ccccc2s1 ; [I-]] | N-[2-((Benzo[b]thiophene-2-carbonyl)oxy)propyl]-N,N-dimethyl-cyclohexanaminium iodide | 346.0 | 2.89 (P1, Y) | B |
| 36 | 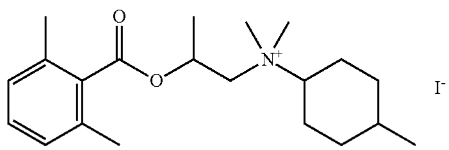 [SMILES: Cc1cccc(C)c1C(=O)OC(C)C[N+](C)(C)C1CCC(C)CC1 ; [I-]] | N-[2-((2,6-Dimethylbenzoyl)oxy)propyl]-N,N,4-trimethylcyclo-hexanaminium iodide | 332.3 | 3.02 (P1, Y) | B |
| 37 | 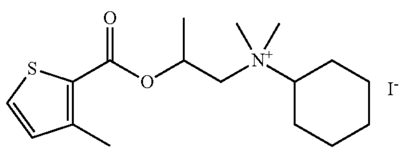 [SMILES: Cc1ccsc1C(=O)OC(C)C[N+](C)(C)C1CCCCC1 ; [I-]] | N,N-Dimethyl-N-[2-((3-methylthiophene-2-carbonyl)oxy)propyl]cyclohexanaminium iodide | 310.0 | 2.78 (P1, X) | B |
| 38 | 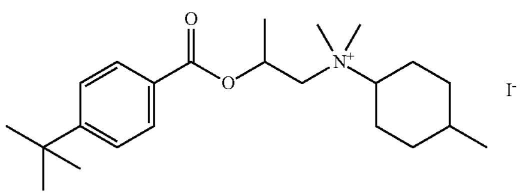 [SMILES: CC1CCC([N+](C)(C)CC(C)OC(=O)c2ccc(C(C)(C)C)cc2)CC1 ; [I-]] | N-[2-((4-(tert-butyl)benzoyl)oxy)propyl]-N,N,4-trimethylcyclo-hexanaminium iodide | 360.4 | 3.17 (P1, Y) | B |
| 39 | 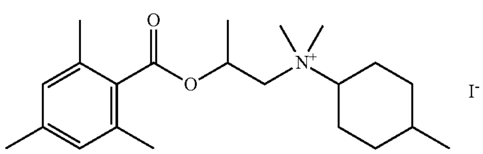 | N,N,4-Trimethyl-N-[2-((2,4,6-trimethyl-benzoyl)oxy)propyl]cyclohexanaminium iodide | 346.2 | 2.98 (P1, Y) | B |
| 40 | 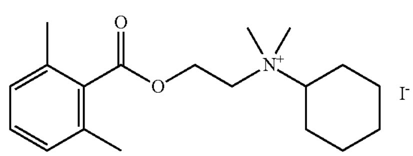 [SMILES: Cc1cccc(C)c1C(=O)OCC[N+](C)(C)C1CCCCC1 ; [I-]] | N-[2-((2,6-Dimethylbenzoyl)oxy)ethyl]-N,N-dimethylcyclo-hexanaminium iodide | 304.2 | 2.80 (P1, Y) | B |
| 41 | 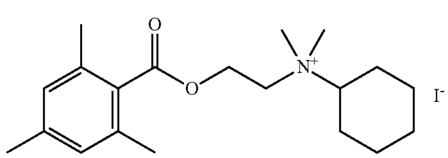 [SMILES: Cc1cc(C)c(C(=O)OCC[N+](C)(C)C2CCCCC2)c(C)c1 ; [I-]] | N-[2-((2,4,6-Trimethylbenzoyl)oxy)ethyl]-N,N-dimethylcyclo-hexanaminium iodide | 318.2 | 2.89 (P1, Y) | B |
| 42 | 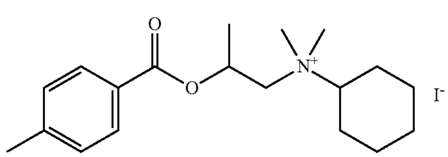 [SMILES: Cc1ccc(C(=O)OC(C)C[N+](C)(C)C2CCCCC2)cc1 ; [I-]] | N,N-Dimethyl-N-[2-((4-methylbenzoyl)oxy)propyl]cyclohexanaminium iodide | 304.2 | 2.82 (P1, Y) | B |
| 43 | 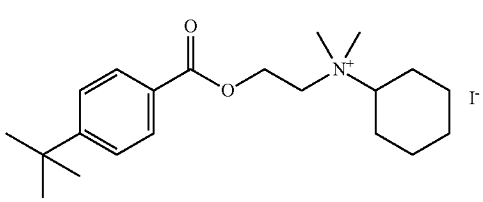 [SMILES: CC(C)(C)c1ccc(C(=O)OCC[N+](C)(C)C2CCCCC2)cc1 ; [I-]] | N-[2-((4-(tert-butyl)benzoyl)oxy)ethyl]-N,N-dimethylcyclo-hexanaminium iodide | 332.4 | 3.04 (P1, Y) | B |

TABLE 2-continued

| Ex | Structure | Compound Name | M+ | LC retention time, min (Program, Column) | General synthetic procedure |
|---|---|---|---|---|---|
| 44 | 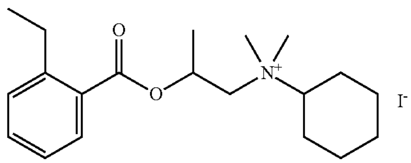 [SMILES: CCc1ccccc1C(=O)OC(C)C[N+](C)(C)C1CCCCC1 ; [I-]] | N-[2-((2-Ethylbenzoyl)oxy)propyl]-N,N-dimethylcyclo-hexanaminium iodide | 318.2 | 3.05 (P1, Y) | B |
| 45 | 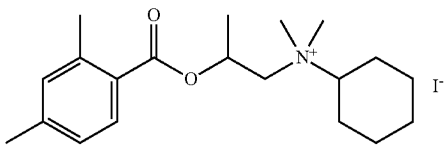 [SMILES: Cc1ccc(C(=O)OC(C)C[N+](C)(C)C2CCCCC2)c(C)c1 ; [I-]] | N-[2-((2,4-Dimethylbenzoyl)oxy)propyl]-N,N-dimethylcyclo-hexanaminium iodide | 318.0 | 3.03 (P1, Y) | B |
| 46 | 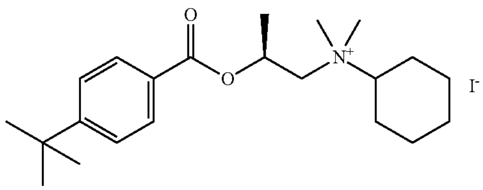 [SMILES: C[C@@H](C[N+](C)(C)C1CCCCC1)OC(=O)c1ccc(C(C)(C)C)cc1 ; [I-]] | (S)-N-[2-((4-(tert-butyl)benzoyl)oxy)propyl]-N,N-dimethylcyclo-hexanaminium iodide | 346.0 | 2.82 (P1, W) | B |
| 47 | 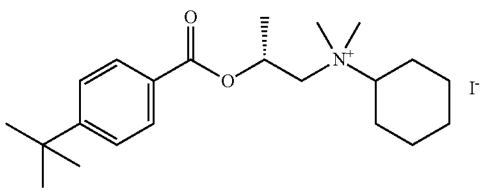 [SMILES: C[C@H](C[N+](C)(C)C1CCCCC1)OC(=O)c1ccc(C(C)(C)C)cc1 ; [I-]] | (R)-N-[2-((4-(tert-butyl)benzoyl)oxy)propyl]-N,N-dimethylcyclo-hexanaminium iodide | 346.0 | 3.12 (P1, Y) | B |
| 48 | 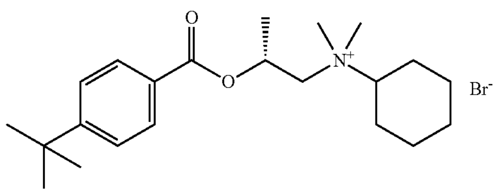 [SMILES: C[C@H](C[N+](C)(C)C1CCCCC1)OC(=O)c1ccc(C(C)(C)C)cc1 ; [Br-]] | (R)-N-[2-((4-(tert-butyl)benzoyl)oxy)propyl]-N,N-dimethylcyclo-hexanaminium bromide | 346.0 | 3.11 (P1, Y) | E |

Example 49 hTRPV1-Expressing Cells and In Vitro Assays

In vitro assays were developed for assessing the inhibition of sodium channel response with compounds following stimulation by heat (47° C.) in cells expressing hTRPV1.

A. Generation of Cells Expressing hTRPV1

The following cells were developed as a preliminary screen to help select the compound which would progress to further assessment in an in vivo assay.

(i) Plasmid for Delivering hTRPV1 to Cells

In order to prepare the cell line, the open reading frame encoding hTRPV1 was amplified by PCR from a cDNA library based on the human neuroblastoma cell line IMR322 [NCBI dbEST ID: 18353] using the following primers:

(a) TRPV1_KpnIF (Forward Primer)

[SEQ ID NO: 2]

5'-ATAAACGGTACCGCCGCCACCATGAAGAAATGGAGCAGCAC-3'

(b) TRPV1_PmeIR (Reverse Primer)

[SEQ ID NO: 3]

5'-ATCGGTTTAAACTCACTTCTCTCCGGAAGCGGC-3'

The forward primer contains a KpnI site [GGTACC (underlined in (a) above] and a Kozak sequence [GCCGCCACC (double-underlined in (a)]. The reverse primer contains a PmeI site [GTTTAAAC, underlined in (b)].

The open reading frame of hTRPV1 (corresponding to NCBI NM_080706.3) is: SEQ ID NO:4:

ATGAAGAAATGGAGCAGCACAGACTTGGGGGCAGCTGCGGACCCACTCCAAAAGGACACC

TGCCCAGACCCCCTGGATGGAGACCCTAACTCCAGGCCACCTCCAGCCAAGCCCCAGCTC

TCCACGGCCAAGAGCCGCACCCGGCTCTTTGGGAAGGGTGACTCGGAGGAGGCTTTCCCG

```
GTGGATTGCCCTCACGAGGAAGGTGAGCTGGACTCCTGCCCGACCATCACAGTCAGCCCT
GTTATCACCATCCAGAGGCCAGGAGACGGCCCCACCGGTGCCAGGCTGCTGTCCCAGGAC
TCTGTCGCCGCCAGCACCGAGAAGACCCTCAGGCTCTATGATCGCAGGAGTATCTTTGAA
GCCGTTGCTCAGAATAACTGCCAGGATCTGGAGAGCCTGCTGCTCTTCCTGCAGAAGAGC
AAGAAGCACCTCACAGACAACGAGTTCAAAGACCCTGAGACAGGGAAGACCTGTCTGCTG
AAAGCCATGCTCAACCTGCACGACGGACAGAACACCACCATCCCCCTGCTCCTGGAGATC
GCGCGGCAAACGGACAGCCTGAAGGAGCTTGTCAACGCCAGCTACACGGACAGCTACTAC
AAGGGCCAGACAGCACTGCACATCGCCATCGAGAGACGCAACATGGGCCCTGGTGACCCTC
CTGGTGGAGAACGGAGCAGACGTCCAGGCTGCGGCCCATGGGGACTTCTTTAAGAAAACC
AAAGGGCGGCCTGGATTCTACTTCGGTGAACTGCCCCTGTCCCTGGCCGCGTGCACCAAC
CAGCTGGGCATCGTGAAGTTCCTGCTGCAGAACTCCTGGCAGACGGCCGACATCAGCGCC
AGGGACTCGGTGGGCAACACGGTGCTGCACGCCCTGGTGGAGGTGGCCGACAACACGGCC
GACAACACGAAGTTTGTGACGAGCATGTACAATGAGATTCTGATCCTGGGGGCCAAACTG
CACCCGACGCTGAAGCTGGAGGAGCTCACCAACAAGAAGGGAATGACGCCGCTGGCTCTG
GCAGCTGGGACCGGGAAGATCGGGGTCTTGGCCTATATTCTCCAGCGGGAGATCCAGGAG
CCCGAGTGCAGGCACCTGTCCAGGAAGTTCACCGAGTGGGCCTACGGGCCCGTGCACTCC
TCGCTGTACGACCTGTCCTGCATCGACACCTGCGAGAAGAACTCGGTGCTGGAGGTGATC
GCCTACAGCAGCAGCGAGACCCCTAATCGCCACGACATGCTCTTGGTGGAGCCGCTGAAC
CGACTCCTGCAGGACAAGTGGGACAGATTCGTCAAGCGCATCTTCTACTTCAACTTCCTG
GTCTACTGCCTGTACATGATCATCTTCACCATGGCTGCCTACTACAGGCCCGTGGATGGC
TTGCCTCCCTTTAAGATGGAAAAAACTGGAGACTATTTCCGAGTTACTGGAGAGATCCTG
TCTGTGTTAGGAGGAGTCTACTTCTTTTTCCGAGGGATTCAGTATTTCCTGCAGAGGCGG
CCGTCGATGAAGACCCTGTTTGTGGACAGCTACAGTGAGATGCTTTTCTTTCTGCAGTCA
CTGTTCATGCTGGCCACCGTGGTGCTGTACTTCAGCCACCTCAAGGAGTATGTGGCTTCC
ATGGTATTCTCCCTGGCCTTGGGCTGGACCAACATGCTCTACTACACCCGCGGTTTCCAG
CAGATGGGCATCTATGCCGTCATGATAGAGAAGATGATCCTGAGAGACCTGTGCCGTTTC
ATGTTTGTCTACATCGTCTTCTTGTTCGGTTTTCCACAGCGGTGGTGACGCTGATTGAA
GACGGGAAGAATGACTCCCTGCCGTCTGAGTCCACGTCGCACAGGTGGCGGGGGCCTGCC
TGCAGGCCCCCGATAGCTCCTACAACAGCCTGTACTCCACCTGCCTGGAGCTGTTCAAG
TTCACCATCGGCATGGGCGACCTGGAGTTCACTGAGAACTATGACTTCAAGGCTGTCTTC
ATCATCCTGCTGCTGGCCTATGTAATTCTCACCTACATCCTCCTGCTCAACATGCTCATC
GCCCTCATGGGTGAGACTGTCAACAAGATCGCACAGGAGAGCAAGAACATCTGGAAGCTG
CAGAGAGCCATCACCATCCTGGACACGGAGAAGAGCTTCCTTAAGTGCATGAGGAAGGCC
TTCCGCTCAGGCAAGCTGCTGCAGGTGGGGTACACACCTGATGGCAAGGACGACTACCGG
TGGTGCTTCAGGGTGGACGAGGTGAACTGGACACCTGGAACACCAACGTGGGCATCATC
AACGAAGACCCGGGCAACTGTGAGGGCGTCAAGCGCACCCTGAGCTTCTCCCTGCGGTCA
AGCAGAGTTTCAGGCAGACACTGGAAGAACTTTGCCCTGGTCCCCCTTTTAAGAGAGGCA
AGTGCTCGAGATAGGCAGTCTGCTCAGCCCGAGGAAGTTTATCTGCGACAGTTTTCAGGG
TCTCTGAAGCCAGAGGACGCTGAGGTCTTCAAGAGTCCTGCCGCTTCCGGAGAGAAGTGA
```
ATG: Start codon of the gene (starting of ORF)
TGA: Stop codon of the gene (ending of ORF)
GGG→GGA: wobble done in reverse primer (Glycine to Glycine)

-continued

ATG → ATC: Reported single nucleotide polymorphism (SNP) in Genecard, Met--->Ile, SNP ID: rs222747.

A hybrid expression vector was created from two commercially-available vectors, as follows. Vector pTK-Hygro (Clonetech Cat No 631750) was digested with HindIII and AvaI to release the hygromycin cassette containing the TK promoter, the hygromycin gene and HSV-TK polyA signal. This hygromycin cassette was cloned into pcDNA4myc-HisB (Invitrogen Cat No V863-20) using the AvrII site. The hTRPV1 coding sequence was inserted into the resulting pcDNA Hygro vector at KpnI (5') and PmeI (3') sites and was thus flanked upstream by the cytomegalovirus promoter and downstream by the bovine growth hormone poly adenylation signal. Correct insertion of the entire ORF into the recombinant expression vector DNA (henceforth mentioned as DNA) was confirmed by sequence analysis. The complete plasmid backbone contains a pUC point of origin (ori), an ampicillin resistance gene, the pCMV promoter, a multiple cloning site containing KpnI and PmeI sites, an *E. coli* EM-7 promoter, and a hygromycin resistance gene in addition to the hTRPV1 ORF.

(ii) Development of Recombinant N1E115 Expressing hTRPV1

The following materials were used for the process:

Lipofectamine 2000 (Invitrogen, Cat #11668-019), Polyethyleneimine (Aldrich, Cat #340872), Hygromycin-B (Invitrogen, Cat#10687-010). Ultra pure kit prepared super-coiled DNA while the transfection carried out in antibiotic free, serum free DMEM.

For cell passage, N1E115 cells [American Type Culture Collection, Manassas, Va. (US), Accession number CRL2263] were cultured in Growth medium containing 1×DMEM (Sigma)+10% FBS (Gibco)+1% Penicillin-Streptomycin (Gibco) in 175 $cm^2$ flasks (Nunc). On the day of plating, spent media from the flasks was aspirated and the flasks were tapped from the sides with palms to dislodge the cells from the bottom of the flasks. Ten mL Growth media was added to suspend the cells and 1 mL of the suspended cells was inoculated in a fresh T-175 flask containing 35 mL Growth media.

Cell plating protocol for transfection was as follows: 0.2× $10^6$ cells in 2 mL growth medium was added to each well of a 6 well plates with lids inside the laminar air-flow. The plates were incubated at 37° C. and 5% $CO_2$ in a $CO_2$ incubator (Thermo) for 24 hours.

On the day of Lipofectamine mediated transfection, DNA and Lipofectamine were diluted in the laminar hood in the following way: 4 µg of DNA was diluted in 250 µL of DMEM. Next, 10 µg Lipofectamine was diluted in 250 µL of DMEM. The solutions were allowed to stand at room temperature (RT) for 7 minutes, after which they were mixed and allowed to stand at rt for another 20 minutes. Once the transfection mix was prepared, plated cells were washed with 500 µL DMEM. After washing, 500 µL of Lipofectamine-DNA mix was added to the wells. In control wells, Lipofectamine-DMEM was added and the plate was incubated at 37° C. and 5% $CO_2$ for 4.5 hours. After incubation, the media from transfected cells was carefully decanted without disturbing the cells. Cells were then washed once with 1 mL of DMEM. Growth media (DMEM+10% FBS) was added to the cells after washing and the cells were incubated at 37° C. and 5% $CO_2$ for 24 hours.

Twenty-four hours post incubations, the transfected cells were examined visually for viability and adherence. Spent media was removed from the wells and 1.2 mL fresh growth media containing 300 µg/mL hygromycin was added per well. The cells were dislodged by pipetting up and down. Cells from each well were split 1:4 and transferred to fresh 6 well plate (300 µL cells/well). Transfected cells and control cells were observed every day, spent media was changed every other day initially. By the end of second week transfected stable colonies would appear which were then expanded and tested functionally in a calcium assay and a sodium assay performed as follows.

(iii) Cell Passages and Clonal Isolation of Cells

The cell passage protocol described above was followed for passaging cells as before. And the clonal isolation by limiting dilution method was performed as described below.

Preparation of Feeder cells: Healthy looking N1E115 (wild type cells) were harvested. 1×$10^6$ cells/mL of N1E115 cells were treated with Mitomycin C at a concentration of 10 µg/L×$10^6$ cells for 20 minutes at 37° C. in a $CO_2$ incubator. After 20 minutes, cells were washed with DMEM 5-6 times. Cells were then transferred to a 75 $cm^2$ flask containing 15 mL of growth media and incubated at 37° C. for 4 hours in a $CO_2$ incubator. After incubation the feeder cells are washed with DMEM and cells became ready for plating.

Preparation of stable cells: Healthy looking cells of hTRPV1-N1E115 were pelleted down and resuspended in growth media in a concentration that if plated in a 96 well plate the distribution will be 0.3 cells/well/100 µL media. Selective antibiotic hygromycin b (300 µg/mL) was added to it.

Feeder cells were plated in 96 well plates at a concentration of 1000 cells/100 µL/well. Cells were not plated in the wells at the edges. Two hundred µL of sterile phosphate buffered saline (PBS) was added instead. To the feeder cell layer, 100 µL of the stable cell suspension containing 0.3 cells/well/100 µL was added. Plates were incubated at 37° C. and 5% $CO_2$. Plates were left undisturbed in $CO_2$ incubator for 10 days. From the $10^{th}$ day onwards, all the cell plates were observed very carefully for single colony (assumed to be generated from one single cell). Each and every well was checked carefully. The wells with only single colony were marked.

To the marked wells media change was given, spent media was discarded and fresh growth media containing 300 µg/mL hygromycin B was added. Marked wells with single colonies were expanded from 96 well plate to 48 well plate followed by 6 well plate. Finally the cells were transferred to 25 $cm^2$ flasks (5 mL growth media+300 µg/mL hygromycin B). From the cultured flasks cells were counted and plated for functional screening in Sodium and Calcium assay platforms. Final clonal candidate for the study was selected based on the assay data which confirmed a robust expression of hTRPV1 using a capsaicin-evoked calcium response in the calcium assay and no loss of the constitutive sodium channel activity as judged by a robust veratridine response in the membrane potential assay.

(iv) Calcium Assay to Assess hTRPV1-Expressing Cell Function

For the calcium assay, cells were plated at 5000 per 50 μL of DMEM+10% FBS+300 μg/mL hygromycin per well in a 384 clear-bottom poly-D-lysine coated plate and incubated at 37° C. and 5% $CO_2$ for 48 hours. On the day of the assay, media were discarded gently and washed with modified Tyrodes™ buffer (20 μL/well)] which was then discarded gently. See, Table 3.

TABLE 3

Composition of modified Tyrodes ™ buffer for calcium channel assay

| Salt | Concentration (mM) |
| --- | --- |
| NaCl | 145 |
| KCl | 2.5 |
| $CaCl_2$ 2 $H_2O$ | 5.4 |
| $MgCl_2$ 6 $H_2O$ | 1.2 |
| HEPES | 10 |
| Glucose | 10 (180 mg/100 mL) |
| Probenecid | 2.943 |

Volume was made up to 500 mL with Milli-Q water.

pH was adjusted to 7.4 with KOH.

Pluronic acid was added to Calcium 4 dye (Molecular Devices) at a concentration of 0.025% (250 μL of 1% stock for 10 mL of the dye). Next, 20 μL of Calcium 4 dye (Molecular Devices) prepared in modified Tyrodes buffer [Probenecid (42 mg in 60 μL 5N NaOH) was added to 50 mL modified Tyrodes buffer before pH adjustment] per well was added and the plate was incubated at 25° C. for 30 minutes before capsaicin addition [capsaicin stock was 20 mM in DMSO, working stock 1 mM (in buffer) and final concentration in assay plate was 10 μM] was utilized for calcium assay following manufacturer's instructions.] Twenty μL of 2×(20 μM) capsaicin was added to the cells in the FLIPR™ (Molecular Devices, Inc.) and read was taken for 15 minutes.

(v) Membrane potential Assay to Assess Sodium Channel Function in hTRPV1-Expressing Cells Cells were plated at 5000 per 50 μL [DMEM+10% FBS+ 300 μg/mL H\hygromycin] per well, in a 384 clear bottom poly-D-lysine coated plate and incubated at 37° C. and 5% $CO_2$ for 48 hours. On the day of the assay, media were discarded gently and 30 μL of the dye [FMP blue dye was prepared in assay buffer] per well was added and dye-loading was allowed to proceed for 20 min at room temperature. An 'agonist' drug-addition plate was prepared for the FLIPR™ instrument according to manufacturer's instructions; this plate contained both veratidine (Sigma-Aldrich, Cat No V5754) and Toxin-II from *Anemonia sulcata* (ATX-II, Sigma-Aldrich Cat No T3268). The concentrations of veratridine and ATX-II in the drug-addition plate were 400 μM and 12 μM, respectively in order to achieve final assay concentrations of 100 μM and 3 μM when 10 μL of the combined solution was dispensed into the cell plate using the FLIPR instrument. The agonist addition was programmed on the FLIPR™ to coincide with the initiation of fluorescence signal reading and such reads were taken at regular intervals for 10 minutes duration.

B. In Vitro Assay Developed for Assessing the Inhibition of Sodium Channel Response with Compounds Following Stimulation by Heat (47° C.) in Cells Expressing hTRPV1.

hTRPV1-N1E115 were passaged by culturing in Growth medium [containing 1×DMEM (Sigma)+10% FBS (Gibco)+ 1% Penicillin-Streptomycin (Gibco)+300 μg/mL Hygromycin B (Invitrogen, as the selection marker)] in 175 mL flasks (Nunc). The cells were split 1:10. Spent media from the flasks were aspirated and the flasks were tapped from sidewise with palms to dislodge the cells from the bottom of the flask. Growth media (10 mL) was added to suspend the cells and the suspended cells (1 mL) were inoculated in a fresh T-175 flask containing Growth media (35 mL). For plating the cells for the Assay, 5000 cells in 50 μL Growth medium was added to each well of 384-well, clear bottomed, sterile poly-D-lysine coated plates with lids (Greiner-bio one) inside the laminar air-flow. The plates were incubated at 37° C. and 5% $CO_2$ in a $CO_2$ incubator (Thermo). Forty eight hours later, on the day of the assay the cell seeded plates were observed under microscope to check the health, attachment and confluency of the monolayer prior to the assay.

The spent media from the cell seeded plates were decanted gently and FLIPR™ Membrane potential Dye-Blue (available commercially from Molecular Devices Inc., US, as is "FLIPR Membrane potential assay kit blue") was added into each well of the plates. The dye was prepared in assay buffer following manufacturer's instructions. The dye added plate was incubated at rt (25°) for 30 minutes inside a plate incubator (Thermo). Assay Buffer was prepared according to the following Table 4. The pH was adjusted to 7.4 with KOH (Sigma) and the volume was made up to 500 mL with Milli-Q® water (Millipore). Unless otherwise mentioned, all the dilutions were done in Assay Buffer.

TABLE 4

| Salt | Concentration (mM) |
| --- | --- |
| NaCl | 150 |
| KCl | 3.25 |
| $CaCl_2$ 2 $H_2O$ | 2 |
| $MgCl_2$ 6 $H_2O$ | 3 |
| HEPES | 10 |
| Glucose | 11 (198 mg/100 mL) |

The compounds were diluted in the Assay Buffer and added to 384 well-polypropylene round bottomed well plates (Costar) to serve as source plate for compound addition. After the dye incubation period was over, the dye loaded plates and the compound source plates were inserted inside the FLIPR$^{Tetra}$ (Molecular Devices, Inc.) with 384 FLIPR™ tip boxes (Molecular Devices, Inc.). The compounds were added to the dye loaded plates by the FLIPR$^{Tetra}$ (1st addition) system. After compound addition, the plates were immediately transferred to 47° C. plate incubator (Thermo) and incubated for 10 minutes to activate hTRPV1. The plates were then immediately transferred to 25° C. plate incubator (Thermo) and incubated for 30 minutes. The cell-seeded plates which were not to be activated were transferred to 25° C. plate incubator (Thermo) and incubated for 30 minutes. An agonist plate containing Veratridine (Sigma) and ATX-II was prepared, as described above, prior to the $2^{nd}$ addition. Agonist addition was achieved using FLIPR™ software and was timed to coincide with fluorescence readings that were taken at regular intervals for a total duration of 12 minutes.

The reference compound, QX-314 had a hTRPV1-N1E115, 47° C. $IC_{50}$ value of 733 mM in the FLIPR™ assay. An $IC_{50}$ of 100 μM indicates a 10 fold better activity than QX-314.

C. Method for Assessing the Extent of Inhibition of Sodium Channel Response with Compounds in hNav1.5-HEK293 Cells.

The following assay was used to assess the tendency of the test compounds to block the dominant cardiac sodium channel isoform. Nav1.5 sodium channels are known to be permeable to quaternary sodium channel blockers such as QX-314 and, thus, the assay was performed in the absence of a chemical TRPV1 agonist.

The hNav1.5-HEK-293 cells (CreaCell, France, a human embryonic kidney cell line expressing the human Nav1.5 sodium channel) were cultured in Growth medium (containing 1×DMEM (Gibco)+10% FBS (PAA Gold)+2% glutamine 100 mM (Gibco)+1% penicillin 10,000 U/mL streptomycin 10,000 µg/mL (Invitrogen)+1.2 mg/mL Geneticin® G418 (Invitrogen)) in 75 mL cell bind flasks (Corning). The following steps were followed exactly as mentioned. The spent medium was discarded and the cells rinsed once with PBS-1×. Accutase® (1-2 mL; PAA) solution was added. The plate was placed on a 37° C. warming incubator 3-5 minutes. As soon as cells are detached, 37° C. complete medium (9 mL) was added. The cell suspension is drawn into a sterile pipette and cells homogenized gently to dissociate cell aggregates. The cells were counted using a hemocytometer with Blue Trypan and then centrifuged 5 minutes at 400 g. The cells can be amplified or maintained by seeding 2,105 cells/mL in a T75 flask (final volume: 15 mL). 8000 cells in 50 µL Growth medium was added to each well of 384-well, clear bottomed, sterile poly-D-lysine coated plates with lid (Greiner-bio one) inside the laminar air-flow. The plates were incubated at 37° C. and 5% $CO_2$ in a $CO_2$ incubator (Thermo) for 48 hours.

On the day of the assay, cells were washed with Assay buffer, which was prepared using the components and amounts in the following Table 5. pH was adjusted to 7.4 with NaOH, volume made up to 500 mL with Milli-Q® water.

TABLE 5

| Salt | Concentration (mM) |
|---|---|
| NaCl | 165 |
| KCl | 4.5 |
| $CaCl_2$ $2H_2O$ | 2 |
| $MgCl_2$ $6H_2O$ | 1 |
| HEPES | 10 |
| Glucose | 10 (180 mg/100 mL) |

Assay Buffer was added to the cells and incubated at rt (25° C.) for 10 minutes. The compounds were diluted in assay buffer. The compounds were added and incubated at rt (25° C.) for 10 minutes. Red FMP Dye (MDC) was added to the cells and the plate was incubated at rt (25° C.) for 30 minutes. Veratridine stock (20 mM; Sigma) was prepared in DMSO; veratridine (final concentration of 30 µM) in assay buffer was added to each well of the cell seeded plates in the FLIPR and read taken for 10 minutes. The following table provides data illustrating the sodium channel activity of the test compounds in response to the presence or absence of heat stimulation in cells expressing hTRPV1. The compounds were tested for differential activity at 25° C. and 47° C. and at two test concentrations. Certain compounds were further evaluated for $IC_{50}$ in the 47° C. assay, and examples are shown in the following Table 6.

TABLE 6

| Ex | hTRPV1-N1E Nav 0.1 mM (% inhibition) | | hTRPV1-N1E Nav 1 mM (% inhibition) | | hTRPV1-N1E $IC_{50}$ (µM) |
|---|---|---|---|---|---|
|  | 25° C. | 47° C. | 25° C. | 47° C. | 47° C. |
| 1 | 13 (N = 4) | 73 (N = 4) | 53 (N = 4) | 92 (N = 4) | A' |
| 2 | 23 (N = 4) | 77 (N = 4) | 78 (N = 4) | 89 (N = 4) | A' |
| 3 | 14 (N = 2, 0.5 mM) | 19 (N = 2, 0.5 mM) | 52 (N = 2, 5 mM) | 67 (N = 2, 5 mM) | NT |
| 4 | 24 (N = 4) | 86 (N = 4) | NT | NT | A' |
| 5 | 45 (N = 4) | NT | NT | NT | A' |
| 6 | 24 (N = 2, 0.5 mM) | 80 (N = 2, 0.5 mM) | 58 (N = 2, 5 mM) | 92 (N = 2, 5 mM) | B' |
| 7 | 1 (N = 4) | 28 (N = 4) | 0 (N = 4) | 70 (N = 4) | NT |
| 8 | 14 (N = 4) | 38 (N = 4) | 22 (N = 4) | 53 (N = 4) | NT |
| 9 | 16 (N = 4) | 67 (N = 4) | NT | NT | NT |
| 10 | 10 (N = 4) | 59 (N = 4) | 61 (N = 4) | 95 (N = 4) | B' |
| 11 | 16 (N = 4) | 40 (N = 4) | NT | NT | B' |
| 12 | 25 (N = 4) | 84 (N = 4) | 17 (N = 4) | 88 (N = 4) | A' |
| 13 | 0 (N = 4) | 44 (N = 4) | 51 (N = 4) | 89 (N = 4) | A' |
| 14 | 0 (N = 4) | 31 (N = 4) | 10 (N = 4) | 66 (N = 4) | NT |
| 15 | 6 (N = 4) | 45 (N = 4) | 59 (N = 4) | 92 (N = 4) | B' |
| 16 | 31 (N = 4) | 60 (N = 4) | 50 (N = 4) | 83 (N = 4) | B' |
| 17 | 4 (N = 4) | 54 (N = 4) | 72 (N = 4) | 96 (N = 4) | B' |
| 18 | 3 (N = 4) | 41 (N = 4) | 28 (N = 4) | 66 (N = 4) | NT |
| 19 | 25 (N = 4) | NT | 12 (N = 4) | 52 (N = 4) | A' |
| 20 | 14 (N = 4) | 77 (N = 4) | 46 (N = 4) | 95 (N = 4) | A' |
| 21 | 11 (N = 4) | 57 (N = 4) | 35 (N = 4) | 96 (N = 4) | B' |
| 22 | 33 (N = 4) | NT | 91 (N = 4) | NT | A' |
| 23 | 38 (N = 4) | NT | 76 (N = 4) | NT | A' |
| 24 | 22 (N = 4) | NT | 81 (N = 4) | NT | A' |
| 25 | 48 (N = 4) | NT | 89 (N = 4) | NT | A' |
| 26 | 4 (N = 4) | 88 (N = 4) | 57 (N = 4) | 89 (N = 4) | A' |
| 27 | 23 (N = 4) | 73 (N = 4) | 74 (N = 4) | 85 (N = 4) | B' |
| 28 | 0 (N = 4) | 32 (N = 4) | 5 (N = 4) | 58 (N = 4) | NT |
| 29 | 36 (N = 4) | 52 (N = 4) | 50 (N = 4) | 61 (N = 4) | A' |
| 30 | 28 (N = 4) | 33 (N = 4) | 58 (N = 4) | 75 (N = 4) | NT |
| 31 | 27 (N = 4) | 94 (N = 4) | NT | NT | A' |
| 32 | 4 (N = 4) | 48 (N = 4) | 1 (N = 4) | 54 (N = 4) | NT |
| 33 | 3 (N = 4) | 36 (N = 4) | 23 (N = 4) | 57 (N = 4) | NT |

TABLE 6-continued

| | hTRPV1-N1E Nav 0.1 mM (% inhibition) | | hTRPV1-N1E Nav 1 mM (% inhibition) | | hTRPV1-N1E IC$_{50}$ (µM) |
|---|---|---|---|---|---|
| Ex | 25° C. | 47° C. | 25° C. | 47° C. | 47° C. |
| 34 | 35 (N = 4) | 36 (N = 4) | 35 (N = 4) | 55 (N = 4) | NT |
| 35 | 35 (N = 4) | 74 (N = 4) | NT | NT | A' |
| 36 | 50 (N = 4) | 83 (N = 4) | 84 (N = 4) | 95 (N = 4) | A' |
| 37 | 15 (N = 4) | 31 (N = 4) | 20 (N = 4) | 70 (N = 4) | NT |
| 38 | 75 (N = 4) | 95 (N = 4) | NT | NT | A' |
| 39 | 41 (N = 4) | 7 (N = 4) | NT | NT | A' |
| 40 | 10 (N = 4) | 43 (N = 4) | 12 (N = 4) | 80 (N = 4) | NT |
| 41 | 13 (N = 4) | 66 (N = 4) | 22 (N = 4) | 89 (N = 4) | A' |
| 42 | 8 (N = 4) | 45 (N = 4) | 16 (N = 4) | 90 (N = 4) | A' |
| 43 | 13 (N = 4) | 78 (N = 4) | NT | NT | A' |
| 44 | 56 (N = 4) | 89 (N = 4) | 81 (N = 4) | 96 (N = 4) | NT |
| 45 | 4 (N = 4) | 72 (N = 4) | 46 (N = 4) | 83 (N = 4) | A' |
| 46 | 40 (N = 4) | NT | NT | NT | A' |
| 47 | 54 (N = 4) | NT | NT | NT | A' |
| 48 | 48 (N = 4) | NT | NT | NT | A' |

A': IC$_{50}$ = 10-100 µM
B': IC$_{50}$ = 100-1000 µM
NT: Not tested

Similarly, the following Table 7 provides data illustrating the sodium channel activity of test compounds that showed a prominent inhibition of response at 47° C. together with minimal inhibition at 25° C. These compounds were assessed for their ability to block the cardiac sodium channel in a cell expressing Nav1.5. Data for several such compounds are shown in FIG. 1, the concentrations of these compounds required to block NaV1.5 are shown to be higher than those required to block the sodium channel response in the TRPV1-N1E115 cell line.

TABLE 7

| Ex | HEK Nay 1.5% inh. @ 0.5 mM | HEK Nav 1.5% inh. @ 1.5 mM | HEK Nav 1.5 IC$_{50}$ (µM) (AVG) |
|---|---|---|---|
| 1 | NT | NT | 240 |
| 2 | NT | NT | 188 |
| 5 | NT | NT | 305 |
| 6 | 30 | 68 | 684 |
| 12 | NT | NT | 134 |
| 31 | NT | NT | 160 |
| 38 | NT | NT | 54 |
| 39 | NT | NT | 89 |
| 46 | NT | NT | 232 |
| 47 | NT | NT | 255 |
| 48 | NT | NT | 252 |

Example 50

In Vivo Assay of Mechanical Nociception

This assay was performed to monitor the time course of analgesia when compounds were injected either alone, or in combination with lidocaine directly into the vicinity of the sciatic nerve.

Male Sprague Dawley (SD) rats were of 180-220 gram body weight range. Animals were acclimatized for three days with the laboratory technician and the experimental environment. At day 1, all animals were given three sessions of acclimatization with the laboratory (30-45 minutes) and being wrapped in a towel (1 minute per animal). At day 2, the same acclimatization schedule was followed along with pincher touch (application without force) in session 3. At day 3, an acclimatization schedule similar to that of day 2 was followed and the first baseline was recorded. At day 4, the second baseline was recorded before administering the drug/test compound injection. The second baseline was considered for evaluation of treatment effect.

Withdrawal/Vocalization Force threshold (PWF) of the ipsilateral (right hind) paw were recorded for all the animals in morning of the experimentation day. The pincher was applied at the base of last phalange, somewhere at the midway of 5$^{th}$ and 4$^{th}$ metatarsus, with a cut-off of 500 grams. The forceps' arms of the pincher were kept in a fashion that the gauged end faced the dorsum of the paw and flat end faced the plantar surface. Force application with pincher arms was done in a fashion to increase slowly and steadily. Force application speed was optimized with practice to reach the cut off value (500 g) in approximately 6-7 seconds.

For the injection, rats were anesthetized with isoflurane (obtained from Baxter Pharma, US) for a brief period and held in the prone position with the limbs splayed. The greater trochanter and ischial tuberosity were localized by palpation and an imaginary line was drawn between the two and a point was estimated on that line at about one third of the distance caudal to the greater trochanter. Respective test compound/vehicle solution (about 100 µL or 200 µL, separate experiments) was injected with the injection needle advanced from a dorsolateral direction at a 45° angle and the needle tip touching the ischium. A 27 gauge needle connected to a tuberculin syringe was used for the injection. Injection volume was pushed gently. Post injection, the animals were kept in the recovery chamber and only after complete recovery from anesthesia were they returned to the cages. Care was taken that mild anesthesia was given so that the animals remain anesthetized for a very brief time.

Test compounds were formulated at required concentrations (0-15%) in a normal physiological saline vehicle (0.9% sodium chloride) to provide the solution formulation. Lidocaine.HCl powder (Sigma, USA) was then dissolved in the same solution to provide a combination solution formulation of test compound and lidocaine. Sonication was used to reduce the particle size if required—as judged by visual inspection of the solution. The final formulation was filter sterilized with syringe top filters (0.22 µm) prior to administration.

On day 4, after compound/vehicle injection, the two readouts of PWL were taken at 0.5 and 2 hours post injection followed by readouts at intervals of 1 hour or 2 hours depending upon whether the response remained at cut-off or showed signs of regained sensitivity. Recordings were continued until the gram-force response declined to a level that was not significantly different from pre-drug baseline. Otherwise, recordings were continued up to 14 hours, followed by the next readout on day 5 at 24 hours post injection. When significant anti-nociception effect was still observed at 24 hours, recordings were further continued as on day 4.

GraphPad® Prism 5 statistical software was used for analysis. Under column analysis, one way analysis of variance (ANOVA) was performed for each group followed by Dunnett's test for checking the significance of difference between baseline values and readouts at different time points.
A. Comparison of Compounds with QX-314

Figure 2:
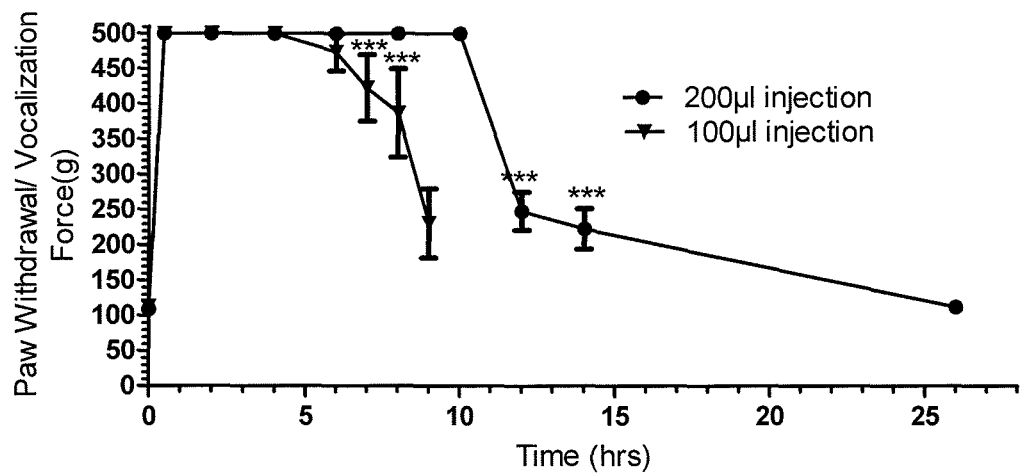

Using the summary and assay provided above, the formulations of the following Table 8 were prepared and tested. The results of these assays are provided in FIGS. 1 and 2 and summarized in the following table. Specifically, FIGS. 1 and 2 are plots of paw withdrawal vocalization force (g) vs. time (hours).

TABLE 8

Duration of Analgesia for Mechanical Nociception

| Test Compound Example | Test Compound Amount (%) | Lidocaine Amount (%) | Total Injection Amount (µL) | Average Time of Analgesia (h) |
|---|---|---|---|---|
| 6 | 0.5 | 2 | 200 | 14 |
|   |   | 2 | 200 | 10 |
|   |   | 0 | 200 | 5 |
|   |   | 2 | 100 | 8 |
| 1 | 0.5 | 2 | 100 | 7 |
|   |   | 2 | 200 | 8 |
|   |   | 2 | 200 | 14 |
|   |   | 2 | 200 | 12 |
|   |   | 2 | 200 | 6 |
| 2 | 0.5 | 2 | 200 | 12 |
| 12 | 0.5 | 2 | 200 | 0.5 |
| 5 | 0.2 | 2 | 200 | 2 |
|   | 0.3 | 2 | 200 | 24 |
|   | 0.4 | 2 | 200 | 44 |
|   | 0.45 | 2 | 200 | >64 |
|   | 0.5 | 2 | 200 |   |
| 46 | 0.5 | 2 | 200 | 24 |
| 47 | 0.5 | 2 | 200 | 24 |

These data illustrate that the compounds of examples 1, 2, 5, 6 and 12 provided analgesic effects for at least 7 hours, which is greater than QX-314. Of significance, the compound of example 6 provided analgesic effects of significant duration in the absence of lidocaine.
C. Effect of Injection Volume and Concentration Injections were prepared according to the description provided above and included (i) 100 µL of a solution containing 0.5% of the compound of example 6 and 2% lidocaine and (ii) 200 µL of a solution containing 0.5% of the compound of example 6 and 2% lidocaine. These injections were administered as described above, thereby permitting analysis of the effect of 100 µL vs. 200 µL volumes of the formulation.

The results of these assays are provided in FIGS. 1 and 2. Specifically, FIGS. 1 and 2 are plots of paw withdrawal vocalization force (g) vs. time (hours). It is noted that at test compound amounts of 0.5%, the overall duration of dense analgesia (i.e. 500 g of exerted force) was shorter for 100 µL compared to 200 µL injection volumes as was the overall period of analgesia—as defined by the last time point at which statistically significant differences from baseline responses were obtained.

Example 52

Topical Anesthetic Activity

Aliquots (0.25 mL) of test solutions are applied into the conjunctival sac of conscious rabbits (either sex; 2-4 kg) and the eye-lids are kept closed for about 20 seconds. The corneal reflex is checked before application of the test solution and every 5 minutes thereafter. To test the corneal reflex, the cornea is touched six times with a stalked elastic bristle. The duration of anesthesia is calculated as the period from the time-point when the animal does not feel any of the six touches by the bristle to the time point when the animal again reacts to three of the six touches. To verify the reversibility of the topical anesthetic effect, the testing continues until the animal reacts to all six touches of the bristle for at least 15 minutes.

Example 53

Dermal Anesthetic Activity

About 18 to 24 hours before each experiment, the skin on the back of male guinea pigs is shaved and depilated with a commercially available hair remover. The anesthetic action of each agent following dermal application is determined using a "pin-prick" method as described by Aberg (Acta Pharmacol Toxicol, 273-286). Before and at various intervals after treatment, the area of the skin is tested for the presence or absence of a skin twitch in response to six standardized dermal probings with a pointed metal "algesimeter" at a predetermined maximum load of 10 g. The average number of probings not producing a skin twitch response is designated as the "anesthetic score".

In this system six responses to six stimuli represents "no anesthetic activity" and no response to six stimuli represents a "maximal anesthetic activity". In experiments on the dermal anesthetic activity, a single area of skin 1 inch square is marked off on the middle of the back of each animal. This area is covered by a 1 inch square, 16 layer thick gauze pad onto which is deposited 0.45 mL of a 10% solution of the test agent in water with DMSO. The gauze pad is covered with a five inch square sheet of Saran Wrap which is attached to the surrounding skin with tape. The entire area is then covered by wrapping an elastic bandage around the trunk of the animal. After a predetermined duration of treatment, the coverings are removed and the skin assessed for the presence of anesthesia as described above. Dermal anesthesia tests are performed at ten minute intervals to measure onset time and duration of dermal anesthetic activity; comparisons are made with reference compounds and vehicle.

Example 54

C. Local (Infiltration) Anesthetic Activity

About 18-24 hours before each experiment, the skin on the back of male guinea pigs is prepared according to Example 53. The anesthetic action of each agent following intradermal injection is determined using a "pin-prick" method similar to that described in Example 53. Before and at various intervals after treatment, the area of the skin is tested for the presence or absence of a skin twitch in response to six standardized cutaneous probings with a pointed metal "algesimeter" at a predetermined maximum force of 20 grams. The average number of probings not producing a skin twitch response is designated as the "anesthetic score". In this system, six responses to six stimuli represent "no anesthetic activity" and no response to six stimuli represents a "maximal anesthetic activity". In experiments with intradermal injections of agents, the backs of the guinea pigs are divided into four sections using a marking pen, and injections of 0.1 mL of 0.25%, 0.5% and 1.0% solutions of the test compounds in physiological saline, vehicle (physiological saline) and at least one reference compounds are made, one injection into each of the four defined areas.

Example 55

Acute Intravenous Toxicity in Mice

Mice (males) of the NMRI strain, weighing 20 to 22 g are used after a stabilization period of at least ten days at the testing facility and at least one hour in the laboratory. Food but not water is withheld from all animals for 16 hours before the test. The animals are given free access to food starting two hours after the drug administration, that usually takes place around 9.00 AM. All animals are observed daily for 7 days post dosing.

Example 56

In Vitro Assay for Effect of Compounds on Bladder Detrusor Muscle

This study assesses the effects of test compounds described herein on the contractile response of isolated detrusor muscle (Iravani & Zar, British Journal of Pharmacology 1994, 113: 95-102).

Urinary bladder smooth muscle strips are obtained from female guinea-pigs (Dunkin-Hartley strain, body weight 300-350 g). Bladder strips are prepared and connected to tension transducers in 5 mL organ baths containing Krebs-Henseleit solution (kept at 37° C., pH 7.4, gassed with 95% $O_2$/5% $CO_2$). Strips are equilibrated for at least 60 minutes at 1.0 g resting tension, during which tissues are washed every 15 minutes. Each strip is then exposed to 80 mM KCl to verify viability. Following a 30 minute period of equilibration and washout, detrusor muscle strips are subjected to electrical-field stimulation (EFS parameters: 800 mA, frequency of 15 Hz, pulse duration 0.1 ms, train of pulses 4 seconds every 2 minutes).

After approximately 20-25 minutes (stabilization), a cumulative concentration-response curve (CRC) is constructed by adding (i) about 0.001 to about 0.108% of a compound described herein and about 0.00025 to about 0.03325% of lidocaine (Experiment 1) or (ii) about 0.00003 to about 0.10843% of a compound described herein and about 0.0001 to about 0.01333% lidocaine (Experiment 2) to the organ bath. At the end of the CRC, 1 μM tetrodotoxin (TTX) is added to confirm the neurogenic origin of contractions. The results will be expressed as % variation from basal EFS-induced contractions.

It is anticipated that both lidocaine and the compounds described herein will produce concentration-dependent inhibitions of EFS-induced detrusor contractions. It is also anticipated that exposure of the detrusor tissue to a combination of lidocaine plus the test compound will result in a concentration-inhibition relationship suggesting that the two drugs will act in an additive manner to inhibit the contractile response.

Example 57

Sustained Inhibition of EFS-Induced Bladder Contractions

This example was performed to show the sustainability of the compounds discussed herein in inhibiting EFS-induced bladder contractions.

The EFS treated urinary bladder smooth muscle strips are prepared as described in the first paragraph of Example 58. After approximately 20-25 minutes (stabilization), a single concentration of lidocaine (0.01 or 0.003%), a compound described herein (0.01% or 0.0004%) or solvent is added. After obtaining a maximal effect (approximately 15 minutes), all preparations are washed four times. EFS-induced contractions are then recorded for 120 minutes. The amplitudes of EFS-induced contractions during the recovery period are expressed as % of basal EFS-induced contractions (before treatment). Analysis is performed at 5, 15, 30, 60 and 120 minutes after the end of the washout period.

It is anticipated that the data will suggest that the test compound acts on the bladder detrusor muscle to inhibit contractility and this effect will be slow to reverse.

Example 58

In Vivo Assay of Bladder Function

This study assesses the effects of compounds described herein on various aspects of bladder function in conscious rats.

Rats are prepared with indwelling polyethylene catheters positioned into the bladder through the dome and exteriorized at the scapular level. Intracysternal pressure is monitored by connecting the catheter to a commercial strain gauge via a T-connector that permits the infusion of solutions and drugs. Cystometric recording will commence 48 hours after catheter implantation. Animals are continuously administered saline, with or without test compounds, through the catheter, at a rate of 2 mL/hr. Urine is collected and weighed using a force transducer and intravesical pressure is continually monitored in order to assess micturition amplitude, frequency and volume and bladder capacity. Saline perfusions are supplemented with the test compound in order to determine the effects on each of the above bladder function parameters.

The infusion of a solution of a test compound described herein is anticipated to produce an increase in bladder capacity and a decrease in micturition volume after administration. An infusion of a combined solution of the test compound with 2% lidocaine is anticipated to result in the suppression of micturition and a corresponding rise in intravesical pressure. In is finally anticipated that, compared to lidocaine alone, the test compound will have a longer duration of action on micturition frequency.

In summary, it is anticipated that the compounds described herein will change bladder function and will have therapeutic benefit to patients suffering from disease or pathological conditions that lead, directly or indirectly, to overactive bladder and/or interstitial cystitis (painful bladder syndrome), irritable bowel syndrome or chemical sensitivities.

All publications cited in this specification and priority applications, i.e., U.S. Provisional Patent Application Nos. 61/550,489, filed Oct. 24, 2011, and 61/683,519, filed Aug.

15, 2012, are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method of treating pain in a patient, comprising administering to said patient a therapeutically effective amount of a compound selected from the group consisting of:
N-[2-((2,6-Dimethylbenzoyl)oxy)propyl]-N,N-dimethyl-cyclohexanaminium iodide.
N-[2-(Benzoyloxy)propyl]-N,N-diethylcyclohexan-aminium chloride;
N,N-Dimethyl-N-[2-((2,4,6-trimethylbenzoyl)oxy)pro-pyl]cyclohexanaminium iodide;
N-[2-((2,6-Dimethoxybenzoyl)oxy)propyl]-N,N-dimeth-ylcyclohexanaminium iodide;
N-[2-((2-Fluorobenzoyl)oxy)propyl]-N,N-dimethylcy-clohexanaminium iodide;
N-[2-((2-Chlorobenzoyl)oxy)propyl]-N,N-dimethylcy-clohexanaminium iodide;
N-[2-((2,4-Dichlorobenzoyl)oxy)propyl]-N,N-dimethyl-cyclohexanaminium iodide;
N,N-Dimethyl-N-[2-((2-methylbenzoyl)oxy)propyl]cy-clohexanaminium iodide;
N-[2-((2-Isopropylbenzoyl)oxy)propyl]-N,N-dimethylcy-clohexanaminium iodide;
N-[2-((4-(tert-Butyl)benzoyl)oxy)propyl]-N,N-dimethyl-cyclohexanaminium iodide;
N-[2-((4-Chlorobenzoyl)oxy)propyl]-N,N-dimethylcy-clohexanaminium iodide;
N-[2-((3-Fluorobenzoyl)oxy)propyl]-N,N-dimethylcy-clohexanaminium iodide;
N-[2-((4-Fluoro-2-(trifluoromethyl)benzoyl)oxy)propyl]-N,N-dimethylcyclohexanaminium iodide;
N,N-Dimethyl-N-[2-((3-(trifluoromethyl)benzoyl)oxy) propyl]cyclohexanaminium iodide;
N-[2-((2-(Trifluoromethyl)benzoyl)oxy)propyl]-N,N-dimethylcyclohexanaminium iodide;
N,N-Dimethyl-N-[2-((2-nitrobenzoyl)oxy)propyl]cyclo-hexanaminium iodide;
N-[2-((3,5-Dichlorobenzoyl)oxy)propyl]-N,N-dimethyl-cyclohexanaminium iodide;
N-[2-((4-Ethylbenzoyl)oxy)propyl]-N,N-dimethylcyclo-hexanaminium iodide;
N,N-Dimethyl-N-[2-((4-(trifluoromethyl)benzoyl)oxy) propyl]cyclohexanaminium iodide;
(S)—N,N-Dimethyl-N-[2-((2,4,6-trimethylbenzoyl)oxy) propyl]cyclohexanaminium iodide;

(S)—N-[2-((2,6-Dimethylbenzoyl)oxy)propyl]-N,N-dimethylcyclohexanaminium iodide;
(R)—N-[2-((2,6-Dimethylbenzoyl)oxy)propyl]-N,N-dimethylcyclohexanaminium iodide;
(R)—N,N-Dimethyl-N-[2-((2,4,6-trimethylbenzoyl)oxy)propyl]cyclohexanaminium iodide;
N-[2-((3-Isopropylbenzoyl)oxy)propyl]-N,N-dimethylcyclohexanaminium iodide;
N-[2-((2,6-Dichlorobenzoyl)oxy)propyl]-N,N-dimethylcyclohexanaminium iodide;
N,N-Dimethyl-N-[2-((2,4,6-trimethylbenzoyl)oxy)propyl]tetrahydro-2H-pyran-4-aminium iodide;
N-[2-((2,3-Dichlorobenzoyl)oxy)propyl]-N,N-dimethylcyclohexanaminium iodide;
N-[2-((Cyclohexanecarbonyl)oxy)propyl]-N,N-diethylcyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;
N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;
N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-((3-methylthiophene-2-carbonyl)oxy)propyl]cyclohexanaminium iodide;
N-[2-((4-(tert-Butyl)benzoyl)oxy)propyl]-N,N,4-trimethylcyclohexanaminium iodide;
N,N,4-Trimethyl-N-[2-((2,4,6-trimethylbenzoyl)oxy)propyl]cyclohexanaminium iodide;
N-[2-((2,6-Dimethylbenzoyl)oxy)ethyl]-N,N-dimethylcyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethylcyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl]-N,N-dimethylcyclohexanaminium iodide;
(S)—N-[2-((4-(tert-Butyl)benzoyl)oxy)propyl]-N,N-dimethylcyclohexanaminium iodide;
(R)—N-[2-((4-(tert-Butyl)benzoyl)oxy)propyl]-N,N-dimethylcyclohexanaminium iodide;
(S)—N-[2-((4-(tert-Butyl)benzoyl)oxy)propyl]-N,N-dimethylcyclohexanaminium bromide;
(R)—N-[2-((4-(tert-Butyl)benzoyl)oxy)propyl]-N,N-dimethylcyclohexanaminium bromide;
1-Cyclohexyl-1-[2-((2-isopropylbenzoyl)oxy)propyl]pyrrolidin-1-ium bromide;
1-Cyclohexyl-1-[2-((2-isopropylbenzoyl)oxy)propyl]piperidin-1-ium bromide;
1-[2-((4-(tert-Butyl)benzoyl)oxy)propyl]-1-cyclohexylpyrrolidin-1-ium bromide;
1-[2-((4-(tert-Butyl)benzoyl)oxy)propyl]-1-cyclohexylpiperidin-1-ium bromide;
1-[2-((3-Chlorobenzo[b]thiophene-2-carbonyl)oxy)propyl]-1-cyclohexylpyrrolidin-1-ium bromide; and
1-[2-((3-Chlorobenzo[b]thiophene-2-carbonyl)oxy)propyl]-1-cyclohexylpiperidin-1-ium bromide.

2. The method of claim 1, wherein said administration is topical.

3. A method of treating pain in a patient, comprising administering to said patient a therapeutically effective amount of a compound selected from the group consisting of:
(i) N-[2-((2,6-Dimethylbenzoyl)oxy)propyl]-N,N-dimethylcyclohexanaminium iodide;
N-[2-(Benzoyloxy)propyl]-N,N-diethylcyclohexanaminium chloride;
N,N-Dimethyl-N-[2-((2,4,6-trimethylbenzoyl)oxy)propyl]cyclohexanaminium iodide;
N-[2-((2,6-Dimethoxybenzoyl)oxy)propyl]-N,N-dimethylcyclohexanaminium iodide;
N-[2-((2-Fluorobenzoyl)oxy)propyl]-N,N-dimethylcyclohexanaminium iodide;
N-[2-((2-Chlorobenzoyl)oxy)propyl]-N,N-dimethylcyclohexanaminium iodide;
N-[2-((2,4-Dichlorobenzoyl)oxy)propyl]-N,N-dimethylcyclohexanaminium iodide;
N,N-Dimethyl-N-[2-((2-methylbenzoyl)oxy)propyl]cyclohexanaminium iodide;
N-[2-((2-Isopropylbenzoyl)oxy)propyl]-N,N-dimethylcyclohexanaminium iodide;
N-[2-((4-(tert-Butyl)benzoyl)oxy)propyl]-N,N-dimethylcyclohexanaminium iodide;
N-[2-((4-Chlorobenzoyl)oxy)propyl]-N,N-dimethylcyclohexanaminium iodide;
N-[2-((3-Fluorobenzoyl)oxy)propyl]-N,N-dimethylcyclohexanaminium iodide;
N-[2-((4-Fluoro-2-(trifluoromethyl)benzoyl)oxy)propyl]-N,N-dimethylcyclohexanaminium iodide;
N,N-Dimethyl-N-[2-((3-(trifluoromethyl)benzoyl)oxy)propyl]cyclohexanaminium iodide;
N-[2-((2-(Trifluoromethyl)benzoyl)oxy)propyl]-N,N-dimethylcyclohexanaminium iodide;
N,N-Dimethyl-N-[2-((2-nitrobenzoyl)oxy)propyl]cyclohexanaminium iodide;
N-[2-((3,5-Dichlorobenzoyl)oxy)propyl]-N,N-dimethylcyclohexanaminium iodide;
N-[2-((4-Ethylbenzoyl)oxy)propyl]-N,N-dimethylcyclohexanaminium iodide;
N,N-Dimethyl-N-[2-((4-(trifluoromethyl)benzoyl)oxy)propyl]cyclohexanaminium iodide;
(S)—N,N-Dimethyl-N-[2-((2,4,6-trimethylbenzoyl)oxy)propyl]cyclohexanaminium iodide;
(S)—N-[2-((2,6-Dimethylbenzoyl)oxy)propyl]-N,N-dimethylcyclohexanaminium iodide;
(R)—N-[2-((2,6-Dimethylbenzoyl)oxy)propyl]-N,N-dimethylcyclohexanaminium iodide;
(R)—N,N-Dimethyl-N-[2-((2,4,6-trimethylbenzoyl)oxy)propyl]cyclohexanaminium iodide;
N-[2-((3-Isopropylbenzoyl)oxy)propyl]-N,N-dimethylcyclohexanaminium iodide;
N-[2-((2,6-Dichlorobenzoyl)oxy)propyl]-N,N-dimethylcyclohexanaminium iodide;
N,N-Dimethyl-N-[2-((2,4,6-trimethylbenzoyl)oxy)propyl]tetrahydro-2H-pyran-4-aminium iodide;
N-[2-((2,3-Dichlorobenzoyl)oxy)propyl]-N,N-dimethylcyclohexanaminium iodide;
N-[2-((Cyclohexanecarbonyl)oxy)propyl]-N,N-diethylcyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;

N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;
N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-((3-methylthiophene-2-carbonyl)oxy)propyl]cyclohexanaminium iodide;
N-[2-((4-(tert-Butyl)benzoyl)oxy)propyl]-N,N,4-trimethylcyclohexanaminium iodide;
N,N,4-Trimethyl-N-[2-((2,4,6-trimethylbenzoyl)oxy)propyl]cyclohexanaminium iodide;
N-[2-((2,6-Dimethylbenzoyl)oxy)ethyl]-N,N-dimethylcyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethylcyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl]-N,N-dimethylcyclohexanaminium iodide;
(S)—N-[2-((4-(tert-Butyl)benzoyl)oxy)propyl]-N,N-dimethylcyclohexanaminium iodide;
(R)—N-[2-((4-(tert-Butyl)benzoyl)oxy)propyl]-N,N-dimethylcyclohexanaminium iodide;
(S)—N-[2-((4-(tert-Butyl)benzoyl)oxy)propyl]-N,N-dimethylcyclohexanaminium bromide;
(R)—N-[2-((4-(tert-Butyl)benzoyl)oxy)propyl]-N,N-dimethylcyclohexanaminium bromide;
1-Cyclohexyl-1-[2-((2-isopropylbenzoyl)oxy)propyl]pyrrolidin-1-ium bromide;
1-Cyclohexyl-1-[2-((2-isopropylbenzoyl)oxy)propyl]piperidin-1-ium bromide;
1-[2-((4-(tert-Butyl)benzoyl)oxy)propyl]-1-cyclohexylpyrrolidin-1-ium bromide;
1-[2-((4-(tert-Butyl)benzoyl)oxy)propyl]-1-cyclohexylpiperidin-1-ium bromide;
1-[2-((3-Chlorobenzo[b]thiophene-2-carbonyl)oxy)propyl]-1-cyclohexylpyrrolidin-1-ium bromide; and
1-[2-((3-Chlorobenzo[b]thiophene-2-carbonyl)oxy)propyl]-1-cyclohexylpiperidin-1-ium bromide; and
(ii) a TRPV1 receptor activator.

4. The method of claim 3, wherein said TRPV1 receptor activator is selected from the group consisting of capsaicin, dihydrocapsaicin, nordihydrocapsaicin, lidocaine, articaine, procaine, tetracaine, mepivicaine, bupivicaine, eugenol, camphor, clotrimazole, N-arachidonoylvanillamine, anandamide, 2-aminoethoxydiphenyl borate, AM404, resiniferatoxin, phorbol 12-phenylacetate 13-acetate 20-homovanillate, olvanil, N-oleoyldopamine, N-arachidonyldopamine, 6'-iodoresiniferatoxin, a $C_{18}$ N-acylethanolamine, a lipoxygenase derivative, nonivamide, a fatty acyl amide of a tetrahydroisoquinoline inhibitor cysteine knot peptide, N-[2-(3,4-dimethylbenzyl)-3-(pivaloyloxy)propyl]-2-[4-(2-aminoethoxy)-3-methoxyphenyl]acetamide, N-[2-(3,4-dimethylbenzyl)-3-(pivaloyloxy)propyl]-N'-(4-hydroxy-3-methoxybenzyl)thiourea, hydroxy-α-sanshool, 2-aminoethoxydiphenyl borate, 10-shogaol, oleylgingerol, oleylshogaol, N-(4-tert-butylbenzyl)-N'-(4-hydroxy-3-methoxybenzyl)thiourea, aprindine, benzocaine, butacaine, cocaine, dibucaine, encainide, mexiletine, oxetacaine, prilocaine, proparacaine, procainamide, n-acetylprocainamide, chloroprocaine, dyclonine, etidocaine, levobupivacaine, ropivacaine, cyclomethycaine, dimethocaine, propoxycaine, trimecaine, and sympocaine.

5. The method of claim 3 or 4, wherein said administration is topical.

6. The method of claim 3, wherein said TRPV1 receptor activator of (ii) is co-administered with said compound of (i).

7. The method of claim 3, wherein said TRPV1 receptor activator of (ii) is administered prior to said compound of (i).

8. A method of treating itch in a patient, comprising administering to said patient a therapeutically effective amount of a compound selected from the group consisting of:
N-[2-((2,6-Dimethylbenzoyl)oxy)propyl]-N,N-dimethylcyclohexanaminium iodide;
N-[2-(Benzoyloxy)propyl]-N,N-diethylcyclohexanaminium chloride;
N,N-Dimethyl-N-[2-((2,4,6-trimethylbenzoyl)oxy)propyl]cyclohexanaminium iodide;
N-[2-((2,6-Dimethoxybenzoyl)oxy)propyl]-N,N-dimethylcyclohexanaminium iodide;
N-[2-((2-Fluorobenzoyl)oxy)propyl]-N,N-dimethylcyclohexanaminium iodide;
N-[2-((2-Chlorobenzoyl)oxy)propyl]-N,N-dimethylcyclohexanaminium iodide;
N-[2-((2,4-Dichlorobenzoyl)oxy)propyl]-N,N-dimethylcyclohexanaminium iodide;
N,N-Dimethyl-N-[2-((2-methylbenzoyl)oxy)propyl]cyclohexanaminium iodide;
N-[2-((2-Isopropylbenzoyl)oxy)propyl]-N,N-dimethylcyclohexanaminium iodide;
N-[2-((4-(tert-Butyl)benzoyl)oxy)propyl]-N,N-dimethylcyclohexanaminium iodide;
N-[2-((4-Chlorobenzoyl)oxy)propyl]-N,N-dimethylcyclohexanaminium iodide;
N-[2-((3-Fluorobenzoyl)oxy)propyl]-N,N-dimethylcyclohexanaminium iodide;
N-[2-((4-Fluoro-2-(trifluoromethyl)benzoyl)oxy)propyl]-N,N-dimethylcyclohexanaminium iodide;
N,N-Dimethyl-N-[2-((3-(trifluoromethyl)benzoyl)oxy)propyl]cyclohexanaminium iodide;
N-[2-((2-(Trifluoromethyl)benzoyl)oxy)propyl]-N,N-dimethylcyclohexanaminium iodide;
N,N-Dimethyl-N-[2-((2-nitrobenzoyl)oxy)propyl]cyclohexanaminium iodide;
N-[2-((3,5-Dichlorobenzoyl)oxy)propyl]-N,N-dimethylcyclohexanaminium iodide;
N-[2-((4-Ethylbenzoyl)oxy)propyl]-N,N-dimethylcyclohexanaminium iodide;
N,N-Dimethyl-N-[2-((4-(trifluoromethyl)benzoyl)oxy)propyl]cyclohexanaminium iodide;
(S)—N,N-Dimethyl-N-[2-((2,4,6-trimethylbenzoyl)oxy)propyl]cyclohexanaminium iodide;
(S)—N-[2-((2,6-Dimethylbenzoyl)oxy)propyl]-N,N-dimethylcyclohexanaminium iodide;
(R)—N-[2-((2,6-Dimethylbenzoyl)oxy)propyl]-N,N-dimethylcyclohexanaminium iodide;
(R)—N,N-Dimethyl-N-[2-((2,4,6-trimethylbenzoyl)oxy)propyl]cyclohexanaminium iodide;
N-[2-((3-Isopropylbenzoyl)oxy)propyl]-N,N-dimethylcyclohexanaminium iodide;
N-[2-((2,6-Dichlorobenzoyl)oxy)propyl]-N,N-dimethylcyclohexanaminium iodide;
N,N-Dimethyl-N-[2-((2,4,6-trimethylbenzoyl)oxy)propyl]tetrahydro-2H-pyran-4-aminium iodide;

N-[2-((2,3-Dichlorobenzoyl)oxy)propyl]-N,N-dimethyl-cyclohexanaminium iodide;
N-[2-((Cyclohexanecarbonyl)oxy)propyl]-N,N-diethyl-cyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;
N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;
N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-((3-methylthiophene-2-carbonyl)oxy)propyl]cyclohexanaminium iodide;
N-[2-((4-(tert-Butyl)benzoyl)oxy)propyl]-N,N,4-trimethylcyclohexanaminium iodide;
N,N,4-Trimethyl-N-[2-((2,4,6-trimethylbenzoyl)oxy)propyl]cyclohexanaminium iodide;
N-[2-((2,6-Dimethylbenzoyl)oxy)ethyl]-N,N-dimethyl-cyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethyl-cyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl]-N,N-dimethyl-cyclohexanaminium iodide;
(S)—N-[2-((4-(tert-Butyl)benzoyl)oxy)propyl]-N,N-dimethylcyclohexanaminium iodide;
(R)—N-[2-((4-(tert-Butyl)benzoyl)oxy)propyl]-N,N-dimethylcyclohexanaminium iodide;
(S)—N-[2-((4-(tert-Butyl)benzoyl)oxy)propyl]-N,N-dimethylcyclohexanaminium bromide;
(R)—N-[2-((4-(tert-Butyl)benzoyl)oxy)propyl]-N,N-dimethylcyclohexanaminium bromide;
1-Cyclohexyl-1-[2-((2-isopropylbenzoyl)oxy)propyl]pyrrolidin-1-ium bromide;
1-Cyclohexyl-1-[2-((2-isopropylbenzoyl)oxy)propyl]piperidin-1-ium bromide;
1-[2-((4-(tert-Butyl)benzoyl)oxy)propyl]-1-cyclohexylpyrrolidin-1-ium bromide;
1-[2-((4-(tert-Butyl)benzoyl)oxy)propyl]-1-cyclohexylpiperidin-1-ium bromide;
1-[2-((3-Chlorobenzo[b]thiophene-2-carbonyl)oxy)propyl]-1-cyclohexylpyrrolidin-1-ium bromide; and
1-[2-((3-Chlorobenzo[b]thiophene-2-carbonyl)oxy)propyl]-1-cyclohexylpiperidin-1-ium bromide.

9. The method of claim 8, wherein said administration is topical.

10. A method of treating itch in a patient, comprising administering to said patient a therapeutically effective amount of a compound selected from the group consisting of:
(i) N-[2-((2,6-Dimethylbenzoyl)oxy)propyl]-N,N-dimethylcyclohexanaminium iodide;
N-[2-(Benzoyloxy)propyl]-N,N-diethylcyclohexanaminium chloride;
N,N-Dimethyl-N-[2-((2,4,6-trimethylbenzoyl)oxy)propyl]cyclohexanaminium iodide;
N-[2-((2,6-Dimethoxybenzoyl)oxy)propyl]-N,N-dimethylcyclohexanaminium iodide;
N-[2-((2-Fluorobenzoyl)oxy)propyl]-N,N-dimethylcyclohexanaminium iodide;
N-[2-((2-Chlorobenzoyl)oxy)propyl]-N,N-dimethylcyclohexanaminium iodide;
N-[2-((2,4-Dichlorobenzoyl)oxy)propyl]-N,N-dimethyl-cyclohexanaminium iodide;
N,N-Dimethyl-N-[2-((2-methylbenzoyl)oxy)propyl]cyclohexanaminium iodide;
N-[2-((2-Isopropylbenzoyl)oxy)propyl]-N,N-dimethylcyclohexanaminium iodide;
N-[2-((4-(tert-Butyl)benzoyl)oxy)propyl]-N,N-dimethyl-cyclohexanaminium iodide;
N-[2-((4-Chlorobenzoyl)oxy)propyl]-N,N-dimethylcyclohexanaminium iodide;
N-[2-((3-Fluorobenzoyl)oxy)propyl]-N,N-dimethylcyclohexanaminium iodide;
N-[2-((4-Fluoro-2-(trifluoromethyl)benzoyl)oxy)propyl]-N,N-dimethylcyclohexanaminium iodide;
N,N-Dimethyl-N-[2-((3-(trifluoromethyl)benzoyl)oxy)propyl]cyclohexanaminium iodide;
N-[2-((2-(Trifluoromethyl)benzoyl)oxy)propyl]-N,N-dimethylcyclohexanaminium iodide;
N,N-Dimethyl-N-[2-((2-nitrobenzoyl)oxy)propyl]cyclohexanaminium iodide;
N-[2-((3,5-Dichlorobenzoyl)oxy)propyl]-N,N-dimethyl-cyclohexanaminium iodide;
N-[2-((4-Ethylbenzoyl)oxy)propyl]-N,N-dimethylcyclohexanaminium iodide;
N,N-Dimethyl-N-[2-((4-(trifluoromethyl)benzoyl)oxy)propyl]cyclohexanaminium iodide;
(S)—N,N-Dimethyl-N-[2-((2,4,6-trimethylbenzoyl)oxy)propyl]cyclohexanaminium iodide;
(S)—N-[2-((2,6-Dimethylbenzoyl)oxy)propyl]-N,N-dimethylcyclohexanaminium iodide;
(R)—N-[2-((2,6-Dimethylbenzoyl)oxy)propyl]-N,N-dimethylcyclohexanaminium iodide;
(R)—N,N-Dimethyl-N-[2-((2,4,6-trimethylbenzoyl)oxy)propyl]cyclohexanaminium iodide;
N-[2-((3-Isopropylbenzoyl)oxy)propyl]-N,N-dimethylcyclohexanaminium iodide;
N-[2-((2,6-Dichlorobenzoyl)oxy)propyl]-N,N-dimethyl-cyclohexanaminium iodide;
N,N-Dimethyl-N-[2-((2,4,6-trimethylbenzoyl)oxy)propyl]tetrahydro-2H-pyran-4-aminium iodide;
N-[2-((2,3-Dichlorobenzoyl)oxy)propyl]-N,N-dimethyl-cyclohexanaminium iodide;
N-[2-((Cyclohexanecarbonyl)oxy)propyl]-N,N-diethyl-cyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;
N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;
N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-((3-methylthiophene-2-carbonyl)oxy)propyl]cyclohexanaminium iodide;

N-[2-((4-(tert-Butyl)benzoyl)oxy)propyl]-N,N,4-trimethylcyclohexanaminium iodide;
N,N,4-Trimethyl-N-[2-((2,4,6-trimethylbenzoyl)oxy)propyl]cyclohexanaminium iodide;
N-[2-((2,6-Dimethylbenzoyl)oxy)ethyl]-N,N-dimethylcyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethylcyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl]-N,N-dimethylcyclohexanaminium iodide;
(S)—N-[2-((4-(tert-Butyl)benzoyl)oxy)propyl]-N,N-dimethylcyclohexanaminium iodide;
(R)—N-[2-((4-(tert-Butyl)benzoyl)oxy)propyl]-N,N-dimethylcyclohexanaminium iodide;
(S)—N-[2-((4-(tert-Butyl)benzoyl)oxy)propyl]-N,N-dimethylcyclohexanaminium bromide;
(R)—N-[2-((4-(tert-Butyl)benzoyl)oxy)propyl]-N,N-dimethylcyclohexanaminium bromide;
1-Cyclohexyl-1-[2-((2-isopropylbenzoyl)oxy)propyl]pyrrolidin-1-ium bromide;
1-Cyclohexyl-1-[2-((2-isopropylbenzoyl)oxy)propyl]piperidin-1-ium bromide;
1-[2-((4-(tert-Butyl)benzoyl)oxy)propyl]-1-cyclohexylpyrrolidin-1-ium bromide;
1-[2-((4-(tert-Butyl)benzoyl)oxy)propyl]-1-cyclohexylpiperidin-1-ium bromide;
1-[2-((3-Chlorobenzo[b]thiophene-2-carbonyl)oxy)propyl]-1-cyclohexylpyrrolidin-1-ium bromide; and
1-[2-((3-Chlorobenzo[b]thiophene-2-carbonyl)oxy)propyl]-1-cyclohexylpiperidin-1-ium bromide; and
(ii) a TRPV1 receptor activator.

11. The method of claim 10, wherein said TRPV1 receptor activator is selected from the group consisting of capsaicin, dihydrocapsaicin, nordihydrocapsaicin, lidocaine, articaine, procaine, tetracaine, mepivicaine, bupivicaine, eugenol, camphor, clotrimazole, N-arachidonoylvanillamine, anandamide, 2-aminoethoxydiphenyl borate, AM404, resiniferatoxin, phorbol 12-phenylacetate 13-acetate 20-homovanillate, olvanil, N-oleoyldopamine, N-arachidonyldopamine, 6'-iodoresiniferatoxin, a $C_{18}$ N-acylethanolamine, a lipoxygenase derivative, nonivamide, a fatty acyl amide of a tetrahydroisoquinoline inhibitor cysteine knot peptide, N-[2-(3,4-dimethylbenzyl)-3-(pivaloyloxy)propyl]-2-[4-(2-aminoethoxy)-3-methoxyphenyl]acetamide, N-[2-(3,4-dimethylbenzyl)-3-(pivaloyloxy)propyl]-N'-(4-hydroxy-3-methoxybenzyl)thiourea, hydroxy-α-sanshool, 2-aminoethoxydiphenyl borate, 10-shogaol, oleylgingerol, oleylshogaol, N-(4-tert-butylbenzyl)-N'-(4-hydroxy-3-methoxybenzyl)thiourea, aprindine, benzocaine, butacaine, cocaine, dibucaine, encainide, mexiletine, oxetacaine, prilocaine, proparacaine, procainamide, n-acetylprocainamide, chloroprocaine, dyclonine, etidocaine, levobupivacaine, ropivacaine, cyclomethycaine, dimethocaine, propoxycaine, trimecaine, and sympocaine.

12. The method of claim 10 or 11, wherein said administration is topical.

13. The method of claim 10, wherein said TRPV1 receptor activator of (ii) is co-administered with said compound of (i).

14. The method of claim 10, wherein said TRPV1 receptor activator of (ii) is administered prior to said compound of (i).

15. The method of claim 1, wherein the compound is selected from the group consisting of:
N-[2-((2,6-Dimethylbenzoy)oxy)propyl]-N,N-dimethylcyclohexanaminium iodide;
N-[2-(Benzoyloxy)propyl]-N,N-diethylcyclohexanaminium chloride;
N,N-Dimethyl-N-[2-((2,4,6-trimethylbenzoyl)oxy)propyl]cyclohexanaminium iodide;
N-[2-((2,6-Dimethoxybenzoyl)oxy)propyl]-N,N-dimethylcyclohexanaminium iodide;
N-[2-((2-Fluorobenzoyl)oxy)propyl]-N,N-dimethylcyclohexanaminium iodide;
N-[2-((2-Chlorobenzoyl)oxy)propyl]-N,N-dimethylcyclohexanaminium iodide;
N-[2-((2,4-Dichlorobenzoyl)oxy)propyl]-N,N-dimethylcyclohexanaminium iodide;
N,N-Dimethyl-N-[2-((2-methylbenzoyl)oxy)propyl]cyclohexanaminium iodide;
N-[2-((2-Isopropylbenzoyl)oxy)propyl]-N,N-dimethylcyclohexanaminium iodide;
N-[2-((4-(tert-Butyl)benzoyl)oxy)propyl]-N,N-dimethylcyclohexanaminium iodide; and
N-[2-((4-Chlorobenzoyl)oxy)propyl]-N,N-dimethylcyclohexanaminium iodide.
N-[2-((3-Fluorobenzoyl)oxy)propyl]-N,N-dimethylcyclohexanaminium iodide;
N-[2-((4-Fluoro-2-(trifluoromethyl)benzoyl)oxy)propyl]-N,N-dimethylcyclohexanaminium iodide;
N,N-Dimethyl-N-[2-((3-(trifluoromethyl)benzoyl)oxy)propyl]cyclohexanaminium iodide;
N-[2-((2-(Trifluoromethyl)benzoyl)oxy)propyl]-N,N-dimethylcyclohexanaminium iodide;
N,N-Dimethyl-N-[2-((2-nitrobenzoyl)oxy)propyl]cyclohexanaminium iodide;
N-[2-((3,5-Dichlorobenzoyl)oxy)propyl]-N,N-dimethylcyclohexanaminium iodide;
N-[2-((4-Ethylbenzoyl)oxy)propyl]-N,N-dimethylcyclohexanaminium iodide;
N,N-Dimethyl-N-[2-((4-(trifluoromethyl)benzoyl)oxy)propyl]cyclohexanaminium iodide;
(S)-N,N-Dimethyl-N-[2-((2,4,6-trimethylbenzoyl)oxy)propyl]cyclohexanaminium iodide;
(S)-N-[2-((2,6-Dimethylbenzoyl)oxy)propyl]-N,N-dimethylcyclohexanaminium iodide;
(R)-N-[2-((2,6-Dimethylbenzoyl)oxy)propyl]-N,N-dimethylcyclohexanaminium iodide;
(R)-N,N-Dimethyl-N-[2-((2,4,6-trimethylbenzoyl)oxy)propyl]cyclohexanaminium iodide;
N-[2-((3-Isopropylbenzoyl)oxy)propyl]-N,N-dimethylcyclohexanaminium iodide;
N-[2-((2,6-Dichlorobenzoyl)oxy)propyl]-N,N-dimethylcyclohexanaminium iodide;
N,N-Dimethyl-N-[2-((2,4,6-trimethylbenzoyl)oxy)propyl]tetrahydro-2H-pyran-4-aminium iodide;
N-[2-((2,3-Dichlorobenzoyl)oxy)propyl]-N,N-dimethylcyclohexanaminium iodide;
N-[2-((Cyclohexanecarbonyl)oxy)propyl]-N,N-diethylcyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;
N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;

N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-(3-methylthiophene-2-carbonyl)oxy)propyl]cyclohexanaminium iodide;
N-[2-((4-(tert-Butyl)benzoyl)oxy)propyl]-N,N,4-trimethylcyclohexanaminium iodide;
N,N,4-Trimethyl-N-[2-(2,4,6-trimethylbenzoyl)oxy)propyl]cyclohexanaminium iodide;
N-[2-((2,6-Dimethylbenzoyl)oxy)ethyl]-N,N-dimethylcyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethylcyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl]-N,N-dimethylcyclohexanaminium iodide;
(S)-N-[2-((4-(tert-Butyl)benzoyl)oxy)propyl]-N,N-dimethylcyclohexanaminium iodide;
(R)-N-[2-((4-(tert-Butyl)benzoyl)oxy)propyl]-N,N-dimethylcyclohexanaminium iodide;
(S)-N-[2-((4-(tert-Butyl)benzoyl)oxy)propyl]-N,N-dimethylcyclohexanaminium bromide; and
(R)-N-[2-((4-(tert-Butyl)benzoyl)oxy)propyl]-N,N-dimethylcyclohexanaminium bromide.

16. The method of claim 3, wherein the compound is selected from the group consisting of:
N-[2-((2,6-Dimethylbenzoyl)oxy)propyl]-N,N-dimethylcyclohexanaminium iodide;
N-[2-(Benzoyloxy)propyl]-N,N-diethylcyclohexanaminium chloride;
N,N-Dimethyl-N-[2-((2,4,6-trimethylbenzoyl)oxy)propyl]cyclohexanaminium iodide;
N-[2-((2,6-Dimethoxybenzoyl)oxy)propyl]-N,N-dimethylcyclohexanaminium iodide;
N-[2-((2-Fluorobenzoyl)oxy)propyl]-N,N-dimethylcyclohexanaminium iodide;
N-[2-((2-Chlorobenzoyl)oxy)propyl]-N,N-dimethylcyclohexanaminium iodide;
N-[2-((2,4-Dichlorobenzoyl)oxy)propyl]-N,N-dimethylcyclohexanaminium iodide;
N,N-Dimethyl-N-[2-((2-methylbenzoyl)oxy)propyl]cyclohexanaminium iodide;
N-[2-((2-Isopropylbenzoyl)oxy)propyl]-N,N-dimethylcyclohexanaminium iodide;
N-[2-((4-(tert-Butyl)benzoyl)oxy)propyl]-N,N-dimethylcyclohexanaminium iodide;
N-[2-((4-Chlorobenzoyl)oxy)propyl]-N,N-dimethylcyclohexanaminium iodide;
N-[2-((3-Fluorobenzoyl)oxy)propyl]-N,N-dimethylcyclohexanaminium iodide;
N-[2-(4-Fluoro-2-(trifluoromethyl)benzoyl)oxy)propyl]-N,N-dimethylcyclohexanaminium iodide;
N,N-Dimethyl-N-[2-((3-(trifluoromethyl)benzoyl)oxy)propyl]cyclohexanaminium iodide;
N-[2-((2-(Trifluoromethyl)benzoyl)oxy)propyl]-N,N-dimethylcyclohexanaminium iodide;
N,N-Dimethyl-N-[2-((2-nitrobenzoyl(oxy)propyl]cyclohexanaminium iodide;
N-[2-(3,5-Dichlorobenzoyl)oxy)propyl]-N,N-dimethylcyclohexanaminium iodide;
N-[2-((4-Ethylbenzoyl)oxy)propyl]-N,N-dimethylcyclohexanaminium iodide;
N,N-Dimethyl-N-[2-((4-(trifluoromethyl)benzoyl)oxy)propyl]cyclohexanaminium iodide;
(S)-N,N-Dimethyl-N-[2-((2,4,6-trimethylbenzoyl)oxy)propyl]cyclohexanaminium iodide;
(S)-N-[2-((2,6-Dimethylbenzoyl)oxy)propyl]-N,N-dimethylcyclohexanaminium iodide;
(R)-N-[2-((2,6-Dimethylbenzoyl)oxy)propyl]-N,N-dimethylcyclohexanaminium iodide;
(R)-N,N-Dimethyl-N-[2-((2,4,6-trimethylbenzoyl)oxy)propyl]cyclohexanaminium iodide;
N-[2-((3-Isopropylbenzoyl)oxy)propyl]-N,N-dimethylcyclohexanaminium iodide;
N-[2-((2,6-Dichlorobenzoyl)oxy)propyl]-N,N-dimethylcyclohexanaminium iodide;
N,N-Dimethyl-N-[2-((2,4,6-trimethylbenzoyl)oxy)propyl]tetrahydro-2H-pyran-4-aminium iodide;
N-[2-((2,3-Dichlorobenzoyl)oxy)propyl]-N,N-dimethylcyclohexanaminium iodide;
N-[2-((Cyclohexanecarbonyl)oxy)propyl]-N,N-diethylcyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;
N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;
N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-((3-methylthiophene-2-carbonyl)oxy)propyl]cyclohexanaminium iodide;
N-[2-((4-(tert-Butyl)benzoyl)oxy)propyl]-N,N,4-trimethylcyclohexanaminium iodide;
N,N,4-Trimethyl-N-[2-((2,4,6-trimethylbenzoyl)oxy)propyl]cyclohexanaminium iodide;
N-[2-((2,6-Dimethylbenzoyl)oxy)ethyl]-N,N-dimethylcyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethylcyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl]-N,N-dimethylcyclohexanaminium iodide;
(S)-N-[2-((4-(tert-Butyl)benzoyl)oxy)propyl]-N,N-dimethylcyclohexanaminium iodide;
(R)-N-[2-((4-(tert-Butyl)benzoyl)oxy)propyl]-N,N-dimethylcyclohexanaminium iodide;
(S)-N-[2-((4-(tert-Butyl)benzoyl)oxy)propyl]-N,N-dimethylcyclohexanaminium bromide; and
(R)-N-[2-((4-(tert-Butyl)benzoyl)oxy)propyl]-N,N-dimethylcyclohexanaminium bromide.

17. The method of claim 8, wherein the compound is selected from the group consisting of:
- N-[2-(2,6-Dimethylbenzoyl)oxy)propyl]-N,N-dimethylcyclohexanaminium iodide;
- N-[2-(Benzoyloxy)propyl]-N,N-diethylcyclohexanaminium chloride;
- N,N-Dimethyl-N-[2-((2,4,6-trimethylbenzoyl)oxy)propyl]cyclohexanaminium iodide;
- N-[2-((2,6-Dimethoxybenzoyl)oxy)propyl]-N,N-dimethylcyclohexanaminium iodide;
- N-[2-((2-Fluorobenzoyl)oxy)propyl]-N,N-dimethylcyclohexanaminium iodide;
- N-[2-((2-Chlorobenzoyl)oxy)propyl]-N,N-dimethylcyclohexanaminium iodide;
- N-[2-((2,4-Dichlorobenzoyl)oxy)propyl]-N,N-dimethylcyclohexanaminium iodide;
- N,N-Dimethyl-N-[2-((2-methylbenzoyl)oxy)propyl]cyclohexanaminium iodide;
- N-[2-(2-Isopropylbenzoyl)oxy)propyl]-N,N-dimethylcyclohexanaminium iodide;
- N-[2-((4-(tert-Butyl)benzoyl)oxy)propyl]-N,N-dimethylcyclohexanaminium iodide;
- N-[2-((4-Chlorobenzoyl)oxy)propyl]-N,N-dimethylcyclohexanaminium iodide;
- N-[2-(3-Fluorobenzoyl)oxy)propyl]-N,N-dimethylcyclohexanaminium iodide;
- N-[2-((4-Fluoro-2-(trifluoromethyl)benzoyl)oxy)propyl]-N,N-dimethylcyclohexanaminium iodide;
- N,N-Dimethyl-N-[2-((3-(trifluoromethyl)benzoyl)oxy)propyl]cyclohexanaminium iodide;
- N-[2-((2-(Trifluoromethyl)benzoyl)oxy)propyl]-N,N-dimethylcyclohexanaminium iodide;
- N,N-Dimethyl-N-[2-((2-nitrobenzoyl)oxy)propyl]cyclohexanaminium iodide;
- N-[2-((3,5-Dichlorobenzoyl)oxy)propyl]-N,N-dimethylcyclohexanaminium iodide;
- N-[2-((4-Ethylbenzoyl)oxy)propyl]-N,N-dimethylcyclohexanaminium iodide;
- N,N-Dimethyl-N-[2-((4-(trifluoromethyl)benzoyl)oxy)propyl]cyclohexanaminium iodide;
- (S)-N,N-Dimethyl-N-[2-((2,4,6-trimethylbenzoyl)oxy)propyl]cyclohexanaminium iodide;
- (S)-N-[2-((2,6-Dimethylbenzoyl)oxy)propyl]-N,N-dimethylcyclohexanaminium iodide;
- (R)-N-[2-((2,6-Dimethylbenzoyl)oxy)propyl]-N,N-dimethylcyclohexanaminium iodide;
- (R)-N,N-Dimethyl-N-[2-((2,4,6-trimethylbenzoyl)oxy)propyl]cyclohexanaminium iodide;
- N-[2-((3-Isopropylbenzoyl)oxy)propyl]-N,N-dimethylcyclohexanaminium iodide;
- N-[2-((2,6-Dichlorobenzoyl)oxy)propyl]-N,N-dimethylcyclohexanaminium iodide;
- N,N-Dimethyl-N-[2-((2,4,6-trimethylbenzoyl)oxy)propyl]tetrahydro-2H-pyran-4-aminium iodide;
- N-[2-((2,3-Dichlorobenzoyl)oxy)propyl]-N,N-dimethylcyclohexanaminium iodide;
- N-[2-((Cyclohexanecarbonyl)oxy)propyl]-N,N-diethylcyclohexanaminium iodide;
- N-[2-((3-Chlorobenzo[b]thiophene-2-carbonyl)oxy)propyl]-N,N-dimethylcyclohexanaminium iodide;
- N,N-Dimethyl-N-[2-((thiophene-2-carbonyl)oxy)propyl]cyclohexanaminium iodide;
- N-[2-((4-Isopropylbenzoyl)oxy)propyl]-N,N-dimethylcyclohexanaminium iodide;
- N,N-Dimethyl-N-[2-((thiophene-3-carbonyl)oxy)propyl]cyclohexanaminium iodide;
- N,N-Dimethyl-N-[2-((1-methyl-1H-pyrrole-2-carbonyl)oxy)propyl]cyclohexanaminium iodide;
- N-[2-((Benzo[b]thiophene-2-carbonyl)oxy)propyl]-N,N-dimethylcyclohexanaminium iodide;
- N-[2-((2,6-Dimethylbenzoyl)oxy)propyl]-N,N,4-trimethylcyclohexanaminium iodide;
- N,N-Dimethyl-N-[2-((3-methylthiophene-2-carbonyl)oxy)propyl]cyclohexanaminium iodide;
- N-[2-((4-(tert-Butyl)benzoyl)oxy)propyl]-N,N,4-trimethylcyclohexanaminium iodide;
- N,N,4-Trimethyl-N-[2-((2,4,6-trimethylbenzoyl)oxy)propyl]cyclohexanaminium iodide;
- N-[2-((2,6-Dimethylbenzoyl)oxy)ethyl]-N,N-dimethylcyclohexanaminium iodide;
- N-[2-((2,4,6-Trimethylbenzoyl)oxy)ethyl]-N,N-dimethylcyclohexanaminium iodide;
- N,N-Dimethyl-N-[2-((4-methylbenzoyl)oxy)propyl]cyclohexanaminium iodide;
- N-[2-((4-(tert-Butyl)benzoyl)oxy)ethyl]-N,N-dimethylcyclohexanaminium iodide;
- N-[2-((2-Ethylbenzoyl)oxy)propyl]-N,N-dimethylcyclohexanaminium iodide;
- N-[2-((2,4-Dimethylbenzoyl)oxy)propyl]-N,N-dimethylcyclohexanaminium iodide;
- (S)-N-[2-((4-(tert-Butyl)benzoyl)oxy)propyl]-N,N-dimethylcyclohexanaminium iodide;
- (R)-N-[2-((4-(tert-Butyl)benzoyl)oxy)propyl]-N,N-dimethylcyclohexanaminium iodide;
- (S)-N-[2-((4-(tert-Butyl)benzoyl)oxy)propyl]-N,N-dimethylcyclohexanaminium bromide; and
- (R)-N-[2-((4-(tert-Butyl)benzoyl)oxy)propyl]-N,N-dimethylcyclohexanaminium bromide.

18. The method of claim 10, wherein the compound is selected from the group consisting of:
- N-[2-((2,6-Dimethylbenzoyl)oxy)propyl]-N,N-dimethylcyclohexanaminium iodide;
- N-[2-(Benzoyloxy)propyl]-N,N-diethylcyclohexanaminium chloride;
- N,N-Dimethyl-N-[2-((2,4,6-trimethylbenzoyl)oxy)propyl]cyclohexanaminium iodide;
- N-[2-((2,6-Dimethoxybenzoyl)oxy)propyl]-N,N-dimethylcyclohexanaminium iodide;
- N-[2-((2-Fluorobenzoyl)oxy)propyl]-N,N-dimethylcyclohexanaminium iodide;
- N-[2-((2-Chlorobenzoyl)oxy)propyl]-N,N-dimethylcyclohexanaminium iodide;
- N-[2-(2,4-Dichlorobenzoyl)oxy)propyl]-N,N-dimethylcyclohexanaminium iodide;
- N,N-Dimethyl-N-[2-((2-methylbenzoyl)oxy)propyl]cyclohexanaminium iodide;
- N-[2-((2-Isopropylbenzoyl)oxy)propyl]-N,N-dimethylcyclohexanaminium iodide;
- N-[2-((4-(tert-Butyl)benzoyl)oxy)propyl]-N,N-dimethylcyclohexanaminium iodide;
- N-[2-((4-Chlorobenzoyl)oxy)propyl]-N,N-dimethylcyclohexanaminium iodide;
- N-[2-((3-Fluorobenzoyl)oxy)propyl]-N,N-dimethylcyclohexanaminium iodide;
- N-[2-((4-Fluoro-2-(trifluoromethyl)benzoyl)oxy)propyl]-N,N-dimethylcyclohexanaminium iodide;
- N,N-Dimethyl-N-[2-((3-(trifluoromethyl)benzoyl)oxy)propyl]cyclohexanaminium iodide;
- N-[2-((2-(Trifluoromethyl)benzoyl)oxy)propyl]-N,N-dimethylcyclohexanaminium iodide;
- N,N-Dimethyl-N-[2-((2-nitrobenzoyl)oxy)propyl]cyclohexanaminium iodide;

N-[2-((3,5-Dichlorobenzoyl)oxy)propyl]-N,N-dimethylcyclohexanaminium iodide;
N-[2-((4-Ethylbenzoyl)oxy)propyl]-N,N-dimethylcyclohexanaminium iodide;
N,N-Dimethyl-N-[2-((4-(trifluoromethyl)benzoyl)oxy)propyl]cyclohexanaminium iodide;
(S)-N,N-Dimethyl-N-[2-((2,4,6-trimethylbenzoyl)oxy)propyl]cyclohexanaminium iodide;
(S)-N-[2-((2,6-Dimethylbenzoyl)oxy)propyl]-N,N-dimethylcyclohexanaminium iodide;
(R)-N-[2-((2,6-Dimethylbenzoyl)oxy)propyl]-N,N-dimethylcyclohexanaminium iodide;
(R)-N,N-Dimethyl-N-[2-((2,4,6-trimethylbenzoyl)oxy)propyl]cyclohexanaminium iodide;
N-[2-(3-Isopropylbenzoyl)oxy)propyl]-N,N-dimethylcyclohexanaminium iodide;
N-[2-((2,6-Dichlorobenzoyl)oxy)propyl]-N,N-dimethylcyclohexanaminium iodide;
N,N-Dimethyl-N-[2-((2,4,6-trimethylbenzoyl)oxy)propyl]tetrahydro-2H-pyran-4-aminium iodide;
N-[2-((2,3-Dichlorobenzoyl)oxy)propyl]-N,N-dimethylcyclohexanaminium iodide;
N-[2-((Cyclohexanecarbonyl)oxy)propyl]-N,N-diethylcyclohexanaminium iodide;
N-[2-((3-Chlorobenzo[b]thiophene-2-carbonyl)oxy)propyl]-N,N-dimethylcyclohexanaminium iodide;
N,N-Dimethyl-N-[2-((thiophene-2-carbonyl)oxy)propyl]cyclohexanaminium iodide;
N-[2-((4-Isopropylbenzoyl)oxy)propyl]-N,N-dimethylcyclohexanaminium iodide;
N,N-Dimethyl-N-[2-((thiophene-3-carbonyl)oxy)propyl]cyclohexanaminium iodide;
N,N-Dimethyl-N-[2-((1-methyl-1H-pyrrole-2-carbonyl)oxy)propyl]cyclohexanaminium iodide;
N-[2-((Benzo[b]thiophene-2-carbonyl)oxy)propyl]-N,N-dimethylcyclohexanaminium iodide;
N-[2-((2,6-Dimethylbenzoyl)oxy)propyl]-N,N,4-trimethylcyclohexanaminium iodide;
N,N-Dimethyl-N-[2-((3-methylthiophene-2-carbonyl)oxy)propyl]cyclohexanaminium iodide;
N-[2-((4-(tert-Butyl)benzoyl)oxy)propyl]-N,N,4-trimethylcyclohexanaminium iodide;
N,N,4-Trimethyl-N-[2-((2,4,6-trimethylbenzoyl)oxy)propyl]cyclohexanaminium iodide;
N-[2-((2,6-DimethylbenzoyDoxy)ethyl]-N,N-dimethylcyclohexanaminium iodide;
N-[2-((2,4,6-Trimethylbenzoyl)oxy)ethyl]-N,N-dimethylcyclohexanaminium iodide;
N,N-Dimethyl-N-[2-((4-methylbenzoyl)oxy)propyl]cyclohexanaminium iodide;
N-[2-((4-(tert-Butyl)benzoyl)oxy)ethyl]-N,N-dimethylcyclohexanaminium iodide;
N-[2-((2-Ethylbenzoyl)oxy)propyl]-N,N-dimethylcyclohexanaminium iodide;
N-[2-((2,4-Dimethylbenzoyl)oxy)propyl N,N-dimethylcyclohexanaminium iodide;
(S)-N-[2-((4-(tert-Butyl)benzoyl)oxy)propyl]-N,N-dimethylcyclohexanaminium iodide;
(R)-N-[2-((4-(tert-Butyl)benzoyl)oxy)propyl]-N,N-dimethylcyclohexanaminium iodide;
(S)-N-[2-((4-(tert-Butyl)benzoyl)oxy)propyl]-N,N-dimethylcyclohexanaminium bromide; and
(R)-N-[2-((4-(tert-Butyl)benzoyl)oxy)propyl]-N,N-dimethylcyclohexanaminium bromide.

\* \* \* \* \*